US012217830B2

(12) United States Patent
Phillips et al.

(10) Patent No.: US 12,217,830 B2
(45) Date of Patent: Feb. 4, 2025

(54) ESTIMATING TUMOR PURITY FROM SINGLE SAMPLES

(71) Applicant: Personalis, Inc., Menlo Park, CA (US)

(72) Inventors: Nicholas Phillips, Menlo Park, CA (US); Jason Harris, Menlo Park, CA (US)

(73) Assignee: Personalis, Inc., Fremont, CA (US)

( * ) Notice: Subject to any disclaimer, the term of this patent is extended or adjusted under 35 U.S.C. 154(b) by 250 days.

(21) Appl. No.: 17/735,904

(22) Filed: May 3, 2022

(65) Prior Publication Data
US 2022/0259678 A1   Aug. 18, 2022

Related U.S. Application Data

(63) Continuation of application No. PCT/US2020/058951, filed on Nov. 4, 2020.

(60) Provisional application No. 62/931,096, filed on Nov. 5, 2019.

(51) Int. Cl.
G16B 40/20 (2019.01)
C12Q 1/6886 (2018.01)
G16B 20/20 (2019.01)
C12Q 1/686 (2018.01)
C12Q 1/6874 (2018.01)

(52) U.S. Cl.
CPC ........... *G16B 40/20* (2019.02); *C12Q 1/6886* (2013.01); *G16B 20/20* (2019.02); *C12Q 1/686* (2013.01); *C12Q 1/6874* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,683,202 A | 7/1987 | Mullis | |
| 4,988,617 A | 1/1991 | Landegren et al. | |
| 5,143,854 A | 9/1992 | Pirrung et al. | |
| 5,242,794 A | 9/1993 | Whiteley et al. | |
| 5,299,491 A | 4/1994 | Kawada | |
| 5,382,510 A | 1/1995 | Levine et al. | |
| 5,403,708 A | 4/1995 | Brennan et al. | |
| 5,412,087 A | 5/1995 | Mcgall et al. | |
| 5,432,065 A | 7/1995 | Fuller | |
| 5,472,672 A | 12/1995 | Brennan | |
| 5,494,810 A | 2/1996 | Barany et al. | |
| 5,641,658 A | 6/1997 | Adams et al. | |
| 5,928,907 A | 7/1999 | Woudenberg et al. | |
| 6,015,674 A | 1/2000 | Woudenberg et al. | |
| 6,045,996 A | 4/2000 | Cronin et al. | |
| 6,582,938 B1 | 6/2003 | Su et al. | |
| 6,754,655 B1 | 6/2004 | Segal | |
| 6,818,395 B1 | 11/2004 | Quake et al. | |
| 7,169,560 B2 | 1/2007 | Lapidus et al. | |
| 7,211,390 B2 | 5/2007 | Rothberg et al. | |
| 7,211,654 B2 | 5/2007 | Gao et al. | |
| 7,244,559 B2 | 7/2007 | Rothberg et al. | |
| 7,264,929 B2 | 9/2007 | Rothberg et al. | |
| 7,280,922 B2 | 10/2007 | Mei et al. | |
| 7,282,337 B1 | 10/2007 | Harris | |
| 7,300,788 B2 | 11/2007 | Matsuzaki et al. | |
| 7,323,305 B2 | 1/2008 | Leamon et al. | |
| 7,335,762 B2 | 2/2008 | Rothberg et al. | |
| 7,361,488 B2 | 4/2008 | Fan et al. | |
| 7,534,561 B2 | 5/2009 | Sana et al. | |
| 7,582,420 B2 | 9/2009 | Oliphant et al. | |
| 7,785,783 B2 | 8/2010 | Morley et al. | |
| 7,803,550 B2 | 9/2010 | Makarov et al. | |
| 8,026,094 B2 | 9/2011 | Green et al. | |
| 8,140,270 B2 | 3/2012 | Kingsmore et al. | |
| 8,415,101 B2 | 4/2013 | Garner | |
| 8,417,459 B2 | 4/2013 | Reese et al. | |
| 8,532,930 B2 | 9/2013 | Rabinowitz et al. | |
| 8,589,175 B2 | 11/2013 | Glauser et al. | |

(Continued)

FOREIGN PATENT DOCUMENTS

| | | |
|---|---|---|
| CN | 105044108 A | 11/2015 |
| CN | 109903811 | 6/2019 |

(Continued)

OTHER PUBLICATIONS

Staaf et al. Normalization of Illumina Infinium whole-genome SNP data improves copy number estimates and allelic intensity ratios. BMC Bioinformatics 9:409 (2008). (Year: 2008).*
VarScan. (2009). Retrieved from http:--varscan.sourceforge.net -.
Vasan, Biomarkers of cardiovascular disease: molecular basis and practical considerations. Circulation. May 16, 2006;113(19):2335-62.
Velculescu, et al. Characterization of the yeast transcriptome. Cell. Jan. 24, 1997;88(2):243-51.
Velculescu, et al. Serial analysis of gene expression. Science. Oct. 20, 1995;270(5235):484-7.
Vietsch, et al., Circulating DNA and Micro-RNA in Patients with Pancreatic Cancer, Pancreat Disord Ther. Jun. 2015; 5(2): 156. doi: 10.4172-2165-7092.1000156.

(Continued)

*Primary Examiner* — Samuel C Woolwine
(74) *Attorney, Agent, or Firm* — Orrick, Herrington & Sutcliffe, LLP

(57) ABSTRACT

The disclosure provides methods for estimating tumor purity from tumor samples without use of matched-normal controls. A set of genomic regions are identified based on a nucleic acid sequence data that is aligned to a reference genome. Each genomic region of the set of genomic regions includes one or more nucleotide-sequence variants relative to a corresponding genomic region of the reference genome. A B-allele frequency distribution for the biological sample is determined based on a B-allele frequency determined for each genomic region of the set of genomic regions. The B-allele frequency distribution is processed using a trained machine-learning model to estimate a metric identifying tumor purity in the biological sample.

14 Claims, 10 Drawing Sheets

(56) References Cited

U.S. PATENT DOCUMENTS

| | | |
|---|---|---|
| 8,785,353 B2 | 7/2014 | Van Eijk et al. |
| 8,862,410 B2 | 10/2014 | Hatchwell et al. |
| 9,051,602 B2 | 6/2015 | Oliphant et al. |
| 9,109,256 B2 | 8/2015 | Shuber |
| 9,128,861 B2 | 9/2015 | Bartha et al. |
| 9,183,496 B2 | 11/2015 | Harris et al. |
| 9,228,232 B2 | 1/2016 | Faham et al. |
| 9,329,170 B2 | 5/2016 | Clarke et al. |
| 9,416,422 B2 | 8/2016 | Cheung |
| 9,453,257 B2 | 9/2016 | Hoyal-Wrightson et al. |
| 9,512,485 B2 | 12/2016 | Richardson et al. |
| 9,725,755 B2 | 8/2017 | Poole et al. |
| 9,727,692 B2 | 8/2017 | Harris et al. |
| 9,745,626 B2 | 8/2017 | Bartha et al. |
| 9,909,186 B2 | 3/2018 | Schultz |
| 10,032,000 B1 | 7/2018 | Harris et al. |
| 10,125,399 B2 | 11/2018 | West |
| 10,174,375 B2 | 1/2019 | Lo et al. |
| 10,255,330 B2 | 3/2019 | Chandratillake et al. |
| 10,262,103 B2 | 4/2019 | Lehrer et al. |
| 10,266,890 B2 | 4/2019 | Bartha et al. |
| 10,415,091 B2 | 9/2019 | Bartha et al. |
| 10,450,611 B2 | 10/2019 | West et al. |
| 10,597,717 B2 | 3/2020 | Maguire et al. |
| 10,711,306 B2 | 7/2020 | Shiina et al. |
| 10,738,355 B2 | 8/2020 | Sahin et al. |
| 10,741,269 B2 | 8/2020 | Chudova et al. |
| 10,801,064 B2 | 10/2020 | West et al. |
| 10,801,070 B2 | 10/2020 | Clement et al. |
| 10,900,088 B2 | 1/2021 | Vogelstein et al. |
| 11,047,006 B2 | 6/2021 | Salk et al. |
| 11,062,789 B2 | 7/2021 | Chiu et al. |
| 11,124,824 B2 | 9/2021 | Sarwal et al. |
| 11,142,797 B2 | 10/2021 | Moynahan et al. |
| 11,155,867 B2 | 10/2021 | Bartha et al. |
| 11,286,530 B2 | 3/2022 | Rabinowitz et al. |
| 11,345,968 B2 | 5/2022 | Mortimer et al. |
| 2002/0006615 A1 | 1/2002 | Goldsborough et al. |
| 2002/0164629 A1 | 11/2002 | Quake et al. |
| 2003/0022200 A1 | 1/2003 | Vissing et al. |
| 2003/0096011 A1 | 5/2003 | Tracy |
| 2003/0099964 A1 | 5/2003 | Patil et al. |
| 2003/0100995 A1 | 5/2003 | Loraine et al. |
| 2003/0220777 A1 | 11/2003 | Kitchen et al. |
| 2005/0042668 A1 | 2/2005 | Perlin |
| 2005/0086035 A1 | 4/2005 | Peccoud et al. |
| 2005/0125474 A1 | 6/2005 | Pednault |
| 2005/0250125 A1 | 11/2005 | Novakoff |
| 2005/0260645 A1 | 11/2005 | Green et al. |
| 2006/0184489 A1 | 8/2006 | Weiner et al. |
| 2006/0278241 A1 | 12/2006 | Ruano |
| 2007/0111247 A1 | 5/2007 | Stephens et al. |
| 2007/0184436 A1 | 8/2007 | Myerson et al. |
| 2009/0026082 A1 | 1/2009 | Rothberg et al. |
| 2009/0029364 A1 | 1/2009 | Zirwes et al. |
| 2009/0127589 A1 | 5/2009 | Rothberg et al. |
| 2009/0183268 A1 | 7/2009 | Kingsmore et al. |
| 2009/0191565 A1 | 7/2009 | Lapidus et al. |
| 2009/0326832 A1 | 12/2009 | Heckerman et al. |
| 2010/0029498 A1 | 2/2010 | Gnirke et al. |
| 2010/0035252 A1 | 2/2010 | Rothberg et al. |
| 2010/0042438 A1 | 2/2010 | Moore et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009296 A1 | 1/2011 | Kain et al. |
| 2011/0105353 A1 | 5/2011 | Lo et al. |
| 2011/0184896 A1 | 7/2011 | Guyon |
| 2012/0058480 A1 | 3/2012 | Lewis et al. |
| 2012/0077682 A1 | 3/2012 | Bowcock et al. |
| 2012/0116688 A1 | 5/2012 | Bhubaneswar et al. |
| 2012/0143512 A1 | 6/2012 | Reese et al. |
| 2012/0208706 A1 | 8/2012 | Downing et al. |
| 2012/0270206 A1 | 10/2012 | Ginns et al. |
| 2012/0270212 A1 | 10/2012 | Rabinowitz et al. |
| 2013/0073217 A1 | 3/2013 | Dewey et al. |
| 2013/0090908 A1 | 4/2013 | Dewey et al. |
| 2013/0096011 A1 | 4/2013 | Rava et al. |
| 2013/0124100 A1 | 5/2013 | Drmanac et al. |
| 2013/0173177 A1 | 7/2013 | Pelleymounter |
| 2013/0178389 A1 | 7/2013 | Lapidus et al. |
| 2013/0296535 A1 | 11/2013 | Church et al. |
| 2013/0311448 A1 | 11/2013 | Thompson |
| 2013/0332081 A1 | 12/2013 | Reese et al. |
| 2014/0200147 A1 | 7/2014 | Bartha et al. |
| 2015/0051087 A1 | 2/2015 | Rabinowitz et al. |
| 2015/0057160 A1 | 2/2015 | Breuer et al. |
| 2016/0019341 A1 | 1/2016 | Harris et al. |
| 2016/0032396 A1 | 2/2016 | Diehn et al. |
| 2016/0041987 A1 | 2/2016 | Lapir et al. |
| 2016/0092631 A1 | 3/2016 | Yandell et al. |
| 2016/0122831 A1 | 5/2016 | West |
| 2016/0283484 A1 | 9/2016 | Chandratillake et al. |
| 2017/0166981 A1 | 6/2017 | Craig et al. |
| 2017/0199961 A1 | 7/2017 | Yelensky et al. |
| 2017/0253921 A1 | 9/2017 | Liu et al. |
| 2017/0316150 A1 | 11/2017 | Deciu et al. |
| 2017/0356053 A1 | 12/2017 | Otto et al. |
| 2018/0051338 A1 | 2/2018 | West et al. |
| 2018/0203974 A1 | 7/2018 | Venn |
| 2018/0258489 A1 | 9/2018 | Danenberg |
| 2018/0282801 A1 | 10/2018 | Zhao et al. |
| 2018/0363066 A1 | 12/2018 | Chalmers et al. |
| 2019/0127803 A1 | 5/2019 | Hacohen et al. |
| 2019/0189242 A1 | 6/2019 | Angiuoli et al. |
| 2019/0211406 A1 | 7/2019 | Babiarz et al. |
| 2019/0285518 A1 | 9/2019 | Lu et al. |
| 2019/0346442 A1 | 11/2019 | Carr et al. |
| 2020/0024669 A1 | 1/2020 | Spetzler et al. |
| 2020/0048711 A1 | 2/2020 | Snyder |
| 2020/0058377 A1 | 2/2020 | Bagaev et al. |
| 2020/0149097 A1 | 5/2020 | Otto et al. |
| 2020/0157604 A1 | 5/2020 | Plagnol |
| 2020/0202224 A1 | 6/2020 | Lanman et al. |
| 2020/0258597 A1 | 8/2020 | Perera |
| 2020/0258601 A1 | 8/2020 | Lau |
| 2020/0392584 A1 | 12/2020 | Almogy et al. |
| 2021/0054452 A1 | 2/2021 | West et al. |
| 2021/0062258 A1 | 3/2021 | Bartha et al. |
| 2021/0062276 A1 | 3/2021 | West |
| 2021/0210205 A1 | 7/2021 | Drake et al. |
| 2021/0238677 A1 | 8/2021 | West et al. |
| 2021/0363586 A1 | 11/2021 | Artsiomenka et al. |
| 2021/0398609 A1 | 12/2021 | Sigurjonsson et al. |
| 2022/0064733 A1 | 3/2022 | Alexander |
| 2022/0073985 A1 | 3/2022 | Nerenberg |
| 2022/0081716 A1 | 3/2022 | West et al. |
| 2022/0195530 A1 | 6/2022 | Diehn et al. |

FOREIGN PATENT DOCUMENTS

| | | | |
|---|---|---|---|
| CN | 110289047 A | * 9/2019 | ............ G16B 20/10 |
| EP | 0281927 | 6/1995 | |
| EP | 1342794 | 9/2003 | |
| EP | 3212808 | 9/2017 | |
| EP | 2861788 | 10/2018 | |
| WO | WO-2000018957 | 4/2000 | |
| WO | WO 2005098046 | 10/2005 | |
| WO | WO-2007055244 | 5/2007 | |
| WO | WO 2010054589 | 5/2010 | |
| WO | WO-2011050341 | 4/2011 | |
| WO | WO-2011057061 | 5/2011 | |
| WO | WO-2011057094 | 5/2011 | |
| WO | WO-2011091046 | 7/2011 | |
| WO | WO-2011160063 | 12/2011 | |
| WO | WO-2011160206 | 12/2011 | |
| WO | WO-2012142611 | 10/2012 | |
| WO | WO-2014053295 | 4/2014 | |

(56) References Cited

FOREIGN PATENT DOCUMENTS

| WO | WO-2014062717 | | 4/2014 |
| --- | --- | --- | --- |
| WO | WO-2014113204 | | 7/2014 |
| WO | WO-2014207245 | | 12/2014 |
| WO | WO-2015051275 | | 4/2015 |
| WO | WO-2015095889 | | 6/2015 |
| WO | WO-2016070131 | | 5/2016 |
| WO | WO-2017205823 | A1 | 11/2017 |
| WO | WO-2018053365 | A1 | 3/2018 |
| WO | 2018144782 | A1 | 8/2018 |
| WO | WO-2018195357 | A1 | 10/2018 |
| WO | 2018/222883 | A1 | 12/2018 |
| WO | WO-2019231856 | A1 | 12/2019 |
| WO | WO-2020132586 | A1 | 6/2020 |
| WO | WO-2020168008 | A1 | 8/2020 |
| WO | WO-2020252721 | A1 | 12/2020 |
| WO | WO2021016089 | A1 | 1/2021 |
| WO | WO-2022046947 | A1 | 3/2022 |

OTHER PUBLICATIONS

Vinay; et al., "Immune evasion in cancer: Mechanistic basis and therapeutic strategies", Seminars in Cancer Biology, Elsevier, 2015, 35, S185-S198.

Vincent, et al. Helicase-dependent isothermal DNA amplification. EMBO Rep. Aug. 2004;5(8):795-800. Epub Jul. 9, 2004.

Vos, et al. AFLP: a new technique for DNA fingerprinting. Nucleic Acids Res. Nov. 11, 1995; 23(21):4407-14.

Wagle, Nikhil et al., "High-Throughput Detection of Actionable Genomic Alterations in Clinical Tumor Samples by Targeted, Massively Parallel Sequencing", Cancer Discovery, Jan. 2012.

Walker, et al. Strand displacement amplification—an isothermal, in vitro DNA amplification technique. Nucleic Acids Res. Apr. 11, 1992 ;20(7):1691-6.

Wang, et al. Clonal evolution in breast cancer revealed by single nucleus genome sequencing. Nature. Aug. 14, 2014;512(7513):155-60. doi: 10.1038-nature13600. Epub Jul. 30, 2014.

Wang, K. (2010). ANNOVAR Documentation. Retrieved from http:annovar.openbioinformatics.org.

Warren, R.L. et al., Targeted assembly of short sequence reads. PLOS One, 6(5): May 5, 2011; p. e19816, XP055347747, DOI:10.1371-journal.pone-0019816.

Wasserstrom, et al. Reconstruction of cell lineage trees in mice. PLoS One. Apr. 9, 2008;3(4):e1939. doi: 10.1371-journal.pone.0001939.

Westin, et al. Anchored multiplex amplification on a microelectronic chip array. Nat Biotechnol. Feb. 2000;18(2):199-204.

Xiao, et al. Identifying mRNA, microRNA and protein profiles of melanoma exosomes. PLoS One. 2012;7(10):e46874. doi: 10.1371-journal.pone.0046874. Epub Oct. 9, 2012.

Yang, Yaping et al., "Clinical Whole-Exome Sequencing for the Diagnosis of Mendelian Disorders", New England Journal of Medicine, 369;16, Oct. 2, 2013.

Yeung et al., "LOH in the HLA Class I Region at 6p21 is Associated with Shorter Survival in Newly Diagnosed Glioblastoma", Clinical Cancer Research, pp. 1816-1826, Apr. 1, 2013.

Yi et al., "Sequencing of Fifty Human Exomes Reveals Adaptation to High Altitude", Science, 329(5987), pp. 75-78, Jul. 2, 2010.

Yu, Qi et al., "Chapter 3 MarkDuplicates", A practical introduction to GATK 4 on Biowulf, Jun. 15, 2021, accessed Jun. 16, 2022, available at https://hpc.nih.gov/training/gatk_tutorial/markdup.html.

Yu et al., "Mung Bean Nuclease Treatment Increases Capture Specificity of Microdroplet-PCR Based Targeted DNA Enrichment", PLOS ONE, Jul. 24, 2014, vol. 9, No. 7, p. e103491, XP055462530, DOI: 10.1371-journal.pone.0103491. abstract.

Zeerleder. The struggle to detect circulating DNA. Crit Care. 2006;10(3):142. Epub May 16, 2006.

Zheng et al., Estimating and accounting for tumor purity in the analysis of DNA methylation data from cancer studies, Genome Biology, Jan. 25, 2017, vol. 18, No. 17, pp. 1-14, <URL:https://doi.org/10.1186/s13059-016-1143-5>.

DeCathelineau, et al. The final step in programmed cell death: phagocytes carry apoptotic cells to the grave. Essays Biochem. 2003;39:105-17.

Diaz, et al. Insights into therapeutic resistance from whole-genome analyses of circulating tumor DNA. Oncotarget. Oct. 8, 2013;4(10):1856-7.

Diaz, et al. Liquid Biopsies: Genotyping Circulating Tumor DNA. JCO Feb. 20, 2014 vol. 32 No. 6 579-586.

Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.

Drmanac et al., "Human Genome Sequencing Using Unchained Base Reads on Self-Assembling DNA Nanoarrays", Science, 327(5961), pp. 78-81, Nov. 5, 2009.

Ellinger et al., "The role of cell-free circulating DNA in the diagnosis and prognosis of prostate cancer", Urologic Oncology 29:124-129 (2011), 124-129.

Elsharawy et al., "Accurate variant detection across non-amplified and whole genome amplified DNA using targeted next generation sequencing", BMC Genomics 13(500), pp. 1-14, Sep. 20, 2012.

Elshimali, et al. The clinical utilization of circulating cell free DNA (CCFDNA) in blood of cancer patients. Int J Mol Sci. Sep. 13, 2013;14(9):18925-58. doi: 10.3390-ijms140918925.

Esplin et al., Personalized sequencing and the future of medicine: discovery, diagnosis and defeat of disease. Pharmacogenomics. Nov. 2014. vol. 15, Nov. 14. pp. 1771-1790. Especially p. 1772 col. 2 para 3, p. 1773 col. 1 para 3, p. 1775 col. 1 para 2, p. 1776 fig 1, p. 1777 col. 1 para 1, p. 1777 col. 2 para 2, p. 1783 col. 1 para 3, p. 1785 col. 1 para 1.

Fahy, et al. Self-sustained sequence replication (3SR): an isothermal transcription-based amplification system alternative to PCR. PCR Methods Appl. Aug. 1991;1 (1):25-33.

Fairbrother et al., "RESCUE-ESE identifies Candidate Exonic Splicing Enhancers in Vertebrate Exons", Nucleic Acids Research, vol. 32, Jul. 1, 2004, pp. W187-W190.

Forshew et al., "Noninvasive Identification and Monitoring of Cancer Mutations by Targeted Deep Sequencing of Plasma DNA", Science Translational Medicine, May 30, 2012, vol. 4, Issue 136, 136ra68; DOI: 10.1126/scitranslmed.3003726.

Forshew et al., "Noninvasive Identification and Monitoring of Cancer Mutations by Targeted Deep Sequencing of Plasma DNA", Supplementary Materials, Science Translational Medicine, May 30, 2012, vol. 4, Issue 136, 136ra68; DOI: 10.1126/scitranslmed.3003726.

Fox, et al. Accuracy of Next Generation Sequencing Platforms. Next Gener Seq Appl. 2014;1. pii: 1000106; Published online Jun. 28, 2014.

Freed et al. Somatic mosaicism in the human genome. Genes 5.4 (Dec. 11, 2014): 1064-1094.

Freshney. Culture of Animal Cells: A Manual of Basic Technique and Specialized Applications. 6th Edition. 2010.

Frumkin, et al. Genomic variability within an organism exposes its cell lineage tree. PLoS Comput Biol. Oct. 2005;1 (5):e50. Epub Oct. 28, 2005.

Gilbert, Developmental Biology. 10th ed. Published by Sinauer Associates, Inc. (Sunderland, MA). Copyright 2014.

Gnirke, et al. Solution Hybrid Selection with Ultra-long Oligonucleotides for Massively Parallel Targeted Sequencing. Nat. Biotechnol. (Feb. 1, 2009), 27(2):182-9.

Golob, Mechanisms of cell fate acquisition in the differentiation of pluripotent stem cells. Dissertation. University of Washington. 2009; 110 pages.

Goris; et al., "The Immunogenetic Architecture of Autoimmune Disease", Cold Spring Harbor Perspectives in Biology, 2012, 4:a007260, 1-15.

Gottlieb, et al. The DiGeorge syndrome minimal critical region contains a goosecoid-like (GSCL) homeobox gene that is expressed early in human development. Am J Hum Genet. May 1997;60(5):1194-201.

(56) References Cited

OTHER PUBLICATIONS

Guo et al., "Exome sequencing generates high quality data in non-target regions", BMC Genomics 13(194), pp. 1-10, May 20, 2012. Main text.
Guo et al., "Exome sequencing generates high quality data in non-target regions", BMC Genomics 13(194), pp. 1-10, May 20, 2012. Supplementary Tables.
Guo et al., "Whole-genome and whole-exome sequencing of bladder cancer identifies frequent alterations in genes involved in sister chromatid cohesion and segregation", nature Genetics, Letters, vol. 45, No. 12, Dec. 2013. Published online Oct. 13, 2013.
Haferlach et al., "Mutations of the TP53 gene in acute myeloid leukemia are strongly associated with a complex aberrant karyotype", Leukemia. Aug. 2008;22(8):1539-41. doi: 10.1038/leu.2008.143. Epub Jun. 5, 2008.
Hamfjord et al., Plos ONE at www.plosone.org Apr. 2012, vol. 7, Issue 4, e34150.
Hiratani, et al., Replication timing and transcriptional control: beyond cause and effect—part II. Curr Opin Genet Dev. Apr. 2009;19(2):142-9. doi: 10.1016-j.gde.2009.02.002. Epub Apr. 1, 2009.
Hirschhorn, et al. Human intersex with chromosome mosaicism of type XY-XO. Report of a case. N Engl J Med. Nov. 24, 1960;263:1044-8.
Holstege, et al. Somatic mutations found in the healthy blood compartment of a 115-yr-old woman demonstrate oligoclonal hematopoiesis. Genome Res. May 2014;24(5):733-42. doi: 10.1101-gr.162131.113. Epub Apr. 23, 2014.
Hong, et al., Tracking the origins and drivers of subclonal metastatic expansion in prostate cancer. Nature Communications, Apr. 1, 2015; vol. 6, No. 1: pp. 1-12. XP055501144.
Huang, et al. Characterization of human plasma-derived exosomal RNAs by deep sequencing. BMC Genomics. May 10, 2013;14:319. doi: 10.1186-1471-2164-14-319.
Human Genome Overview GRCh37. Genome Reference Consortium, Feb. 27, 2009. 1 Page.
Human Genome Overview GRCh37.p13. Genome Reference Consortium, Jun. 28, 2013. 2 Pages.
Human Genome Overview GRCh38.p12. Genome Reference Consortium, Dec. 21, 2017. 2 Pages.
Illumina, "Coverage Depth Recommendations", Science and Education, 2018, Website, 1-3.
Illumina, "Interpreting Infinium Assay Data for Whole-Genome Structural Variation", Technical Note: DNA Analysis, 2010. Website, 1-8.
Illumina Technical Note: Informatics. Sequencing coverage information methods for human whole-genome sequencing. A overview of Illumina coverage calculation methods using BaseSpace or third party analysis tools. 2014. 2 pages.
Illumina Technical Note: Sequencing. Estimating sequencing coverage. Before starting a sequencing experiment, you should know the depth of sequencing you want to achieve. This technical note helps you estimate that coverage. 2014. 2 pages.
Illumina.org "AmpliSeq for Illumina", Oct. 28, 2020, retrieved from the Internet: https://web.archive.org/web/20201021103737/https://www.illumina.com/products/by-brand/ampliseq/custom-panels.html>.
Ito et al., "Cancer Neoantigens: A Promising Source of Immunogens for Cancer Immunotherapy", Journal of Clinical & Cellular Immunology, Apr. 28, 2015, vol. 6, No. 2, 21559899.
Jenjaroenpun, et al. Characterization of RNA in exosomes secreted by human breast cancer cell lines using next-generation sequencing. PeerJ. Nov. 5, 2013;1:e201. doi: 10.7717-peerj.201. eCollection 2013.
Jung et al., "Cell-free DNA in the blood as a solid tumor biomarker—A critical appraisal of the literature", Clinica Chimica Acta 411:1611-1624 (Nov. 11, 2010).
Kalatskaya et al., "ISOWN: accurate somatic mutation identification in the absence of normal tissue controls", Genome Med., 9(59), Jun. 29, 2017, pp. 1-18.

Karam, et al. Apoptosis in Carcinogenesis and Chemotherapy. Published by Springer in 2009 ISBN: 978-1-4020-9596-2.
Kiialainen, et al. Performance of microarray and liquid based capture methods for target enrichment for massively parallel sequencing and SNP discovery. PLoS One. Feb. 9, 2011;6(2):e16486. doi: 10.1371-journal.pone.0016486.
Kinde, et al. Detection and quantification of rare mutations with massively parallel sequencing. Proc Natl Acad Sci US A. Jun. 7, 2011;108(23):9530-5. doi: 10.1073-pnas.1105422108. Epub May 17, 2011.
Koboldt et al., "VarScan: variant detection in massively parallel sequencing of individual and pooled samples", Bioinformatics, 25(17), pp. 2283-2285, Jun. 19, 2009.
Kokawa, et al. Apoptosis in the human uterine endometrium during the menstrual cycle. J Clin Endocrinol Metab. Nov. 1996;81(11):4144-7.
Koren, et al. Differential relationship of DNA replication timing to different forms of human mutation and variation. Am J Hum Genet. Dec. 7, 2012;91(6):1033-40. doi: 10.1016-j.ajhg.2012.10.018. Epub Nov. 21, 2012.
Boulesteix, et al., "Evaluating Microarray-Based Classifiers: An Overview", Cancer Informatics, Feb. 2008, pp. 77-97.
Fishel, et al., "Meta-Analysis of Gene Expression Data: A Predictor-Based Approach", Bioinformatics, vol. 23, No. 13, Jul. 1, 2007, pp. 1599-1606.
PCT/US2020/058951, "International Preliminary Report on Patentability", May 19, 2022, 9 pages.
PCT/US2020/058951, "International Search Report and Written Opinion", Feb. 2, 2021, 10 pages.
Saeys, et al., "A Review of Feature Selection Techniques in Bioinformatics", Bioinformatics, vol. 23, No. 19, Oct. 2007, pp. 2507-2517.
Smyth, "Limma: Linear Models for Microarray Data", In Bioinformatics and Computationaland Bioconductor, 2005, pp. 397-420.
Nucleosome Position by MNase-seq from ENCODE-Stanford-BYU. track settings from the UC Santa Cruz Genome Browser. 2011-2012. http://hgdownload.cse.ucsc.edu-goldenPath-hg19-encodeDCC-wgEncodeSydhNsome.
Ochman, et al. Genetic applications of an inverse polymerase chain reaction. Genetics. Nov. 1988;120(3):621-3.
Ozsolak, et al. Direct RNA sequencing. Nature. Oct. 8, 2009;461(7265):814-8. doi: 10.1038-nature08390. Epub Sep. 23, 2009.
Park. Scientists Devise a Blood Test to Predict Heart Attack. Time Magazine. Mar. 22, 2012. 2 pages.
Pasaniuc, et al. Extremely low-coverage sequencing and imputation increases power for genome-wide association studies. Nat Genet. May 20, 2012;44(6):631-5. doi: 10.1038-ng.2283. With Supplementary Information.
Pathak et al., "Circulating Cell-Free DNA in Plasma/Serum of Lung Cancer Patients as a Potential Screening and Prognostic Tool", Clinical Chemistry 52:10, 1833-1842 (2006).
Pierce, et al. Linear-after-the-exponential polymerase chain reaction and allied technologies. Real-time detection strategies for rapid, reliable diagnosis from single cells. Methods Mol Med. 2007;132:65-85.
Podlaha, Ondrej et al., "Evolution of the cancer genome", Trends Genet. Apr. 2012; 28(4): 155-163. doi:10.1016/j.tig.2012.01.003.
Pritchard et al., "ColoSeq Provides Comprehensive Lynch and Polyposis Syndrome Mutational Analysis Using Massively Parallel Sequencing", Journal of Molecular Diagnostics, vol. 14, No. 4, Jul. 2012.
Punnoose, et al. Molecular biomarker analyses using circulating tumor cells. PLoS One. Sep. 8, 2010;5(9):e12517. doi: 10.1371-journal.pone.0012517.
Ralph, et al., Consistency of VDJ Rearrangement and Substitution Parameters Enables Accurate B Cell Receptor Sequence Annotation. PLOS computational biology, Jan. 11, 2016; 12(1): e1004409. https:--doi.org-10.1371-journal.1004409.
Richter. Fecal DNA screening in colorectal cancer. Can J Gastroenterol. Jul. 2008;22(7):631-3.

(56) References Cited

OTHER PUBLICATIONS

Robinson, et al. Strategies for exome and genome sequence data analysis in disease gene discovery projects. Clinical Genetics, vol. 80, No. 2, pp. 127-132 (2011) See the whole document.
Robinson; et al., "The Human Phenotype Ontology: A Tool for Annotating and Analyzing Human Hereditary Disease", The American Journal of Human Genetics, Nov. 7, 2008, 83, 610-615.
Rogozin, et al. Somatic mutation hotspots correlate with DNA polymerase eta error spectrum. Nat Immunol. Jun. 2001;2(6):530-6.
Rosenfeld, et al. Novel multi-nucleotide polymorphisms in the human genome characterized by whole genome and exome sequencing. Nucleic Acids Research, Article No. gkq408, pp. 1-10 (2010) See abstract; and pp. 8-9.
Ross, et al. Characterizing and measuring bias in sequence data. Genome Biology, vol. 14, No. 5, Article No. R51, pp. 1-20 (e-pub, May 29, 2013) See the whole document.
Ross. Introduction to Oncogenes and Molecular Cancer Medicine. Copyright 1998 Springer-Verlag New York, Inc. ISBN : 0-387-98392-9.
Saiki, et al. Analysis of enzymatically amplified beta-globin and HLA-DQ alpha DNA with allele-specific oligonucleotide probes. Nature. Nov. 13-19, 1986;324(6093):163-6.
Sambrook, et al. Molecular Cloning: A Laboratory Manual. 4th Edition, 2012.
Samuels, et al. Genetic mosaics and the germ line lineage. Genes (Basel). Apr. 17, 2015;6(2):216-37. doi: 10.3390-genes6020216.
Sandri, et al. Apoptosis, DNA damage and ubiquitin expression in normal and mdx muscle fibers after exercise. FEBS Lett. Oct. 16, 1995;373(3):291-5.
Schmitt, et al. Detection of ultra-rare mutations by next-generation sequencing. Proc Natl Acad Sci US A. Sep. 4, 2012;109(36):14508-13. doi: 10.1073-pnas.1208715109. Epub Aug. 1, 2012.
Schwarzenbach, et al. Detection and monitoring of cell-free DNA in blood of patients with colorectal cancer. Ann NY Acad Sci. Aug. 2008;1137:190-6. doi: 10.1196-annals.1448.025.
Shaw et al. Genomic analysis of circulating cell-free DNA infers breast cancer dormancy. Genome Research 22(2):220-231 (Oct. 11, 2011).
Shigemizu et al., "A practical method to detect SNVs and indels from whole genome and exome sequencing data", Scientific Reports, 3(1), pp. 1-6, Jul. 8, 2013. Main Text.
Shigemizu et al., "A practical method to detect SNVs and indels from whole genome and exome sequencing data", Scientific Reports, 3(1), pp. 1-6, Jul. 8, 2013; Supplementary Information.
Sims et al., "Sequencing depth and coverage: key considerations in genomic analyses," Nat Rev Genet. Feb. 2014;15(2):121-32. doi: 10.1038/nrg3642.
Singleton, et al. Phevor combines multiple biomedical ontologies for accurate identification of disease-causing alleles in single individuals and small nuclear families. Am J Hum Genet. Apr. 3, 2014;94(4):599-610. doi: 10.1016-j.ajhg.2014.03.010.
Snyder et al., "Genetic Basis for Clinical Response to CTLA-4 Blockade in Melanoma", Dec. 4, 2014, New England Journal of Medicine.
Soni, et al. Progress toward ultrafast DNA sequencing using solid-state nanopores. din Chem. Nov. 2007;53(11):1996-2001. Epub Sep. 21, 2007.
Spalding, et al. Retrospective birth dating of cells in humans. Cell. Jul. 15, 2005;122(1):133-43.
Stemmer, et al. Single-step assembly of a gene and entire plasmid from large numbers of oligodeoxyribonucleotides. Gene. Oct. 16, 1995; 164(1):49-53.
Stevanovic et al., Landscape of immunogenic tumor antigens in successful immunotherapy of virally induced epithelial cancer. Science, Apr. 14, 2017, vol. 356, No. 6334, pp. 200-205 Especially abstract, p. 1, 2, 15, Fig. S1.
Sudhakar, et al., Characterization of clonal immunoglobulin heavy (IGH) V-D-J gene rearrangements and the complementary-determining region in South Indian patients with precursor B-cell acute lymphoblastic leukemia. Blood Research, Mar. 2017; 52(1): 55-61.
Sulston, et al. Post-embryonic cell lineages of the nematode, Caenorhabditis elegans. Dev Biol. Mar. 1977;56(1):110-56.
Sulston, et al. The embryonic cell lineage of the nematode Caenorhabditis elegans. Dev Biol. Nov. 1983;100(1):64-119.
SureSelectXT Target Enrichment System for the Illumina Platform, (Jul. 2021), Agilent Technologies.
SVBio's services. http:--www.svbio.com-service-offerings-current-services. Accessed Oct. 1, 2014.
Swanton, Charles, "Plasma-derived Tumor DNA Analysis at Whole-Genome Resolution," Editorials, Clinical Chemistry 59:1, 6-8; Jan. 1, 2013.
Teer et al., "Exome sequencing: the sweet spot before whole genomes", Human Molecular Genetics, 19(R2), R145-R151, Aug. 12, 2010.
Tewhey, et al. Microdroplet-based PCR enrichment for large-scale targeted sequencing. Nat Biotechnol. Nov. 2009;27(11):1025-31. doi: 10.1038-nbt.1583. Epub Nov. 1, 2009.
The Human Cell Lineage Flagship Initiative. Last updated Nov. 10, 2010. 1 page. http:--www. lineage-flagsh ip.eu-.
Tug, et al. Exercise-induced increases in cell free DNA in human plasma originate predominantly from cells of the haematopoietic lineage. Exerc Immunol Rev. 2015;21 :164-73.
Turajlic et al., "Whole genome sequencing of matched primary and metastatic acral melanomas", Genome Research, 22(2), pp. 196-207, Feb. 22, 2012. Main document.
Turajlic et al., "Whole genome sequencing of matched primary and metastatic acral melanomas", Genome Research, 22(2), pp. 196-207, Feb. 22, 2012.Supplementary Figures.
Turajlic et al., "Whole genome sequencing of matched primary and metastatic acral melanomas", Genome Research, 22(2), pp. 196-207, Feb. 22, 2012. Supplementary Tables.
Valadi, et al. Exosome-mediated transfer of mRNAs and microRNAs is a novel mechanism of genetic exchange between cells. Nat Cell Biol. Jun. 2007;9(6):654-9. Epub May 7, 2007.
Vale et al., "Does anti-EGFR therapy improve outcome in advanced colorectal cancer? A systematic review and meta-analysis", Cancer Treatment Reviews 38 (2012) 618-625.
Van Driel, et al. A text-mining analysis of the human phenome. Eur J Hum Genet. May 2006;14(5):535-42.
Office Action for Japanese application No. 2022-526098, Japanese with English Translation, 8 pages.
Adessi, et al. Solid phase DNA amplification: characterisation of primer attachment and amplification mechanisms. Nucleic Acids Res. Oct. 15, 2000;28(20):E87.
Akey et al., "Haplotypes vs. single marker linkage disequilibrium tests: what do we gain?", European Journal of Human Genetics, Apr. 20, 2001, vol. 8, pp. 291-300.
Albert, et al. Direct selection of human genomic loci by microarray hybridization. Nat Methods. Nov. 2007;4(11):903-5. Epub Oct. 14, 2007.
Alter et al., "Clinical and molecular features associated with biallelic mutations in FANCD1/BRCA2," Journal of Medical Genetics 2007;44:1-9. doi: 10.1136/jmg.2006.043257.
Anderson et al., "Next Generation DNA Sequencing and the Future of Genomic Medicine", Genes 2010, 38-69; doi:10.3390/genes1010038.
Anonymous, "How to calculate the coverage for a NGS experiment", accessed Jul. 5, 2022, available at: https://www.ecseq.com/support/ngs/how-to-calculate-the-coverage-for-a-sequencing-experiment.
Anonymous, "Nature Definition of Mendelian Trait", Scitable by natureEDUCATION, 2014.
Anzar et al., "Neomutate: an Ensemble Machine Learning Framework for the Prediction of Somatic Mutations in Cancer", MBC Medical Genomics, col. 12, No. 1, Article 63, May 16, 2019.
ARUP's product "Exome Sequencing Symptom-Guided Analysis". http:--www.aruplab.com-guides-ug-tests-2006332.jsp. Accessed Oct. 1, 2014.

(56) References Cited

OTHER PUBLICATIONS

Asan, et al. Comprehensive comparison of three commercial human whole-exome capture platforms. Genome Biol. Sep. 28, 2011;12(9):R95. doi: 10.1186-GB-2011-12-9-r95.

Ausubel, et al. eds. Current Protocols in Molecular Biology. United States. Greene Publishing Associates and Wiley-Interscience. 1987. (Table of Contents).

Baingridge, et al. Whole exome capture in solution with 3 Gbp of data. Genome Biol. 2010;11(6):R62. doi: 10.1186-GB-2010-11-6-r62. Epub Jun. 17, 2010.

Baird, et al. Developing recombinant antibodies for biomarker detection. Cancer Biomark. 2010;6(5-6):271-9. doi: 10.3233-CBM-2009-0144.

Bamshad., "Exome sequencing as a tool for Mendelian disease gene discovery", Nature Reviews Genetics, Nov. 2011, 12, 745-755.

Beck, et al. Profile of the circulating DNA in apparently healthy individuals. Clin Chem. Apr. 2009;55(4):730-8. doi: 10.1373-clinchem.2008.113597. Epub Jan. 30, 2009.

Behjati, et al. Genome sequencing of normal cells reveals developmental lineages and mutational processes. Nature. Sep. 18, 2014;513(7518):422-5. doi: 10.1038-nature13448. Epub Jun. 29, 2014.

Benesova et al., "Mutation-based detection and monitoring of cell-free tumor DNA in peripheral blood of cancer patients", Analytical Biochemistry vol. 433, Issue 2, Feb. 15, 2013, pp. 227-234.

Bent, et al., "Enriching pathogen transcripts from infected samples: A capture-based approach to enhanced host-pathogen RNA sequencing", Analytical Biochemistry, Jul. 1, 2013; vol. 438, No. 1, pp. 90-96, XP055220731, DOI: 10.1016-j.ab.2013.03.008. abstract; pp. 91-92 "Material and Methods".

Bentley, et al., "Accurate whole human genome sequencing using reversible terminator chemistry," Nature. Nov. 6, 2008; 456(7218): 53-59. doi:10.1038/nature07517.

Biesecker, et al. A genomic view of mosaicism and human disease. Nat Rev Genet. May 2013;14(5):307-20. doi: 10.1038-nrg3424.

Bischoff, et al. Cell-free fetal DNA and intact fetal cells in maternal blood circulation: implications for first and second trimester noninvasive prenatal diagnosis. Hum Reprod Update. Nov.-Dec. 2002;8(6):493-500.

Blanco et al., "Highly Efficient DNA Synthesis by the Phage phi 29 DNA polymerase", Journal of Biological Chemistry, vol. 264, No. 15, pp. 8935-8940, May 25, 1989.

Blaschko. The nerve distribution in the skin in their relation to the diseases of the skin: a report to the VII Congress of the German Society of Dermatology, held at Wroclaw 28-30. May 1901. (in German with English abstract).

Boers et al., "High-Throughput Multilocus Sequence Typing: Bringing Molecular Typing to the Next Level," PLoS ONE 2012; 7(7):e39630.

Bonadona, et al. Cancer risks associated with germline mutations in MLH1, MSH2, and MSH6 genes in Lynch syndrome. JAMA. Jun. 8, 2011;305(22):2304-10. doi: 10.1001-jama.2011.743.

Braslavsky, et al. Sequence information can be obtained from single DNA molecules. Proc Natl Acad Sci USA. Apr. 1, 2003;100(7):3960-4. Epub Mar. 21, 2003.

Browne, et al. Increased promoter methylation in exfoliated breast epithelial cells in women with a previous breast biopsy. Epigenetics. Dec. 2011;6(12):1425-35. doi: 10.4161-epi.6.12.18280.

Brunstein., "In-depth coverage: some useful NGS terms", Nov. 2014, Website, 1-5.

Bryzgunova, et al. Isolation and comparative study of cell-free nucleic acids from human urine. Ann NY Acad Sci. Sep. 2006;1075:334-40.

Burrell et al., "The causes and consequences of genetic heterogeneity in cancer evolution" Nature. Sep. 19, 2013;501(7467):338-45. doi: 10.1038/nature12625.

Carlson, et al. Decoding cell lineage from acquired mutations using arbitrary deep sequencing. Nat Methods. Nov. 27, 2011;9(1):78-80. doi: 10.1038-nmeth.1781.

Cell fate map adapted from the Gilberts Developmental Biology, Fourth edition, Figure 9.1. Apr. 16, 2014. http:- -biology.stackexchange.com-questions-16555-where-does-the-fate-map-of-a-human-embryo-end.

Chan et al., "Cancer Genome Scanning in Plasma: Detection of Tumor-Associated Copy Number Aberrations, Single-Nucleotide Variants, and Tumoral Heterogeneity by Massively Parallel Sequencing", Clinical Chemistry 59:1, 211-224 (2013).

Chang, et al., Role of Bacteria in Oncogenesis. Clinical Microbiology Reviews, Oct. 2010; vol. 23 No. 4: p. 837-857.

Chen et al., "A Comprehensive, Highly Accurate Genomics Platform for Precision Immunotherapy: Simultaneously Characterize Tumors and the TME from a Single FFPE Sample", Available online at: https://www.personalis.com/asset/2019-aacr-a-comprehensive-highly-accurate-genomics-platform-for-precision-immunotherapy-simultaneously-characterize-tumors-and-the-tme-from-a-single-ffpe-sample/, Oct. 27, 2019, 1 page.

Chiu, et al. Effects of blood-processing protocols on fetal and total DNA quantification in maternal plasma. Clin Chem. Sep. 2001;47(9):1607-13.

Chiu et al., "Cell-Free DNA Fragmentomics: The New "Omica" on the Block", Clinical Chemistry, vol. 66, No. 12, Nov. 22, 2020, pp. 1480-1484.

Choi, et al. Genetic diagnosis by whole exome capture and massively parallel DNA sequencing. Proc Natl Acad Sci U S A. Nov. 10, 2009;106(45):19096-101. doi: 10.1073-pnas.0910672106. Epub Oct. 27, 2009.

Chu, Tianjiao et al., "Statistical model for whole genome sequencing and its application to minimally invasive diagnosis of fetal genetic disease", Bioinformatics, vol. 25, No. 10, 2009, pp. 1244-1250.

Clark, et al. Performance comparison of exome DNA sequencing technologies. Nat Biotechnol. Sep. 25, 2011;29(10):908-14. doi: 10.1038-nbt.1975.

Colella et al., "QuantiSNP: an Objective Bayes Hidden-Markov Model to detect and accurately map copy number variation using SNP genotyping data", Nucleic Acids Research, 2007, vol. 35, No. 6, 2013-2025; published online Mar. 6, 2007.

Craig, et al. Identification of genetic variants using bar-coded multiplexed sequencing. Nat Methods. Oct. 2008;5(10):887-93. Epub Sep. 14, 2008.

Damani, et al. Characterization of circulating endothelial cells in acute myocardial infarction. Sci Transl Med. Mar. 21, 2012 ;4(126):126ra33. doi: 10.1126-scitranslmed.3003451.

Data Sciences Platform @ Broad Institute. (2019). Genome Analysis ToolkitVariant Discovery in High-Throughput Sequencing Data. Retrieved from https:--www.broadinstitute.org.

Davies, et al., "Indications for Hematopoietic Cell Transplantation in Acute Leukemia," Biology of Blood and Marrow Transplantation 14:154-164 (2008). doi:10.1016/j.bbmt.2007.10.024.

Dawe, et al. Cell migration from baby to mother. Cell Adh Migr. Jan.-Mar. 2007;1(1):19-27. Epub Jan. 28, 2007.

Dawson, et al., "Analysis of Circulating Tumor DNA to Monitor Metastatic Breast Cancer," New England Journal of Medicine, 2013;368:1199-209; DOI:10.1056/NEJMoa1213261. Published online Mar. 13, 2013.

De La Chapelle. The incidence of Lynch syndrome. Fam Cancer. 2005;4(3):233-7.

De Mattos-Aruda et al., Circulating tumor cells and cell-free DNA as tools for managing breast cancer, Nat. Rev. Clin. Oncol 10, 377-389 (2013); published online May 28, 2013 doi:10.1038-nrclinonc.2013.80.

De Mattos-Aruda et al., "Capturing intra-tumor genetic heterogeneity by de novo mutation profiling of circulating cell-free tumor DNA: a proof of principle", Annals of Oncology, vol. 25, No. 9, Jul. 9, 2014, pp. 1729-1735.

Kosuri and Church, "Large-scale de novo DNA synthesis: technologies and applications," Nature Methods, 11:499-507, May 2014. Available at: http://www.nature.com-nmeth-journal-v11-n5-full-nmeth.2918.html.

Kothari, et al., "Emerging Technologies for Rapid Identification of Bloodstream Pathogens", Clinical Infectious Diseases, Apr. 24, 2014:59(2);272-8).

(56) References Cited

OTHER PUBLICATIONS

Krumm et al., "Copy number variation detection and genotyping from exome sequence data", Genome Research, 22(8), pp. 1525-1532, May 14, 2012.
Kuchler, et al. Buccal cells DNA extraction to obtain high quality human genomic DNA suitable for polymorphism genotyping by PCR-RFLP and Real-Time PCR. J Appl Oral Sci. Jul.-Aug. 2012;20(4):467-71.
Laktionov et al. "Cell-surface-bound nucleic acids: Free and cell-surface-bound nucleic acids in blood of healthy donors and breast cancer patients", Ann. NY Acad Sci 1022:221-227 (2004).
Lam, et al. Time course of early and late changes in plasma DNA in trauma patients. Clin Chem. Aug. 2003;49(8):1286-91.
Larson et al., "SomaticSniper: identification of somatic point mutations in whole genome sequencing data", Bioinformatics, 28(3), pp. 311-317, Dec. 6, 2011.
Lathe, R., Synthetic oligonucleotide probes deduced from amino acid sequence data: Theoretical and practical considerations. Journal of Molecular Biology, May 5, 1985; 183(1): 1-12.
Leamon, et al. A massively parallel PicoTiterPlate based platform for discrete picoliter-scale polymerase chain reactions. Electrophoresis. Nov. 2003; 24(21):3769-77.
Leary et al., "Development of Personalized Tumor Biomarkers Using Massively Parallel Sequencing", Science Translational Medicine, Feb. 24, 2010; 2(20): 20ra14.
Leary, et al. Detection of chromosomal alterations in the circulation of cancer patients with whole-genome sequencing. Sci Transl Med. Nov. 28, 2012;4(162):162ra154. doi: 10.1126-scitranslmed.3004742.
Levin, et al., Targeted next-generation sequencing of a cancer transcriptome enhances detection of sequence variants and novel fusion transcripts. Genome Biology, 2009. 10:R115.
Ley et al., "DNA Sequencing of a cytogenetically normal acute myeloid leukemia genome", Nature, vol. 456 | Nov. 6, 2008.
Li et al., "The Sequence Alignment/MAP format and SAMtools", Bioinformatics, 25(16), pp. 2078-2079, Jun. 8, 2009.
Li, et al., "Novel computational methods for increasing PCR primer design effectiveness in directed sequencing", BMC Bioinformatics. Apr. 11, 2008;9:191. doi: 10.1186-1471-2105-9-191.
Liao et al., "Targeted Massively Parallel Sequencing of Maternal Plasma DNA Permits Efficient and Unbiased Detection of Fetal Alleles", Clinical Chemistry 57:1, 92-101 (2011).
Liu, et al. Placental mosaicism for Trisomy 13: a challenge in providing the cell-free fetal DNA testing. J Assist Reprod Genet. May 2014;31(5):589-94. doi: 10.1007-s10815-014-0182-7. Epub Feb. 5, 2014.
Liu et al. Computational approaches for characterizing the tumor immune microenvironment, Immunology, Oct. 2019, vol. 158, No. 2, pp. 70-84, <URL: https://doi.org/10.1111/imm.13101>.
Lizardi, et al. Mutation detection and single-molecule counting using isothermal rolling-circle amplification. Nat Genet. Jul. 1998;19(3):225-32.
Lo et al., "Presence of fetal DN in maternal plasma and serum", Lancet 1997 350 485-87.
Lo, et al. Rapid clearance of fetal DNA from maternal plasma. Am J Hum Genet. Jan. 1999;64(1):218-24.
Lou, et al. High-throughput DNA sequencing errors are reduced by orders of magnitude using circle sequencing. Proc Natl Acad Sci U S A. Dec. 3, 2013;110(49):19872-7. doi: 10.1073-pnas.1319590110. Epub Nov. 15, 2013.
Lu et al., "Cancer immunotherapy targeting neoantigens", Seminars in Immunology, Elsevier, 2016, 28, 22-27; epub Nov. 30, 2015.
Madeleine et al., "Comprehensive Analysis of HLA-A, HLA-B, HLA-C, HLA-DRB1, and HLA-DQB1 Loci and Squamous Cell Cervical Cancer Risk", Cancer Res 2008; 68 (9), May 1, 2008.
Maluf et al., The Urine microRNA profile may help profile may help monitor post-transplant renal graft function, Kidney International. Jan. 1, 2014; vol. 85. No. 2: pp. 439-449. XP055442385.
Mamanova et al., "Target-enrichment strategies for next-generation sequencing", Nature Methods, vol. 7, No. 2, Feb. 2010.

Maguerat et al., "RNA Seq: from technology to biology", Cellular and Molecular Life Sciences, vol. 67, pp. 569-579; published online Oct. 27, 2009.
Margulies, et al. Genome sequencing in microfabricated high-density picolitre reactors. Nature. Sep. 15, 2005;437(7057):376-80. Epub Jul. 31, 2005.
Market, et al., V(D)J Recombination and the Evolution of the Adaptive Immune System. PLOS Biol. 2003; 1(1):e16. https:--doi.org-10.1371-journal.pbio.0000016.
Marsh. Pyrosequencing applications. Methods Mol Biol. 2007;373:15-24.
Masuzaki, et al. Detection of cell free placental DNA in maternal plasma: direct evidence from three cases of confined placental mosaicism. J Med Genet. Apr. 2004; 41 (4):289-92.
Mayo Clinic staff. Tests and Procedures, Urine cytology, Definition. Published Nov. 15, 2014. 3 pages. On the Mayo Clinic web site, at: http:--www.mayoclinic.org-tests-procedures-urine-cytology-basics-definition-prc-20020408.
Mercer, et al., Targeted sequencing for gene discovery and quantification using RNA captureSeq. Nat Protoc May 2014. vol. 9, No. 5, pp. 989-1009. Especially p. 990 col. 2 para 1, p. 990 Fig 2, p. 1991 Box 1, p. 992 col. 1 para 2.
Mertes et al., "Targeted enrichment of genomic DNA regions for next-generation sequencing", Briefings in Functional Genomics, vol. 10, No. 6, 374-386, Nov. 26, 2011.
Michaelson, et al. Whole-genome sequencing in autism identifies hot spots for de novo germline mutation. Cell. Dec. 21, 2012;151(7):1431-42. doi: 10.1016-j.cell.2012.11.019.
Miller, et al., Basic concepts of microarrays and potential applications in clinical microbiology. Clinical Microbiology Reviews, Oct. 2009, p. 611-633.
Misawa et al., "Significance of chromosomal alterations and mutations of the N-RAS and TP53 genes in relation to leukemogenesis of acute myeloid leukemia", Leuk Res. Jul. 1998;22(7):631-7. doi: 10.1016/s0145-2126(98)00056-3.
Mitra, et al. In situ localized amplification and contact replication of many individual DNA molecules. Nucleic Acids Res. Dec. 15, 1999;27(24):e34.
Moore, et al., Direct screening of blood by PCR and pyrosequencing for a 16S rRNA gene target from emergency department and intensive care unit patients being evaluated for bloodstream infection. Journal of clinical microbiology. Jan. 2016; 54(1): 99-105.
Moudrianakis, et al. Base sequence determination in nucleic acids with the electron microscope. 3. Chemistry and microscope of guanine-labeled DNA. Proc Natl Acad Sci U S A. Mar. 1965;53:564-71.
Muniappan, et al. The DNA polymerase beta replication error spectrum in the adenomatous polyposis coli gene contains human colon tumor mutational hotspots. Cancer Res. Jun. 1, 2002; 62(11 ):3271-5.
Murray, et al., Improved double-stranded DNA sequencing using the linear polymerase chain reaction. Nucleic Acids Research, vol. 17, No. 21. p. 8889. Nov. 11, 1989.
Naxerova, et al. Hypermutable DNA chronicles the evolution of human colon cancer. Proc Natl Acad Sci U S A. May 6, 2014; 111(18):E1889-98. doi: 10.1073-pnas.1400179111. Epub Apr. 21, 2014.
Naxerova, et al. Using tumour phylogenetics to identify the roots of metastasis in humans. Nat Rev Clin On col. May 2015; 12(5):258-72. doi: 10.1038-nrclinonc.2014.238. Epub Jan. 20, 2015.
Newman et al., "An ultrasensitive method for quantitating circulating tumor DNA with broad patient coverage", Nat Med. May 2014 ; 20(5) 548-554. doi:10.1038/nm.3519.
Newman et al., "An ultrasensitive method for quantitating circulating tumor DNA with broad patient coverage", Nat Med. May 2014 ; 20(5) 548-554. Supplementary Excel Spreadsheets.
Newman et al., "Integrated digital error suppression for improved detection of circulating tumor DNA", Nat Biotechnol. May 2016 ; 34(5): 547-555. doi:10.1038/nbt.3520.
Ng et al., "Exome sequencing identifies the cause of a mendelian disorder", Nature Genetics, 42(1), pp. 30-35, Nov. 13, 2009.

(56) References Cited

OTHER PUBLICATIONS

Ng, et al. Targeted capture and massively parallel sequencing of 12 human exomes. Nature. Sep. 10, 2009;461(7261):272-6. doi: 10.1038-nature08250. Epub Aug. 16, 2009.

Novocraft. (2014). Retrieved from http:--www.novocraft.com-.

Chapman, et al., Initial genome sequencing and analysis of multiple myeloma, Nature (2011), pp. 467-472.

Danovi, "A sequencing revolution in cancer," Milestones, Milestone 6, Nature, Feb. 2021, 1 page.

Ding, et al., "Genome remodelling in a basal-like breast cancer metastasis and xenograft," Nature (2010), pp. 999-1005.

Extended European Search Report in EP20885027.1, mailed Oct. 26, 2023, 11 pages.

Fluidigm, Specification Sheet for Access Array™ System, Oct. 2012, 4 pages.

Guan, et al., "Application of next-generation sequencing in clinical oncology to advance personalized treatment of cancer," Chinese J Cancer, Oct. 31, 2012, pp. 463-470.

Hohaus, et al., "Cell-free circulating DNA in Hodgkin's and non-Hodgkin's lymphomas," ScienceDirect, Aug. 2009 https://www.sciencedirect.com/science/article/pii/S0923753419409575, 17 pages.

Khurana et al., "Integrative Annotation of Variants from 1092 Humans: Application to Cancer Genomics," Science, Oct. 4, 2013, vol. 342, 11 pages.

Khurana et al., "Supporting online material for Integrative Annotation of Variants from 1092 Humans: Application to Cancer Genomics," Science Magazine Published by American Association for the Advancement of Science, Oct. 4, 2013, vol. 342, 97 pages.

Lee, et al., "The mutation spectrum revealed by paired genome sequences from a lung cancer patient," May 27, 2010, pp. 473-477.

Lee et al., "Performance evaluation method for read mapping tool in clinical panel sequencing," Genes & Genomics, Nov. 9, 2018, vol. 40, pp. 189-197.

Oesper et al., "Quantifying tumor heterogeneity in whole-genome and whole-exome sequencing data," Bioinformatics, 2014, vol. 30, No. 24, pp. 3532-3540.

Office Action in CN201980050741.1, mailed Nov. 22, 2023, 17 pages.

Office Action in JP2020-566295, mailed Nov. 10, 2023, 4 pages.

Okosun, et al., "Integrated genomic analysis identifies recurrent mutations and evolution patterns driving the initiation and progression of follicular lymphoma," Nature America (2014), 8 pages.

Okosun, et al., "Whole Genome Sequencing in Sequential Biopsies Reveals the Genetic Evolution of Follicular Lymphoma," Blood (2012) 120 (21) 145, 3 pages.

QIAamp® DNA Mini Kit and QIAamp DNA Blood Mini Kit Handbook, Feb. 2003, 68 pages.

Riester et al., "PureCN: copy number calling and SNV classification using targeted short read sequencing," Source Code for Biology and Medicine, 2016, vol. 11, No. 13, 13 pages.

Sahraeian et al., "Deep convolutional neural networks for accurate somatic mutation detection," Nature Communications, 2019, vol. 10, No. 1041, 10 pages.

Saunders, et al., "Strelka: accurate somatic small variant calling from sequenced tumor-normal sample pairs," Bioinformatics, May 10, 2012, pp. 1811-1817.

Shendure et al., "Next-generation DNA sequencing," Nat. Biotechnol. 2008, vol. 26, pp. 1135-1145.

Summerer et al., "Targeted high throughput sequencing of a cancer-related exome subset by specific sequence capture with a fully automated microarray platform," Genomics, 2010, vol. 95, pp. 241-246.

Sun et al., "Optimized data representation and convolutional neural network model for predicting tumor purity," bioRxiv preprint doi: https://doi.org/10.1101/805135, Oct. 17, 2019, 9 pages.

Sung et al., "Assessment of intratumoral heterogeneity with mutations and gene expression profiles," PLoS ONE, Jul. 16, 2019, vol. 14, No. 7, 15 pages.

Office Action in JP2022-526098, mailed Oct. 24, 2023, 5 pages.

Lu et al., "A synthetic biology approach identifies the mammalian UPR RNA ligase RtcB," National Institutes of Health, Mol Cell., Sep. 4, 2014, 55 (5), pp. 758-770.

Riaz et al., "Tumor and Microenvironment Evolution during Immunotherapy with Nivolumab," Cell, Nov. 2, 2017, vol. 171, No. 4, pp. 934-949.

Lam et al., "Performance comparison of whole-genome sequencing platforms," Nature Biotechnology (2012), vol. 30, No. 1, Jan. 2012, 7 pages.

Mcbride et al., "Use of Cancer-Specific Genomic Rearrangements to Quantify Disease Burden in Plasma from Patients with Solid Tumors," Genes, Chromosomes & Cancer (2010), 12 pages.

Meyerson et al., "Advances in understanding cancer genomes through second-generation sequencing," Nature Reviews (2010), vol. 11, Oct. 2010, pp. 685-696.

Ross et al., "Whole Cancer Genome Sequencing by Next-Generation Methods," American Journal of Clinical Pathology (2011), pp. 527-539.

Roberts et al., "The predictive capacity of personal genome sequencing." Science translational medicine. May 9, 2012;4(133):133ra58, pp. 1-9.

Extended European Search Report issued in corresponding EP application No. 24159457.1 on Oct. 4, 2024. 8 pages.

Office Action in CN202080090955.4, mailed Nov. 29, 2024, 7 pages.

* cited by examiner

| Synthetic Data | | | | |
|---|---|---|---|---|
| Model Name | Train RMSE | Train MAE | Test RMSE | Test MAE |
| Fully Connected | 0.088 | 0.062 | 0.099 | 0.063 |
| 1D CNN | 0.086 | 0.059 | 0.106 | 0.067 |
| 2D CNN | 0.081 | 0.058 | 0.112 | 0.076 |

RMSE: Root Mean Squared Error
MAE: Mean Absolute Error

| FASTQ Dilution Data - Cross Validation | | | | |
|---|---|---|---|---|
| Model Name | Train RMSE* | Train MAE* | Test RMSE | Test MAE |
| Fully Connected | 0.087 | 0.06 | 0.093 | 0.065 |
| 1D CNN | 0.057 | 0.034 | 0.112 | 0.086 |
| 2D CNN | 0.067 | 0.037 | 0.111 | 0.077 |

RMSE: Root Mean Squared Error     * CV training results are
MAE: Mean Absolute Error              averaged across folds

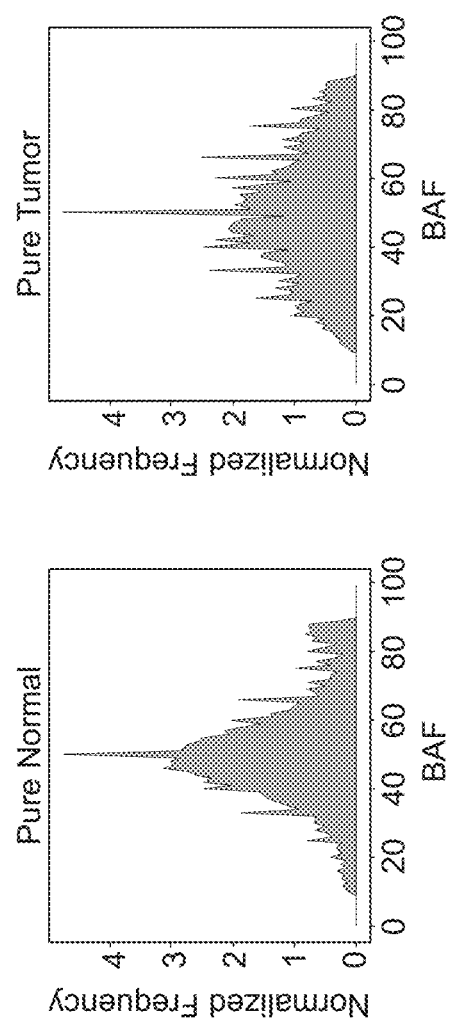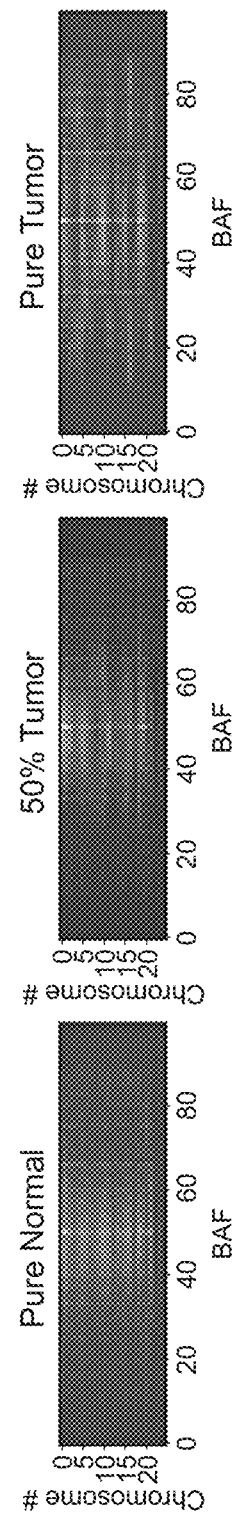
FIG. 7B
FIG. 7A
FIG. 7E
FIG. 7D
FIG. 7C

ESTIMATING TUMOR PURITY FROM SINGLE SAMPLES

CROSS REFERENCE TO RELATED APPLICATIONS

The present application is a continuation of International Application No. PCT/US2020/058951 filed Nov. 4, 2020, which claims priority to and the benefit of U.S. Provisional Patent Application No. 62/931,096, filed on Nov. 5, 2019, which is hereby incorporated by reference herein in its entirety for all purposes.

FIELD

This disclosure generally relates to systems and methods for estimating tumor purity from single samples. More specifically, but not by way of limitation, this disclosure relates to estimating tumor purity of a biological sample by processing B-allele frequency distribution using trained machine-learning models.

BACKGROUND

Tumor cellularity, also referred as "tumor purity", identifies a proportion of cancerous cells in a sample. An accurate estimation of tumor purity in a biological sample may contribute to an increased accuracy in detecting an amount of somatic mutations and/or copy number changes. This is because tumor purity indicates allele frequencies of somatic mutations that are present in a biological sample. The detection of somatic mutations and copy number variations can be used in turn to determine a stage of cancer of a subject or assess whether a particular cancer treatment is effective. Thus, tumor purity can inform determining a cancer stage and/or evaluating treatment efficacy.

Although tumor purity can be an effective metric, it can also be a confounding variable in several bioinformatics analyses. For example, conventional techniques that estimate the tumor purity can require histopathologic evaluation by pathologists, by manually inspecting images of samples to estimate tumor purity. Histopathologic evaluations including manual inspection of sample images, however, are likely to be subjective and inaccurate. Other conventional techniques for estimating tumor purity require comparing values (e.g., putative somatic variation) derived from nucleic acid sequence data of a given tumor sample with other values derived from nucleic acid sequencing data of a matched normal control sample. However, such normal control sample may not be available.

For example, a conventional technique estimates tumor purity of a sample as a function of an allelic fraction of somatic mutations that are unique to an individual's tumor. In the absence of a matched normal sample, identification of these somatic mutations is less precise, and the accuracy of estimated purity is greatly reduced. In some instances, matched normal controls are not available if sample providers did not collect or sequence normal controls (for example).

Accordingly, there is a need for accurately estimating tumor purity in a sample to facilitate detection, without relying on subjective analyses (e.g., histopathological evaluation) or a presence of a normal control sample.

SUMMARY

In some embodiments, a method of estimating tumor purity is provided. The method can include obtaining nucleic acid sequence data that represent a plurality of nucleic acid molecules of a tumor sample of a subject. The method can also include aligning the nucleic acid sequence data to a reference genome. The method can also include identifying, based on the aligned nucleic acid sequence data, a set of genomic regions. In some instances, each genomic region of the set of genomic regions includes one or more nucleotide-sequence variants relative to a corresponding genomic region of the reference genome.

The method can also include determining a B-allele frequency for each genomic region of the set of genomic regions. The method can also include determining, based on the B-allele frequencies of the set of genomic regions, a B-allele frequency distribution for the biological sample. The method can also include processing the B-allele frequency distribution using a trained machine-learning model to estimate a metric identifying tumor purity of the biological sample. The method can also include outputting the metric.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE FIGURES

Features, embodiments, and advantages of the present disclosure are better understood when the following Detailed Description is read with reference to the following figures.

FIGS. 7A-7E provide examples of plotted BAF distributions in accordance with some embodiments.

DETAILED DESCRIPTION

I. Overview

Figure 1:
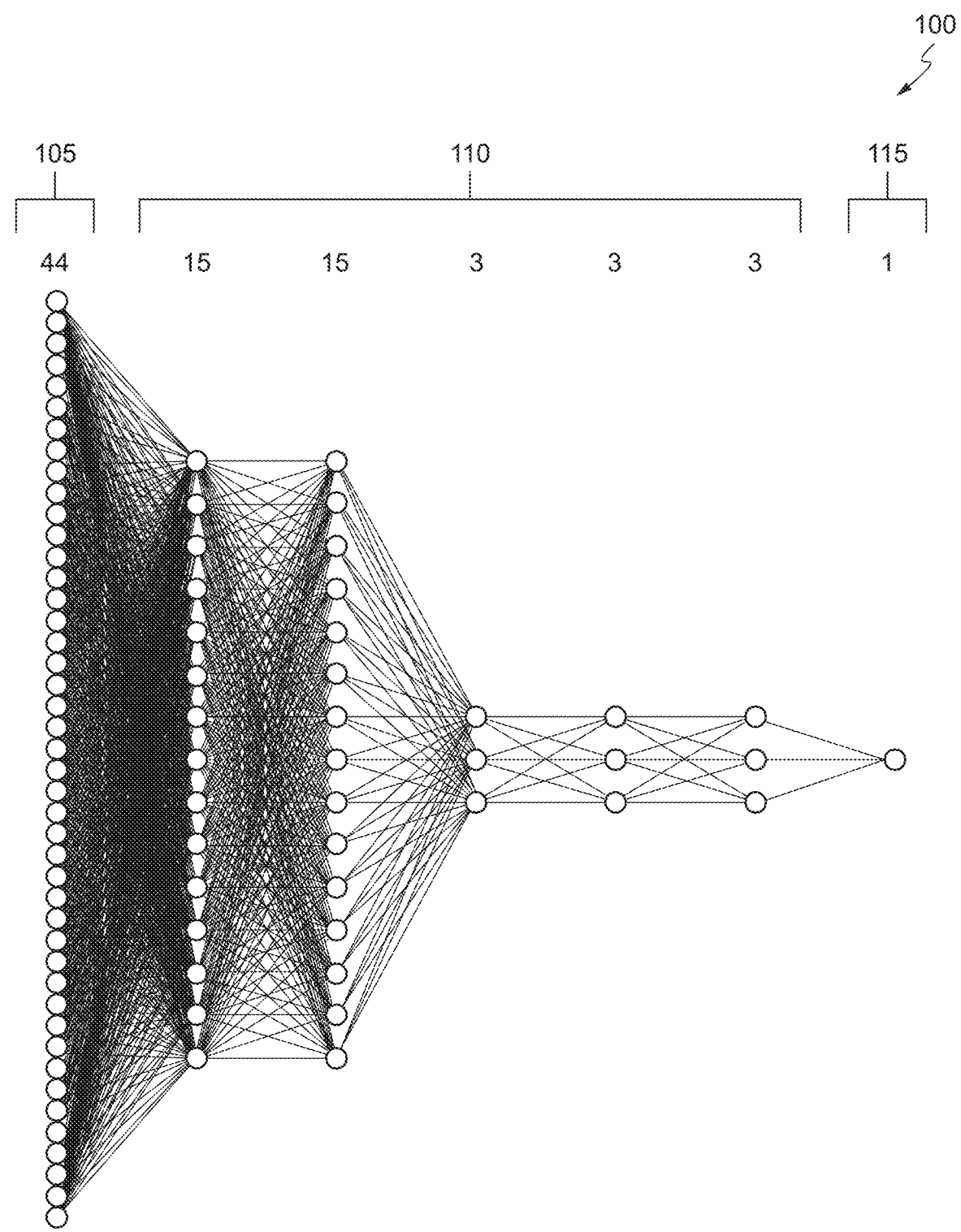
FIG. 1 illustrates a schematic diagram of a fully connected neural network for estimating tumor purity in accordance with some embodiments.

To address at least the above deficiencies of conventional systems, the present techniques can be used to estimate tumor purity by processing a B-allele frequency distribution for heterozygous sites in sequencing data using a trained machine-learning model. The trained machine-learning model may generate an estimated metric that identifies tumor purity in a biological sample, even in the absence of matching sequencing data of a normal control sample. The present techniques thus can accurately estimate tumor purity in the biological sample without a matched-normal control, which facilitates more accurate analysis of the nucleic-acid sequencing data from tumor-only samples.

Nucleic acid sequence data that represent a plurality of nucleic acid molecules of a tumor sample of a subject can be obtained. In some embodiments, the nucleic acid sequence data is whole exome sequencing data. The nucleic acid sequence data can be whole genome sequencing data. In some embodiments, the sequencing data is from a tumor sample. The tumor sample can be from a human subject. The nucleic acid sequence data can be generated from shotgun sequencing. In some embodiments, the nucleic acid sequence data can be generated by sequencing select parts of the genome or exome.

The nucleic acid sequence data can be aligned to a reference genome. Based on the aligned nucleic acid sequence data, a set of genomic regions can be identified. In some instances, each genomic region of the set of genomic regions includes one or more nucleotide-sequence variants relative to a corresponding genomic region of the reference genome. To identify the nucleotide-sequence variants, candidate variants can be identified, and reference and alternate read depths for the candidate variants can be calculated.

A B-allele frequency for each genomic region of the set of genomic regions can be determined. The B-Allele Frequency refers to a normalized measure of the allelic intensity ratio of two alleles (A and B), such that a BAF of 1 or 0 indicates the complete absence of one of the two alleles (e.g. AA or BB), and a BAF of 0.5 indicates the equal presence of both alleles (e.g. AB). Based on the B-allele frequencies of the set of genomic regions, a B-allele frequency distribution for the biological sample can be determined. In some embodiments, the B allele frequency distribution is normalized.

The B-allele frequency distribution can be processed using a trained machine-learning model to estimate a metric identifying tumor purity of the biological sample. As used herein, tumor purity or tumor cellularity refers to a proportion of cancer cells in the tumor sample. Tumor purity can be a metric used by various techniques for estimating tumor features that correspond direct clinical relevance. For example, the estimated tumor purity may directly alter a threshold of evidence required to identify copy number alterations, including those relating to approved companion diagnostics (e.g. EGFR exon 19 deletion in NSCLC). Tumor purity estimation can also be used to improve the quality (Sensitivity, PPV) of somatic variants calls by providing a prior on the expected allelic fractions of such variants. For example, tumor purity value of 60% may indicate that the tumor sample includes 60% tumor cells and 40% normal cells. Additionally or alternatively, tumor purity may indicate a number of cancer cells in the tumor sample. It is noted that wherever the term "tumor purity" is mentioned, the term "tumor cellularity" may be used interchangeably throughout herein.

The trained machine-learning model can be trained on a dataset generated in silico (e.g., nucleic acid sequence data generated via computer simulations). In some embodiments, the trained machine-learning model is trained on a training dataset generated from sequencing data derived from tumor cells diluted in normal cells. The trained machine-learning model can achieve a mean absolute error of less than about 0.2. In some embodiments, the trained machine-learning model achieves a root mean squared error of less than about 0.2.

In some embodiments, the trained machine-learning model includes a fully connected neural network. The fully connected network may include fully connected layers with Rectified Linear Unit (ReLU) activation functions. In some embodiments, output activation function of the fully connected neural network is a sigmoid function. A loss function of the fully connected neural network can be configured to calculate a mean squared error (MSE). In some embodiments, the fully connected neural network is tuned via hyperparameter search using random sampling with a linear search over layers, a linear search over size, a logarithmic search over learning rate, or a combination thereof.

In some instances, the trained machine-learning model includes a one-dimensional convolutional neural network. The one-dimensional convolutional neural network can be configured such that the B-allele frequency distribution can be used as input and can be encoded into an input size of a height of 25, a width of 1, and a depth of 100. In some embodiments, each layer of the one-dimensional convolutional neural network performs 1×1 convolutions, followed by ReLU activation function.

In some embodiments, the trained machine-learning model includes a two-dimensional convolutional neural network. In some embodiments, the B-allele frequency distribution of the two-dimensional convolutional neural network is used as input and is encoded into an input size defined by a height of 25, a width of 100, and a depth of 1. In some embodiments, each convolutional layer of the two-dimensional convolutional neural network is followed by a ReLU layer. The output of the two-dimensional convolutional neural network can be a densely connected layer with a sigmoid activation function. In addition, hyperparameters of the two-dimensional convolutional neural network can tuned by adjusting a number of layers, a filter size, a number of filters, or a combination thereof.

The estimated metric identifying the tumor purity can be output. For example, a report that includes estimated metric can be outputted. In some embodiments, the report includes information identifying the B allele frequency distribution. The report may also include information identifying at least one diagnostic marker and/or at least one prognostic marker. In some embodiments, the report includes information identifying predicted somatic variants. The report may also include a treatment recommendation. For example, the estimated tumor purity can indicate an increased methylation level in O-6-methylguanine-DNA methyltransferase, which is a prognostic biomarker for glioblastoma. In another example, the estimated tumor purity can be used to determine an amount of mutational burden of cancer cells, which may then be used to determine certain types of immunotherapy. Depending on an amount of the estimate tumor purity, it can be recommended whether a treatment for glioblastoma should be initiated. In some embodiments, the treatment recommendation includes a recommendation to administer a treatment to the human subject. The treatment recommendation may include a recommendation to not administer a treatment to the human subject.

Accordingly, embodiments of the present disclosure provide a technical advantage over conventional systems by more performing an accurate estimation of tumor purity that need not depend on data derived from a matching normal, control sample. The estimated tumor purity can be used to improve the accuracy of analysis and annotation of sequencing data from the tumor sample. One or more reports can be generated that account for the estimated tumor purity (e.g., diagnostic and/or prognostic reports). For example, the estimate of tumor purity can be used to improve the accuracy of diagnostic techniques to identify somatic mutations and/or copy number changes, and a report can be generated with details of the predicted somatic mutations and/or copy number changes.

One or more treatments can be administered to the patient or withheld from the patient based on the estimate of tumor purity and/or the report(s) facilitated by the estimate of tumor purity. For example, predicted somatic variants can be compared to one or more databases of known cancer mutations to diagnose or characterize the cancer. Variants can be identified that are associated with responsiveness or unresponsiveness to certain cancer treatments, and a treatment recommendation can be provided. The cancer can be treated based on the recommendation.

The following examples are provided to introduce certain embodiments. In the following description, for the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples in unnecessary detail. In other instances, well-known devices, processes, systems, structures, and techniques may be shown without necessary detail in order to avoid obscuring the examples. The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as an "example" is not necessarily to be construed as preferred or advantageous over other embodiments or designs.

II. Machine-Learning Models for Estimating Tumor Purity from Single Samples

A. Example Machine-Learning Models for Estimating Tumor Purity of a Biological Sample As discussed herein, tumor purity in a biological sample can be estimated by using a trained machine-learning model. The trained machine-learning model may correspond to one of various machine-learning models trained to estimate tumor purity of the biological sample. In some embodiments, the trained machine-learning model includes more than one model (e.g., 1, 2, 3, 4, 5, 6, 7, 8, 9, or 10 machine-learning models). For example, one of three machine-learning models can be trained to estimate tumor purity in nucleic acid sequencing data, including a fully connected neural network, a one-dimensional convolutional neural network, and a two-dimensional convolutional neural network. In some instances, the trained machine-learning model includes a deep neural network. Deep neural network can be used to capture the internal structure of increasingly larger and high-dimensional data sets (e.g., nucleic acid sequence data). Deep neural networks can identify high-level features, improve performance over traditional statistical models, increase interpretability, and provide additional understanding about the structure of the nucleic acid sequence data.

The trained machine-learning model may include hyperparameters. Hyperparameters can be a configuration that is external to the model and whose value are not be estimated from data (e.g., training data, input data). In some instances, hyperparameters are tuned, e.g., tuned to solve a given predictive modeling problem. In some instances, a hyperparameter is used to help estimate model parameters. The hyperparameters can be specified by a user. In some instances, a hyperparameter can be determined using a set of heuristic algorithms.

FIG. 1 illustrates a schematic diagram 100 of a fully connected neural network for estimating tumor purity in accordance with some embodiments. An input layer 105 of the fully connected neural network is shown on the left, followed by a set of hidden layers 110. An output layer 115 is shown on the right. For the fully-connected network, input features can include whole-exome, B-allele frequency (BAF) distributions of nucleotide-sequence variants identified in a biological sample. The fully connected neural network may include a series of fully connected layers with ReLU activation functions, and an output activation function can be a sigmoid function. In some instances, a loss function of the fully connected neural network is configured to generate a mean squared error (MSE). The fully connected neural network can be optimized via hyperparameter search using random sampling, including linear search over layers and size, and logarithmic search over learning rate. Each output dimension of the fully connected neural network can depend on each input dimension. In some instances, a fully connected neural network can be a feed forward neural network.

A convolutional neural network can be trained to estimate tumor purity of the biological sample. The convolutional neural network can rely on local connections and tied weights across the units followed by feature pooling (subsampling) to obtain translation invariant descriptors. The basic convolutional neural network architecture can comprise one convolutional and pooling layer, optionally followed by a fully connected layer for supervised prediction. In some instances, convolutional neural networks are composed of multiple (e.g., >10) convolutional and pooling layers to better model the input space. Convolutional neural networks may require a large data set to be well trained. In some embodiments, convolutional neural networks use less parameters than a fully connected neural network by computing convolution on small regions of the input space and by sharing parameters between regions. A convolutional neural network can be a one-dimensional convolutional neural network. A convolutional neural network can be a two-dimensional convolutional neural network. In some embodiments, a convolutional neural network comprises three or more dimensions.

Figure 2:
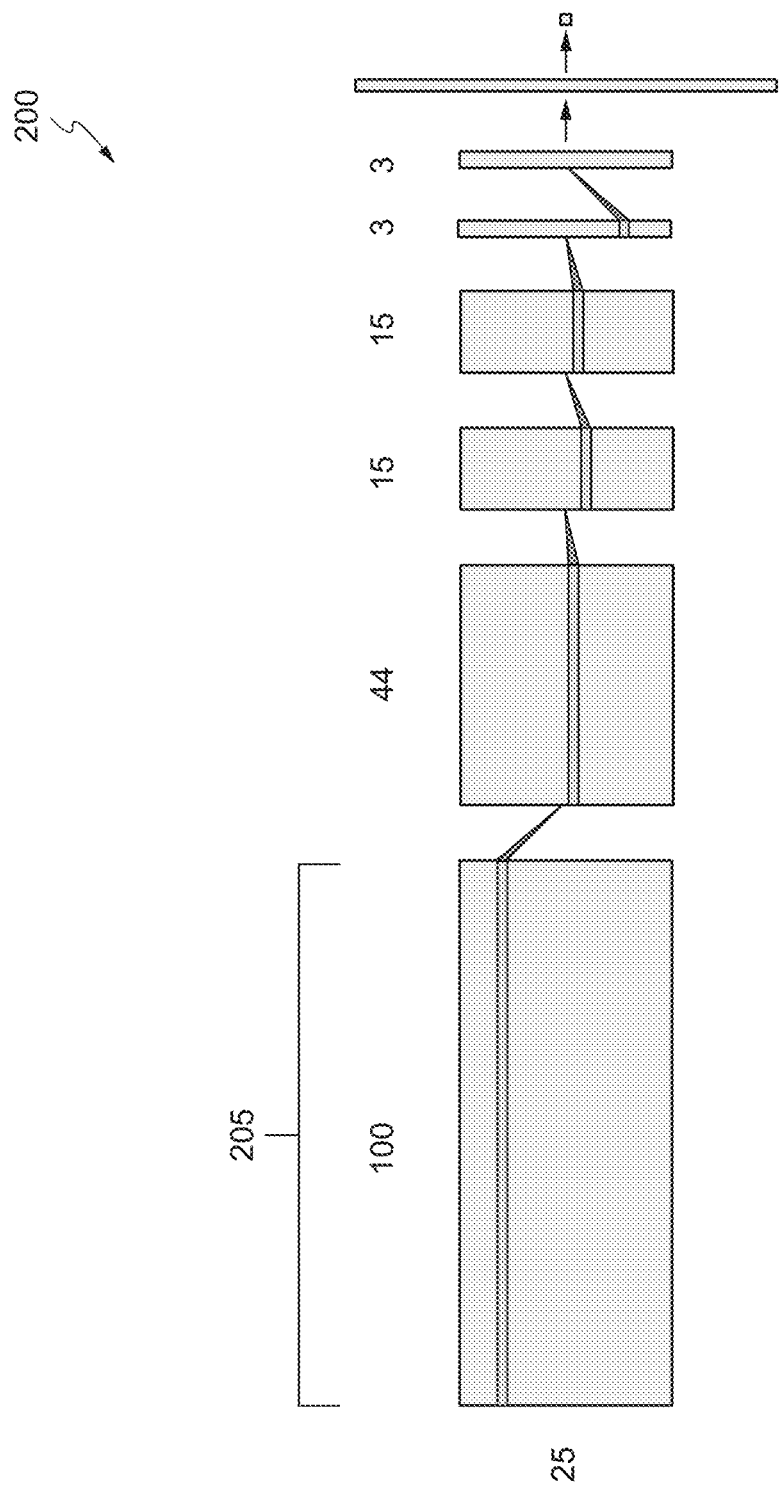
FIG. 2 illustrates a schematic diagram of a one-dimensional convolutional neural network for estimating tumor purity in accordance with some embodiments.

FIG. 2 illustrates a schematic diagram 200 of a one-dimensional convolutional neural network for estimating tumor purity in accordance with some embodiments. For the one-dimensional convolutional neural network, input features may include chromosome BAF distributions, which can be encoded into an input size defining a height of 25, width of 1, and a depth of 100. Each layer of the one-dimensional convolutional neural network may perform 1×1 convolutions, followed by a ReLU activation function. In some instances, a "Network-in-network" deep network structure is used. Effectively a 1D convolution with a stride of each layer's depth on flattened input is used. In some instances, hyperparameters corresponding to depth and layer size is obtained from a fully connected neural network (see FIG. 1), at which the hyperparameters corresponding to learning rate of the one-dimensional convolutional neural network can be tuned for optimization.

Figure 3:
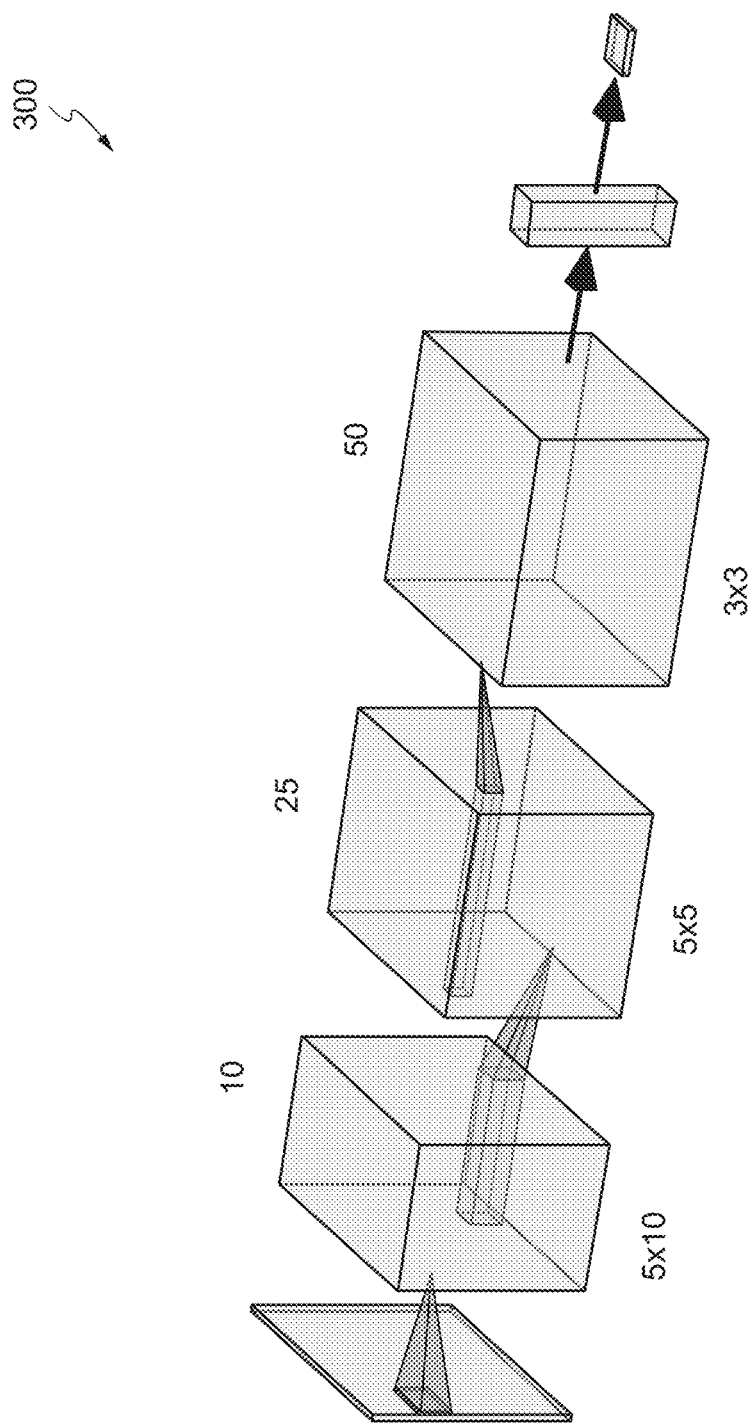
FIG. 3 illustrates a schematic diagram of a two-dimensional convolutional neural network for estimating tumor purity in accordance with some embodiments.

FIG. 3 illustrates a schematic diagram 300 of a two-dimensional convolutional neural network for estimating tumor purity in accordance with some embodiments. For the Two-dimensional convolutional neural network, input features may include chromosome BAF distributions, which can be encoded into an input size defining a height of 25, width of 100, and depth of 1. Each layer may correspond to a two-dimensional convolutional neural network layer (two-dimensional convolutional neural network layer), followed by a ReLU activation function. Output layer may correspond to a densely connected layer with a sigmoid activation function.

In some embodiments, hyperparameters for two-dimensional convolutional neural network are optimized by searching over a number of layers, a filter size, and a number of filters. Initial overfitting on the training set can be reduced by performing a dropout regularization and/or an L2 regularization.

Other types of machine-learning models can be trained to estimate tumor purity of the biological sample. In some embodiments, the machine-learning model corresponds to one or more of gradient boosting decision trees (e.g., XGBoost framework, LightGBM framework), bagging procedures, boosting procedures, and/or random forest algorithms. For example, a gradient-boosted decision tree can be trained to estimate tumor purity of the biological sample. Gradient boosting corresponds to a type of machine learning technique that can be used for regression and classification problems, and for producing a prediction model that may include an ensemble of weak prediction models, e.g., decision trees. In some instances, a gradient boosted decision tree can include, for example, an XGBoost framework or a LightGBM framework.

B. Training Dataset for Training Machine-Learning Models to Estimate Tumor Purity of a Biological Sample The machine-learning models for estimating tumor purity of a biological sample can be trained using supervised training algorithms. The supervised training algorithms may be used to train the machine-learning models to generate outputs corresponding to linear and/or logistic regression values corresponding to the tumor purity. The machine-learning models can be trained based on training datasets. In some instances, the training datasets includes sequencing datasets from pure tumor samples, pure normal samples, and a dilution series of tumor cells among normal cells. The sequencing datasets can be derived from biological samples of other subjects, including a biological sample from a subject diagnosed with cancer. The biological samples for the training datasets may correspond to malignant tissue, benign tissue, or a mixture thereof. In some embodiments, a biological sample including cancer tissue is obtained without a matching normal sample. Additionally or alternatively, a matched normal sample is obtained for training and testing of the machine-learning models (for example).

In some embodiments, the training dataset includes a training nucleotide-sequence variant dataset. The training variant dataset may correspond to a nucleic acid sequence data, in which nucleotide-sequence variants are identified. The nucleotide-sequent variants may include single nucleotide polymorphisms (SNPs), one or more single nucleotide variations, insertion-deletion mutations (indels), small insertions, small deletions, structural variant junctions, variable length tandem repeats, flanking sequences, and a combination thereof. In some instances, biased "Variant Call Format (VCF)-level" datasets are generated using artificial combination of VCF files generated from training samples, including tumor and normal samples. The training datasets may thus include in silico "dilutions" of the tumor sequences. VCF-level data sets can be generated with the characteristics outlined in TABLE 1. To train the machine-learning models, the machine-learning models can be fitted on the "train" set, hyperparameters can be tuned based on performance on the "train" and "dev" sets, and final performance can be evaluated on the "test" set.

TABLE 1

| Dataset name | train | dev | test |
| --- | --- | --- | --- |
| Size | 8000 | 1000 | 1000 |
| Unique samples | 800 | 100 | 100 |

In some embodiments, the training dataset includes training nucleic acid sequence data. The training nucleic acid sequence data may correspond to unbiased "FASTQ-level" datasets, which are generated via downsampling and combining reads from the training samples. The training samples may include normal and tumor samples. FASTQ-level data sets can be generated with a size of 99, and 11 unique samples, and may be from sequencing in vitro dilutions of tumor cells and matched-normal cells. In comparison to the VCF-level data sets, the FASTQ-level datasets can be at the read level rather than the variant level, and are therefore closer to raw data. In some instances, the FASTQ-level datasets are used to improve or optimize performance using more realistic data. As it is computationally intractable to generate a large FASTQ-level dataset, the machine-learning models can be trained using FASTQ-level dataset using transfer learning. Transfer learning is performed using machine-learning models pre-trained on the VCF-level data sets, with 5-fold cross-validation. In some instances, each machine-learning model can be trained on ⅘ of the training dataset and tested on ⅕ of the training dataset for each iteration.

Figures 4A, 4B, 4C:
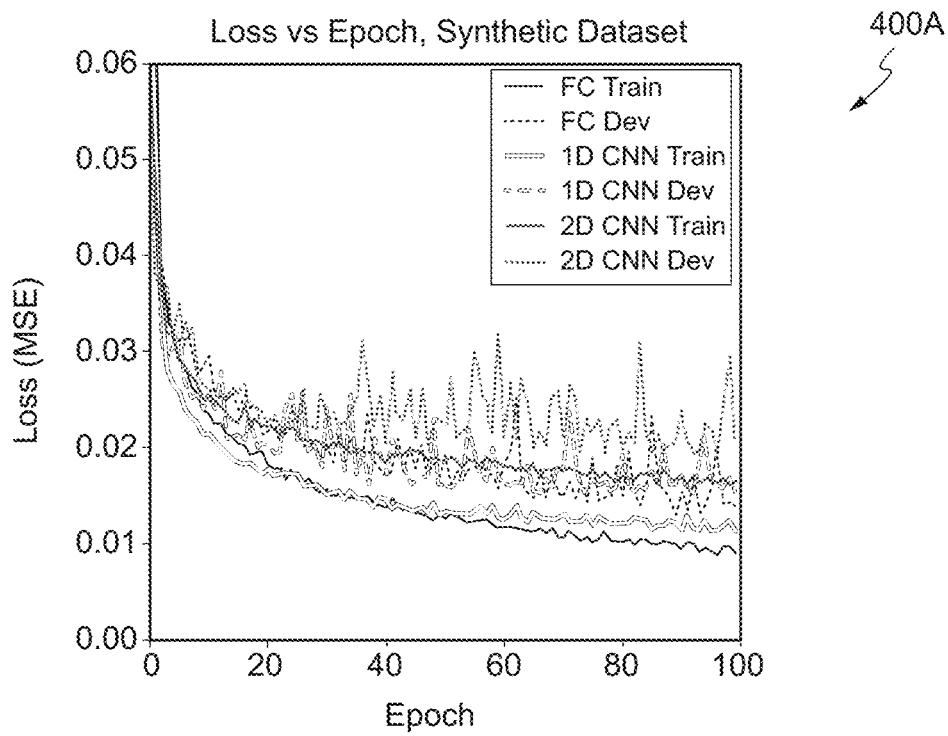
FIG. 4A shows a loss vs epoch plot of a fully connected neural network, a one-dimensional convolutional neural network, and a two-dimensional convolutional neural network being trained with VCF-level datasets, in accordance with some embodiments.
FIG. 4B shows root mean squared error (RSME) and mean absolute error (MAE) data of a fully connected neural network, a one-dimensional convolutional neural network, and a two-dimensional convolutional neural network being trained with VCF-level datasets, in accordance with some embodiments.
FIG. 4C shows root mean squared error (RSME) and mean absolute error (MAE) data for testing of a FASTQ-level dataset, in accordance with some embodiments.

C. Training and Testing of Machine-Learning Models to Estimate Tumor Purity of a Biological Sample The machine-learning models (e.g., a fully connected neural network) can be trained on the training datasets (e.g., VCF-level datasets). In some instances, the machine-learning models are first trained on the VCF-level datasets. The machine-learning models can be fitted on the "train" set, hyperparameters can be tuned based on performance on the "train" and "dev" sets, and final performance can be evaluated on the "test" set. FIG. 4A shows a loss vs epoch plot 400A of a fully connected neural network, a one-dimensional convolutional neural network, and a two-dimensional convolutional neural network being trained with VCF-level datasets, in accordance with some embodiments. The loss vs epoch plot 400A shows that performance levels of each of the trained machine-learning models increase at each epoch, thereby reaching an error value (e.g., mean-squared error) ranging between approximately 0.01 and 0.025.

FIG. 4B shows root mean squared error (RSME) and mean absolute error (MAE) data 400B of a fully connected neural network, a one-dimensional convolutional neural network, and a two-dimensional convolutional neural network being trained with VCF-level datasets, in accordance with some embodiments. All models perform comparably on the VCF-level datasets, in which the root-mean-square error values range between 0.081 (two-dimensional convolutional neural network) and 0.088 (fully connected neural network) based on the training datasets. As shown in FIGS. 4A and 4B, consistent performance across all machine-learning models trained with VCF-level train and test datasets can indicate a good fit, potentially approaching optimality for estimating tumor purity of the sample.

In some embodiments, the FASTQ-level datasets are used to improve or optimize performance of the trained machine-learning models. As it is computationally intractable to generate a large FASTQ level dataset, the machine-learning models can be trained using FASTQ-level dataset using transfer learning. Transfer learning can be performed using machine-learning models pre-trained on the VCF-level data sets. Performance of the trained machine-learning model can be evaluated using a 5-fold cross-validation strategy. In some instances, each machine-learning model can be trained on ⅘ of the training dataset and tested on ⅕ of the training dataset for each iteration. FIG. 4C shows RSME and MAE data 400C of a fully connected neural network, a one-dimensional convolutional neural network, and a two-dimensional convolutional neural network being trained with FASTQ-level datasets, in accordance with some embodiments. The RMSE and MAE data 400C indicates a comparable level of performance between a trained one-dimensional convolutional neural network (e.g., 0.057 RMSE) and a trained two-dimensional convolutional neural network (e.g., 0.067 RMSE). In addition, the RMSE and MAE data 400C indicates that the trained machine-learning models achieved lower RSME and MAE after transfer learning on the FASTQ-level dataset.

Figure 5A:
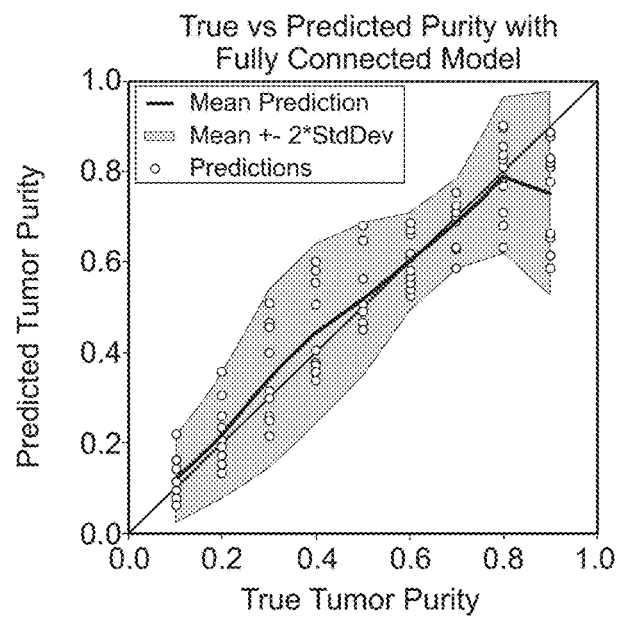
FIG. 5A shows a plot 500A comparing true tumor purity to the tumor purity predicted by a trained fully connected neural network, in accordance with some embodiments.
Figure 5B:
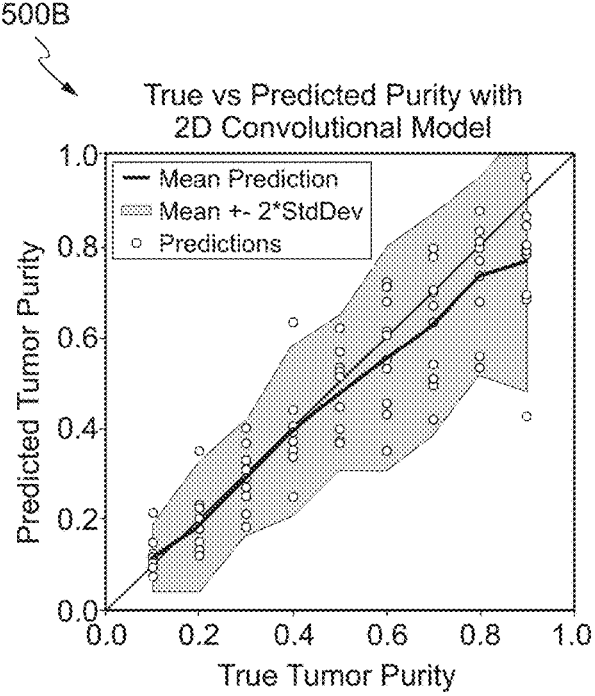
FIG. 5B shows a plot 500B comparing true tumor purity to the tumor purity predicted by a trained two-dimensional convolutional neural network, in accordance with some embodiments.
Figure 5C:
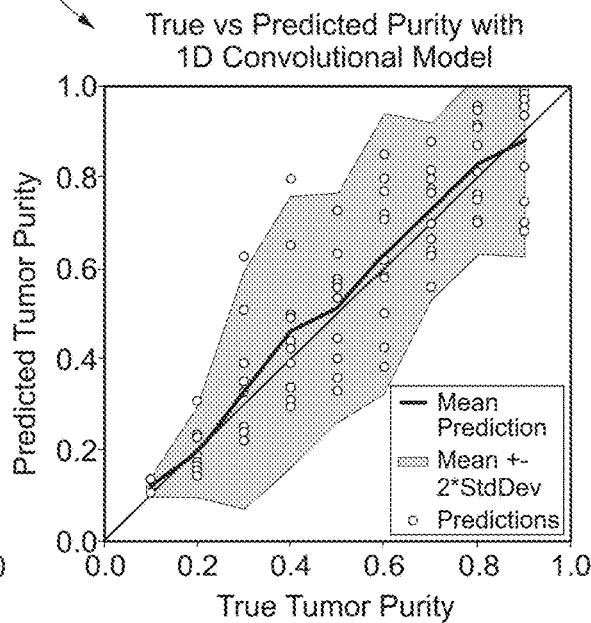
FIG. 5C shows a plot 500C comparing true tumor purity to the tumor purity predicted by a one-dimensional convolutional neural network, in accordance with some embodiments.

Performance levels of each of the trained machine-learning models were evaluated. FIG. 5A shows a plot 500A comparing true tumor purity to the tumor purity predicted by a trained fully connected network, in accordance with some embodiments. FIG. 5B shows a plot 500B comparing true tumor purity to the tumor purity predicted by a trained two-dimensional convolutional neural network, in accordance with some embodiments. FIG. 5C shows a plot 500C comparing true tumor purity to the tumor purity predicted by a one-dimensional convolutional neural network, in accordance with some embodiments. Results from each of FIGS. 5A, 5B, and 5C indicates that the trained machine-learning models achieve performance levels comparable to existing tools that require a matched normal control sample.

In some instances, the convolutional neural network models are prone to overfitting on the training dataset. For example, higher RSME and MAE values corresponding to the convolutional neural networks may not significantly improve by regularization and dropout. The tendency of these convolutional neural networks to overfit may indicate an ability of these machine-learning models to detect complex signals of tumor purity if they are trained using a larger training dataset. As such, larger and more diverse training datasets may be used to further train the machine-learning models.

In some embodiments, the trained machine-learning model is trained using training and/or test data to achieve one or more predetermined performance levels for estimating tumor purity. The one or more predetermined performance levels include the following:

an MAE of at most 1%, 2%, 3%, 4%, 5%, 6%, 7%, 8%, 9%, 10%, 11%, 12%, 13%, 14%, 15%, 16%, 17%, 18%, 19%, or 20%;

an RMSE of at most 1%, 2%, 3%, 4%, 5%, 6%, 7%, 8%, 9%, 10%, 11%, 12%, 13%, 14%, 15%, 16%, 17%, 18%, 19%, or 20%;

a precision of at least about 0.2, 0.25, 0.3, 0.35, 0.4, 0.45, 0.5, 0.55, 0.6, 0.65, 0.7, 0.75, 0.8, 0.85, 0.9, 0.95, or more. Additionally or alternatively, the trained machine-learning model is trained to estimate tumor purity with a precision of about 0.2-1.0, 0.2-0.9, 0.2-0.8, 0.2-0.7, 0.2-0.6, 0.2-0.5, 0.2-0.4, 0.2-0.3, 0.3-1.0, 0.3-0.9, 0.3-0.8, 0.3-0.7, 0.3-0.6, 0.3-0.5, 0.3-0.4, 0.4-1.0, 0.4-0.9, 0.4-0.8, 0.4-0.7, 0.4-0.6, 0.4-0.5, 0.5-1.0, 0.5-0.9, 0.5-0.8, 0.5-0.7, 0.5-0.6, 0.6-1.0, 0.6-0.9, 0.6-0.8, 0.6-0.7, 0.7-1.0, 0.7-0.9, 0.7-0.8, 0.8-1.0, 0.8-0.9, or 0.9-1.0;

a recall of at least about 0.2, 0.25, 0.3, 0.35, 0.4, 0.45, 0.5, 0.55, 0.6, 0.65, 0.7, 0.75, 0.8, 0.85, 0.9, 0.95, or more.

Additionally or alternatively, the trained machine-learning model is trained to estimate tumor purity with a recall of about 0.2-1.0, 0.2-0.9, 0.2-0.8, 0.2-0.7, 0.2-0.6, 0.2-0.5, 0.2-0.4, 0.2-0.3, 0.3-1.0, 0.3-0.9, 0.3-0.8, 0.3-0.7, 0.3-0.6, 0.3-0.5, 0.3-0.4, 0.4-1.0, 0.4-0.9, 0.4-0.8, 0.4-0.7, 0.4-0.6, 0.4-0.5, 0.5-1.0, 0.5-0.9, 0.5-0.8, 0.5-0.7, 0.5-0.6, 0.6-1.0, 0.6-0.9, 0.6-0.8, 0.6-0.7, 0.7-1.0, 0.7-0.9, 0.7-0.8, 0.8-1.0, 0.8-0.9, or 0.9-1.0; and an F1 score (e.g., a macro averaged F1 classification score) of at least about 0.2, 0.25, 0.3, 0.35, 0.4, 0.45, 0.5, 0.55, 0.6, 0.65, 0.7, 0.75, 0.8, 0.85, 0.86, 0.87, 0.88, 0.89, 0.9, 0.91, 0.92, 0.93, 0.94, 0.95, 0.96, 0.97, 0.98, 0.99, 0.995, or more. Additionally or alternatively, the trained machine-learning model is trained to estimate tumor purity with an F1 score of about 0.2-1.0, 0.2-0.99, 0.2-0.95, 0.2-0.9, 0.2-0.8, 0.2-0.7, 0.2-0.6, 0.2-0.5, 0.2-0.4, 0.2-0.3, 0.3-1.0, 0.3-0.99, 0.2-0.95, 0.3-0.9, 0.3-0.8, 0.3-0.7, 0.3-0.6, 0.3-0.5, 0.3-0.4, 0.4-1.0, 0.4-0.99, 0.4-0.95, 0.4-0.9, 0.4-0.8, 0.4-0.7, 0.4-0.6, 0.4-0.5, 0.5-1.0, 0.5-0.99, 0.5-0.95, 0.5-0.9, 0.5-0.8, 0.5-0.7, 0.5-0.6, 0.6-1.0, 0.6-0.99, 0.6-0.95, 0.6-0.9, 0.6-0.8, 0.6-0.7, 0.7-1.0, 0.7-0.99, 0.7-0.98, 0.7-0.97, 0.7-0.96, 0.7-0.95, 0.7-0.9, 0.7-0.8, 0.8-1.0, 0.8-0.99, 0.8-0.98, 0.8-0.97, 0.8-0.96, 0.8-0.95, 0.8-0.9, 0.9-1.0, 0.9-0.99, 0.9-0.98, 0.9-0.97, 0.9-0.96, or 0.9-0.95.

III. Estimating Tumor Purity

Figure 6:
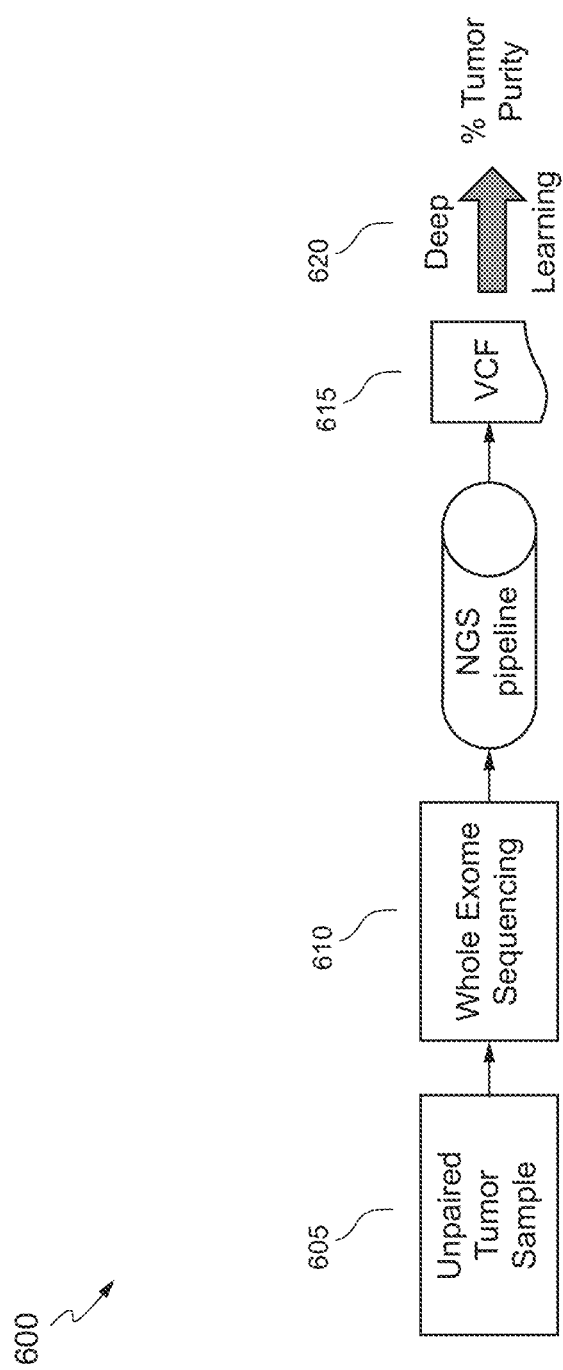
FIG. 6 illustrates an example of a schematic diagram for estimating tumor purity using a trained machine-learning model, in accordance with some embodiments.

FIG. 6 illustrates an example of a schematic diagram 600 for estimating tumor purity using a trained machine-learning model, in accordance with some embodiments. Tumor purity from sequencing of an unmatched biological sample can be estimated using a trained machine-learning model (e.g., a regression model). In some instances, a deep neural network is used to estimate tumor purity from an allele fraction distribution (e.g., a B-allele frequency distribution) of nucleotide-sequence variants in an unpaired biological sample. A regression model can be used to predict tumor purity from the B-allele frequency (BAF) of whole exome sequencing data.

In block 605, an unmatched tumor sample can be obtained from a cancer patient (i.e., without a matched normal sample). In block 610, DNA is extracted from the tumor sample, processed, and subjected to whole exome sequencing. In some instances, sequencing reads are subjected to quality control processing (e.g., via FastQC) to provide FASTQ files. FASTQ files are aligned to a reference genome to generate a BAM files.

In block 615, GATK HaplotypeCaller may be used to call variants from the BAM files and generate VCF files containing the variant information. Heterozygous sites in the sample exome can be identified, and VCF files can be filtered to obtain reference and alternate read depth for all heterozygous sites. This information is used to compute B allele frequency (BAF). Normalized BAF distribution is computed for heterozygous sites across the exome.

In block 620, a trained machine-learning model can be used to estimate tumor purity from the normalized BAF distribution. The trained machine-learning model can thus generate an accurate estimate of tumor purity despite the lack of a matched normal sample.

A. Subjects and Samples

To estimate tumor purity, nucleic acid sequence data that represent a plurality of nucleic acid molecules can be obtained from a biological sample of a subject. The subject can be human. The subject may be a male or a female. The subject may be a fetus, infant, child, adolescent, teenager or adult. The subject may be patients of any age. For example, the subject may be a patient of less than about 10 years old. For example, the subject may be a patient of at least about 0, 5, 10, 20, 30, 40, 50, 60, 70, 80, 90, or 100 years old. The subject can be a patient or other individual undergoing a treatment regimen, or being evaluated for a treatment regimen (e.g., cancer therapy). However, in some instances, the subject is not undergoing a treatment regimen.

In some instances, the subjects may be mammals or non-mammals. In some instances, the subjects are a mammal, such as, a human, non-human primate (e.g., apes, monkeys, chimpanzees), cat, dog, rabbit, goat, horse, cow, pig, rodent, mouse, SCID mouse, rat, guinea pig, or sheep. In some embodiments, species variants or homologs of these genes are used in a non-human animal model. Species variants may be genes of different species having the greatest sequence identity and similarity in functional properties to one another. Many of such species variants human genes may be listed in a Swiss-Prot database.

Certain embodiments may include obtaining a sample from a subject, such as a human subject. In some instances, a clinical specimen from a patient is obtained. For example, blood may be drawn from a patient. Certain embodiments may include specifically detecting, profiling, or quantitating molecules (e.g., nucleic acids, DNA, RNA, etc.) that are within the biological samples.

The sample may be a tissue sample or a bodily fluid. In some instances, the sample is a tissue sample or an organ sample, such as a biopsy. In some instances, the sample includes cancerous cells. In some instances, the sample includes cancerous and normal cells. In some instances, the sample is a tumor biopsy. The bodily fluid may be sweat, saliva, tears, urine, blood, menses, semen, and/or spinal fluid. In some instances, the sample is a blood sample. The sample may include one or more peripheral blood lymphocytes. The sample may be a whole blood sample. The blood sample may be a peripheral blood sample. In some instances, the sample includes peripheral blood mononuclear cells (PBMCs); in some cases, the sample includes peripheral blood lymphocytes (PBLs). The sample may be a serum sample.

The sample may be obtained using any method that can provide a sample suitable for the analytical methods described herein. The sample may be obtained by a non-invasive method such as a throat swab, buccal swab, bronchial lavage, urine collection, scraping of the skin or cervix, swabbing of the cheek, saliva collection, feces collection, menses collection, or semen collection. The sample may be obtained by a minimally-invasive method such as a blood draw. The sample may be obtained by venipuncture. In other instances, the sample is obtained by an invasive procedure including but not limited to: biopsy, alveolar or pulmonary lavage, or needle aspiration. The method of biopsy may include surgical biopsy, incisional biopsy, excisional biopsy, punch biopsy, shave biopsy, or skin biopsy. The sample may be formalin fixed sections. The method of needle aspiration may further include fine needle aspiration, core needle biopsy, vacuum assisted biopsy, or large core biopsy. In some instances, multiple samples may be obtained by the methods herein to ensure a sufficient amount of biological material. In some instances, the sample is not obtained by biopsy. In some instances, the sample is not a kidney biopsy.

Methods of the disclosure can be used to estimate tumor purity in samples including at least about 1%, 5%, 10%, 15%, 20%, 25%, 30%, 35%, 40%, 45%, 50%, 55%, 60%, 65%, 70%, 75%, 80%, 85%, 90%, 95%, or more tumor cells.

In some embodiments, methods of the disclosure can be used to estimate tumor purity in samples including at most about 10%, 15%, 20%, 25%, 30%, 35%, 40%, 45%, 50%, 55%, 60%, 65%, 70%, 75%, 80%, 85%, 90%, 95%, or more tumor cells.

B. Generating Nucleic Acid Sequencing Data

In some embodiments, the sample is processed to obtain nucleic acid sequence data. "Nucleic acid" or "nucleic acid molecules" can correspond to a polymeric form of nucleotides of any length, either ribonucleotides, deoxyribonucleotides or peptide nucleic acids (PNAs), that include purine and pyrimidine bases, or other natural, chemically or biochemically modified, non-natural, or derivatized nucleotide bases. The backbone of the polynucleotide can include sugars and phosphate groups, as may typically be found in RNA or DNA, or modified or substituted sugar or phosphate groups. A polynucleotide may include modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired. The nucleic acid molecule may be a DNA molecule. The nucleic acid molecule may be an RNA molecule.

The sample processing includes nucleic acid sample processing and subsequent nucleic acid sample sequencing. Some or all of the biological sample may be sequenced to provide the nucleic acid sequence data, which may be stored or otherwise maintained in an electronic, magnetic or optical storage location. The sequence information may be analyzed with the aid of a computer processor, and the analyzed sequence information may be stored in an electronic storage location. The electronic storage location may include a pool or collection of sequence information and analyzed sequence information generated from the nucleic acid sample. In some embodiments, the biological sample is retrieved from a subject that has or is suspected of having cancer.

In some embodiments, nucleic acid sequencing data are generated from pure tumor and pure normal samples. Matched pair cell lines can be obtained from another source (e.g., American Type Culture Collection). Each matched pair may include a tumor cell line and a normal cell line from the same subject. The cell lines can be cultured and expanded in vitro to obtain a suitable number of cells for DNA extraction. DNA is extracted, processed, and subjected to whole exome or whole genome sequencing. Sequence reads can be subjected to quality control processing (e.g., via FastQC) to provide FASTQ files.

In some instances, the nucleic acid sequence data is generated using whole genome sequencing. In some instances, the whole genome sequencing is used to identify variants in a person. In some instances, sequencing can include deep sequencing over a fraction of the genome. For example, the fraction of the genome may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. In some instances, the genome may be sequenced over 1 million, 2 million, 3 million, 4 million, 5 million, 6 million, 7 million, 8 million, 9 million, 10 million or more than 10 million bases or base pairs. In some instances, the genome may be sequenced over an entire exome (e.g., whole exome sequencing). In some instances, the deep sequencing may include acquiring multiple reads over the fraction of the genome. For example, acquiring multiple reads may include at least 2, 3, 4, 5, 6, 7, 8, 9, 10, 20, 30, 40, 50, 60, 70, 80, 90, 100, 200, 300, 400, 500, 600, 700, 800, 900, 1000, 10,000 reads or more than 10,000 reads over the fraction of the genome.

In some instances, generating the nucleic acid sequence data includes detecting low allelic fractions by deep sequencing. In some instances, the deep sequencing is done by next generation sequencing. In some instances, the deep sequencing is performed by avoiding error-prone regions. In some instances, the error-prone regions may include regions of near sequence duplication, regions of unusually high or low % GC, regions of near homopolymers, di- and trinucleotide, and regions of near other short repeats. In some instances, the error-prone regions may include regions that lead to DNA sequencing errors (e.g., polymerase slippage in homopolymer sequences).

In some instances, generating the nucleic acid sequence data includes conducting one or more sequencing reactions on one or more nucleic acid molecules in a sample. Certain embodiments may include conducting 1 or more, 2 or more, 3 or more, 4 or more, 5 or more, 6 or more, 7 or more, 8 or more, 9 or more, 10 or more, 15 or more, 20 or more, 30 or more, 40 or more, 50 or more, 60 or more, 70 or more, 80 or more, 90 or more, 100 or more, 200 or more, 300 or more, 400 or more, 500 or more, 600 or more, 700 or more, 800 or more, 900 or more, or 1000 or more sequencing reactions on one or more nucleic acid molecules in a sample. The sequencing reactions may be run simultaneously, sequentially, or a combination thereof. The sequencing reactions may include whole genome sequencing or exome sequencing. The sequencing reactions may include Maxim-Gilbert, chain-termination or high-throughput systems. Alternatively, or additionally, the sequencing reactions may include Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, VisiGen Biotechnologies approach, or a combination thereof. Alternatively, or additionally, the sequencing reactions can include one or more sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, MA). Sequencing reactions may also include electron microscopy or a chemical-sensitive field effect transistor (chemFET) array. In some aspects of the disclosure, sequencing reactions include capillary sequencing, next generation sequencing, Sanger sequencing, sequencing by synthesis, sequencing by ligation, sequencing by hybridization, single molecule sequencing, or a combination thereof. Sequencing by synthesis may include reversible terminator sequencing, processive single molecule sequencing, sequential flow sequencing, or a combination thereof. Sequential flow sequencing may include pyrosequencing, pH-mediated sequencing, semiconductor sequencing, or a combination thereof.

In some instances, generating the nucleic acid sequence data includes conducting at least one long read sequencing reaction and at least one short read sequencing reaction. The long read sequencing reaction and/or short read sequencing reaction may be conducted on at least a portion of a subset of nucleic acid molecules. The long read sequencing reaction and/or short read sequencing reaction may be conducted on at least a portion of two or more subsets of nucleic acid molecules. Both a long read sequencing reaction and a short read sequencing reaction may be conducted on at least a portion of one or more subsets of nucleic acid molecules.

Sequencing of the one or more nucleic acid molecules or subsets thereof may include at least about 5; 10; 15; 20; 25; 30; 35; 40; 45; 50; 60; 70; 80; 90; 100; 200; 300; 400; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 25,000; 50,000; 75,000; 100,000; 250,000; 500,000; 750,000; 10,000,000; 25,000,000; 50,000,000; 100,000,000; 250,000,000; 500,000,000; 750,000,000; 1,000,000,000 or more sequencing reads.

Sequencing reactions may include sequencing at least about 50; 60; 70; 80; 90; 100; 110; 120; 130; 140; 150; 160; 170; 180; 190; 200; 210; 220; 230; 240; 250; 260; 270; 280; 290; 300; 325; 350; 375; 400; 425; 450; 475; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 20,000; 30,000; 40,000; 50,000; 60,000; 70,000; 80,000; 90,000; 100,000 or more bases or base pairs of one or more nucleic acid molecules. Sequencing reactions may include sequencing at least about 50; 60; 70; 80; 90; 100; 110; 120; 130; 140; 150; 160; 170; 180; 190; 200; 210; 220; 230; 240; 250; 260; 270; 280; 290; 300; 325; 350; 375; 400; 425; 450; 475; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 20,000; 30,000; 40,000; 50,000; 60,000; 70,000; 80,000; 90,000; 100,000 or more consecutive bases or base pairs of one or more nucleic acid molecules.

In some instances, the sequencing technique generates at least 100 reads per run, at least 200 reads per run, at least 300 reads per run, at least 400 reads per run, at least 500 reads per run, at least 600 reads per run, at least 700 reads per run, at least 800 reads per run, at least 900 reads per run, at least 1000 reads per run, at least 5,000 reads per run, at least 10,000 reads per run, at least 50,000 reads per run, at least 100,000 reads per run, at least 500,000 reads per run, or at least 1,000,000 reads per run. Alternatively, the sequencing technique generates at least 1,500,000 reads per run, at least 2,000,000 reads per run, at least 2,500,000 reads per run, at least 3,000,000 reads per run, at least 3,500,000 reads per run, at least 4,000,000 reads per run, at least 4,500,000 reads per run, or at least 5,000,000 reads per run.

In some instances, the sequencing technique generates at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110, at least about 120 base pairs per read, at least about 150 base pairs, at least about 200 base pairs, at least about 250 base pairs, at least about 300 base pairs, at least about 350 base pairs, at least about 400 base pairs, at least about 450 base pairs, at least about 500 base pairs, at least about 550 base pairs, at least about 600 base pairs, at least about 700 base pairs, at least about 800 base pairs, at least about 900 base pairs, or at least about 1,000 base pairs per read. Additionally or alternatively, the sequencing technique can generate long sequencing reads. In some instances, the sequencing technique can generate at least about 1,200 base pairs per read, at least about 1,500 base pairs per read, at least about 1,800 base pairs per read, at least about 2,000 base pairs per read, at least about 2,500 base pairs per read, at least about 3,000 base pairs per read, at least about 3,500 base pairs per read, at least about 4,000 base pairs per read, at least about 4,500 base pairs per read, at least about 5,000 base pairs per read, at least about 6,000 base pairs per read, at least about 7,000 base pairs per read, at least about 8,000 base pairs per read, at least about 9,000 base pairs per read, at least about 10,000 base pairs per read, 20,000 base pairs per read, 30,000 base pairs per read, 40,000 base pairs per read, 50,000 base pairs per read, 60,000 base pairs per read, 70,000 base pairs per read, 80,000 base pairs per read, 90,000 base pairs per read, or 100,000 base pairs per read.

High-throughput sequencing systems may allow detection of a sequenced nucleotide immediately after or upon its incorporation into a growing strand, i.e., detection of sequence in real time or substantially real time. In some instances, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120, at least 150, at least 200, at least 250, at least 300, at least 350, at least 400, at least 450, or at least 500 bases per read. Sequencing can be performed using nucleic acids described herein such as genomic DNA, cDNA derived from RNA transcripts or RNA as a template.

C. Identification of Nucleotide-Sequence Variants

To estimate tumor purity of a biological sample, a B Allele Frequency (BAF) for the biological sample can be determined. To determine the BAF, a set of genomic regions can be identified, in which each of the set of genomic regions may include nucleotide-sequence variants relative to a corresponding genomic region of the reference genome. To determine the set of genomic regions, the nucleic acid sequence data can be aligned to a reference genome. For example, the FASTQ files, which correspond to the nucleic acid sequence data, can be aligned to a reference genome to generate one or more BAM files. The one or more BAM files can be processed by another module (e.g., GATK HaplotypeCaller) to identify the set of genomic regions. In some instances, VCF files containing the set of genomic regions are generated. Additionally or alternatively, the VCF files can be obtained for matched pair cell lines. The VCF files may identify the set of genomic regions having the nucleotide-sequence variants based on a comparison of the nucleic acid sequence data and the reference genome.

Certain embodiments may include nucleic acid molecules including one or more genomic regions. Certain embodiments may include nucleic acid molecules including one or more sets of genomic regions. The one or more genomic regions may include one or more genomic region features. The genomic region features may include an entire genome or a portion thereof. The genomic region features may include an entire exome or a portion thereof. The genomic region features may include one or more sets of genes. The genomic region features may include one or more genes.

The genomic region features may include one or more sets of regulatory elements. The genomic region features may include one or more regulatory elements.

The genomic region features may include a set of polymorphisms. The genomic region features may include one or more polymorphisms. The genomic region feature may relate to the GC content, complexity, and/or mappablity of one or more nucleic acid molecules. The genomic region features may include one or more simple tandem repeats (STRs), unstable expanding repeats, segmental duplications, single and paired read degenerative mapping scores, GRCh37 patches, or a combination thereof. The genomic region features may include one or more low mean coverage regions from whole genome sequencing (WGS), zero mean coverage regions from WGS, validated compressions, or a combination thereof. The genomic region features may include one or more alternate or non-reference sequences. The genomic region features may include one or more gene phasing and reassembly genes. In some aspects of the disclosure, the one or more genomic region features are not mutually exclusive. For example, a genomic region feature including an entire genome or a portion thereof can overlap with an additional genomic region feature such as an entire exome or a portion thereof, one or more genes, one or more regulatory elements, etc. Alternatively, the one or more genomic region futures are mutually exclusive. For example, a genomic region including the noncoding portion of an entire genome would not overlap with a genomic region feature such as an exome or portion thereof or the coding portion of a gene. Alternatively, or additionally, the one or more genomic region features are partially exclusive or partially inclusive. For example, a genomic region including an entire exome or a portion thereof can partially overlap with a genomic region including an exon portion of a gene. However, the genomic region including the entire exome or portion thereof would not overlap with the genomic region including the intron portion of the gene. Thus, a genomic region feature including a gene or portion thereof may partially exclude and/or partially include a genomic region feature including an entire exome or portion thereof.

Certain embodiments may include nucleic acid samples or molecules including one or more genomic regions, wherein at least one of the one or more genomic regions includes a genomic region feature including an entire genome or portion thereof. The entire genome or portion thereof may include one or more coding portions of the genome, one or more noncoding portions of the genome, or a combination thereof. The coding portion of the genome may include one or more coding portions of a gene encoding for one or more proteins. The one or more coding portions of the genome may include an entire exome or a portion thereof. Alternatively, or additionally, the one or more coding portions of the genome may include one or more exons.

The one or more noncoding portions of the genome may include one or more noncoding molecules or a portion thereof. The noncoding molecules may include one or more noncoding RNA, one or more regulatory elements, one or more introns, one or more pseudogenes, one or more repeat sequences, one or more transposons, one or more viral elements, one or more telomeres, a portion thereof, or a combination thereof. The noncoding RNAs may be functional RNA molecules that are not translated into protein. Examples of noncoding RNAs include, but are not limited to, ribosomal RNA, transfer RNA, piwi-interacting RNA, microRNA, siRNA, shRNA, snoRNA, sncRNA, and lncRNA. Pseudogenes may be related to known genes and are typically no longer expressed. Repeat sequences may include one or more tandem repeats, one or more interspersed repeats, or a combination thereof. Tandem repeats may include one or more satellite DNA, one or more minisatellites, one or more microsatellites, or a combination thereof.

Interspersed repeats may include one or more transposons. Transposons may be mobile genetic elements. Mobile genetic elements are often able to change their position within the genome. Transposons may be classified as class I transposable elements (class I TEs) or class II transposable elements (class II TEs). Class I TEs (e.g., retrotransposons) may often copy themselves in two stages, first from DNA to RNA by transcription, then from RNA back to DNA by reverse transcription. The DNA copy may then be inserted into the genome in a new position. Class I TEs may include one or more long terminal repeats (LTRs), one or more long interspersed nuclear elements (LINEs), one or more short interspersed nuclear elements (SINEs), or a combination thereof. Examples of LTRs include, but are not limited to, human endogeneous retroviruses (HERVs), medium reiterated repeats 4 (MER4), and retrotransposon. Examples of LINEs include, but are not limited to, LINE1 and LINE2. SINEs may include one or more Alu sequences, one or more mammalian-wide interspersed repeat (MIR), or a combination thereof. Class II TEs (e.g., DNA transposons) often do not involve an RNA intermediate. The DNA transposon is often cut from one site and inserted into another site in the genome. Alternatively, the DNA transposon is replicated and inserted into the genome in a new position. Examples of DNA transposons include, but are not limited to, MER1, MER2, and mariners. Viral elements may include one or more endogenous retrovirus sequences. Telomeres are often regions of repetitive DNA at the end of a chromosome.

Certain embodiments may include nucleic acid samples or subsets of nucleic acid molecules including one or more genomic regions, wherein at least one of the one or more genomic regions includes a genomic region feature including an entire exome or portion thereof. The exome is often the part of the genome formed by exons. The exome may be formed by untranslated regions (UTRs), splice sites and/or intronic regions. The entire exome or portion thereof may include one or more exons of a protein coding gene. The entire exome or portion thereof may include one or more untranslated regions (UTRs), splice sites, and introns.

Certain embodiments may include nucleic acid samples or molecules including one or more genomic regions, wherein at least one of the one or more genomic regions includes a genomic region feature including a gene or portion thereof. Typically, a gene includes stretches of nucleic acids that code for a polypeptide or a functional RNA. A gene may include one or more exons, one or more introns, one or more untranslated regions (UTRs), or a combination thereof. Exons are often coding sections of a gene, transcribed into a precursor mRNA sequence, and within the final mature RNA product of the gene. Introns are often noncoding sections of a gene, transcribed into a precursor mRNA sequence, and removed by RNA splicing. UTRs may refer to sections on each side of a coding sequence on a strand of mRNA. A UTR located on the 5' side of a coding sequence may be called the 5' UTR (or leader sequence). A UTR located on the 3' side of a coding sequence may be called the 3' UTR (or trailer sequence). The UTR may contain one or more elements for controlling gene expression. Elements, such as regulatory elements, may be located in the 5' UTR. Regulatory sequences, such as a polyadenylation signal, binding sites for proteins, and binding sites for miRNAs, may be located in the 3' UTR. Binding sites for proteins located in the 3' UTR may include, but are not limited to, selenocysteine insertion sequence (SECIS) elements and AU-rich elements (AREs). SECIS elements may direct a ribosome to translate the codon UGA as selenocysteine rather than as a stop codon. AREs are often stretches consisting primarily of adenine and uracil nucleotides, which may affect the stability of a mRNA.

Certain embodiments may include nucleic acid samples or subsets of nucleic acid molecules including one or more genomic regions, wherein at least one of the one or more genomic regions includes a genomic region feature including a set of genes. The sets of genes may include, but are not limited to, Mendel DB Genes, Human Gene Mutation Database (HGMD) Genes, Cancer Gene Census Genes, Online Mendelian Inheritance in Man (OMIM) Mendelian Genes, HGMD Mendelian Genes, and human leukocyte antigen (HLA) Genes. The set of genes may have one or more known Mendelian traits, one or more known disease traits, one or more known drug traits, one or more known biomedically interpretable variants, or a combination thereof. A Mendelian trait may be controlled by a single locus and may show a Mendelian inheritance pattern. A set of genes with known Mendelian traits may include one or more genes encoding Mendelian traits including, but not limited to, ability to taste phenylthiocarbamide (dominant), ability to smell (bitter almond-like) hydrogen cyanide (recessive), albinism (recessive), brachydactyly (shortness of fingers and toes), and wet (dominant) or dry (recessive) earwax. A disease trait cause or increase risk of disease and may be inherited in a Mendelian or complex pattern. A set of genes with known disease traits may include one or more genes encoding disease traits including, but not limited to, Cystic Fibrosis, Hemophilia, and Lynch Syndrome.

A drug trait may alter metabolism, optimal dose, adverse reactions and side effects of one or more drugs or family of drugs. A set of genes with known drug traits may include one or more genes encoding drug traits including, but are not limited to, CYP2D6, UGT1A1 and ADRB1. A biomedically interpretable variant may be a polymorphism in a gene that is associated with a disease or indication. A set of genes with known biomedically interpretable variants may include one or more genes encoding biomedically interpretable variants including, but not limited to, cystic fibrosis (CF) mutations, muscular dystrophy mutations, p53 mutations, Rb mutations, cell cycle regulators, receptors, and kinases. Alternatively, or additionally, a set of genes with known biomedically interpretable variants may include one or more genes associated with Huntington's disease, cancer, cystic fibrosis, muscular dystrophy (e.g., Duchenne muscular dystrophy).

Certain embodiments may include nucleic acid samples or molecules including one or more genomic regions, wherein at least one of the one or more genomic regions includes a genomic region feature including a regulatory element or a portion thereof. Regulatory elements may be cis-regulatory elements or trans-regulatory elements. Cis-regulatory elements may be sequences that control transcription of a nearby gene. Cis-regulatory elements may be located in the 5' or 3' untranslated regions (UTRs) or within introns. Trans-regulatory elements may control transcription of a distant gene. Regulatory elements may include one or more promoters, one or more enhancers, or a combination thereof. Promoters may facilitate transcription of a particular gene and may be found upstream of a coding region. Enhancers may exert distant effects on the transcription level of a gene.

Certain embodiments may include nucleic acid samples or subsets of nucleic acid molecules including one or more genomic regions, wherein at least one of the one or more genomic regions includes a genomic region feature including a polymorphism or a portion thereof. Generally, a polymorphism refers to a mutation in a genotype. A polymorphism can be a germline variant or a somatic variant. A polymorphism may include one or more base changes, an insertion, a repeat, or a deletion of one or more bases. Copy number variants (CNVs), transversions and other rearrangements are also forms of genetic variation. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are a form of polymorphisms. In some aspects of the disclosure, one or more polymorphisms include one or more single nucleotide variations, inDels, small insertions, small deletions, structural variant junctions, variable length tandem repeats, flanking sequences, or a combination thereof. The one or more polymorphisms may be located within a coding and/or non-coding region. The one or more polymorphisms may be located within, around, or near a gene, exon, intron, splice site, untranslated region, or a combination thereof. The one or more polymorphisms may be may span at least a portion of a gene, exon, intron, untranslated region.

Certain embodiments may include nucleic acid samples or molecules including one or more genomic regions, wherein at least one of the one or more genomic regions includes a genomic region feature including one or more simple tandem repeats (STRs), unstable expanding repeats, segmental duplications, single and paired read degenerative mapping scores, GRCh37 patches, or a combination thereof. The one or more STRs may include one or more homopolymers, one or more dinucleotide repeats, one or more trinucleotide repeats, or a combination thereof. The one or more homopolymers may be about 7, 8, 9, 10, 11, 12, 13, 14, 15, 16, 17, 18, 19, 20 or more bases or base pairs. The dinucleotide repeats and/or trinucleotide repeats may be about 15, 16, 17, 18, 19, 20, 21, 22, 23, 24, 25, 26, 27, 28, 29, 30, 35, 40, 45, 50 or more bases or base pairs. The single and paired read degenerative mapping scores may be based on or derived from alignability of 100mers by GEM from ENCODE/CRG (Guigo), alignability of 75mers by GEM from ENCODE/CRG (Guigo), 100 base pair box car average for signal mappability, max of locus and possible pairs for paired read score, or a combination thereof.

The genomic region features may include one or more low mean coverage regions from whole genome sequencing (WGS), zero mean coverage regions from WGS, validated compressions, or a combination thereof. The low mean coverage regions from WGS may include regions generated from Illumina v3 chemistry, regions below the first percentile of Poission distribution based on mean coverage, or a combination thereof. The Zero mean coverage regions from WGS may include regions generated from Illumina v3 chemistry. The validated compressions may include regions of high mapped depth, regions with two or more observed haplotypes, regions expected to be missing repeats in a reference, or a combination thereof. The genomic region features may include one or more alternate or non-reference sequences. The one or more alternate or non-reference sequences may include known structural variant junctions, known insertions, known deletions, alternate haplotypes, or a combination thereof. The genomic region features may include one or more gene phasing and reassembly genes. Examples of phasing and reassembly genes include, but are not limited to, one or more major histocompatibility complexes, blood typing, and amylase gene family. The one or more major histocompatibility complexes may include one or more HLA Class I, HLA Class II, or a combination thereof. The one or more HLA class I may include HLA-A, HLA-B, HLA-C, or a combination thereof. The one or more HLA class II may include HLA-DP, HLA-DM, HLA-DOA, HLA-DOB, HLA-DQ, HLA-DR, or a combination thereof. The blood typing genes may include ABO, RHD, RHCE, or a combination thereof.

Certain embodiments may include nucleic acid samples or molecules including one or more genomic regions, wherein at least one of the one or more genomic regions includes a genomic region feature related to the GC content of one or more nucleic acid molecules. The GC content may refer to the GC content of a nucleic acid molecule. Alternatively, the GC content may refer to the GC content of one or more nucleic acid molecules and may be referred to as the mean GC content. As used herein, the terms "GC content" and "mean GC content" may be used interchangeably. The GC content of a genomic region may be a high GC content. Typically, a high GC content refers to a GC content of greater than or equal to about 65%, 70%, 75%, 80%, 85%, 90%, 95%, 97%, or more. In some aspects of the disclosure, a high GC content may refer to a GC content of greater than or equal to about 70%. The GC content of a genomic region may be a low GC content. Typically, a low GC content refers to a GC content of less than or equal to about 65%, 60%, 55%, 50%, 45%, 40%, 35%, 30%, 25%, 20%, 15%, 10%, 5%, 2%, or less.

Certain embodiments may include nucleic acid samples or molecules including one or more genomic regions, wherein at least one of the one or more genomic regions includes a genomic region feature related to the complexity of one or more nucleic acid molecules. The complexity of a nucleic acid molecule may refer to the randomness of a nucleotide sequence. Low complexity may refer to patterns, repeats and/or depletion of one or more species of nucleotide in the sequence.

Certain embodiments may include nucleic acid samples or molecules including one or more genomic regions, wherein at least one of the one or more genomic regions includes a genomic region feature related to the mappablity of one or more nucleic acid molecules. The mappability of a nucleic acid molecule may refer to uniqueness of its alignment to a reference sequence. A nucleic acid molecule with low mappability may have poor alignment to a reference sequence.

D. Calculation of BAF Distribution

For each genomic region of the set of genomic regions, a B-allele frequency (BAF) can be determined. The BAF refers to a normalized measure of the allelic intensity ratio of two alleles (A and B). A BAF of 100 or 0 indicates the complete absence of one of the two alleles (e.g. AA or BB). For example, a BAF for a given genomic region can be 100 when both chromosomes of a sample contain a nucleotide-sequence variant relative to the reference genome. Thus, the variant allele should be present in close to 100% of reads for that sample. In some instances, the BAF distribution is normalized to produce a density plot such that the area under the curve sums to 1. Specifically, a histogram of the BAF for all variants is produced, the area of this histogram is computed, and each bin of the histogram is divided by the computed area.

For heterozygous alleles in the sample, a variant will be present in a subset of sequence reads. Thus, a BAF of 50 indicates the equal presence of both alleles (e.g. AB). A BAF of 0, 50, or 100 can be expected for normal samples in the absence of copy number variation. In tumor samples, however, the mutations can alter the BAF values. For example, a copy number event that duplicates a B allele can lead to a B allele frequency of-67%. In another example, when only one chromosome contains the variant, the variant allele should be present in close to 50% of reads for that sample. Random variation inherent to the data generation process introduces noise, causing the observed BAF measurements to deviate from the idealized values for a given copy number in both tumor an normal samples.

In some instances, a subset of genomic regions corresponding to heterozygous sites in the biological sample (e.g., exome sample) are identified, and allele frequency for each of the subset of genomic regions is quantified. The VCF files can thus be filtered to obtain reference and alternate read depth for all heterozygous sites having the nucleotide-sequence variants. Such information can be used to compute BAF for each genomic region of the subset of genomic regions that have heterozygosity.

Based on the determined BAF for each of the set of genomic regions, a normalized BAF distribution can be computed. The BAF distribution can indicate an absolute quantity, a percentage, and/or or a normalized quantity corresponding to BAF of each genomic region of the set of genomic regions. In some instances, the normalized BAF distribution is determined from BAFs corresponding to the subset of genomic regions (e.g., heterozygous sites across the exome). Because the BAF values are typically between 0 and 100, the normalized BAF distribution may include up to 101 BAF values, each of which indicating a corresponding normalized frequency. Additionally or alternatively, the normalized BAF distribution can be modified such that the corresponding BAF values can be populated into a predetermined number of bins. For example, each bin may correspond to a non-overlapping range of BAF values (e.g., 1-9, 10-19), and the BAF values can be assigned to the corresponding bin. The BAF distribution may then be determined based on the values corresponding to each predetermined bin.

FIGS. 7A-7E provide examples of plotted BAF distributions in accordance with some embodiments. For both FIGS. 7A and 7B, the x-axis represents BAF values ranging from 0% (homozygous for A allele) to 100% (homozygous for B allele). As explained above, a BAF of 50 indicates heterozygosity, which corresponds to an equal presence of both alleles (e.g. AB). A BAF of 0, 50, or 100 can be expected for normal samples. In tumor samples, however, the mutations can alter the BAF values. For example, a copy number event that duplicates a B allele can lead to a B allele frequency of-67%. The y-axis represents normalized frequency values corresponding to each BAF value on the x-axis. The normalized frequency values may identify a number of genomic regions that correspond to a particular BAF value. For example, the normalized frequency for a BAF of 50% can be a value above 4.

FIG. 7A is a histogram of B allele frequency from heterozygous sites in a chromosome of a pure normal sample. The histogram exhibits a normal distribution, with most observed B allele frequencies falling close to 50%. FIG. 7B is a histogram of B allele frequency from heterozygous sites in a pure tumor sample. The histogram exhibits an altered distribution, with more observations of B allele frequencies that fall further from 50%. As shown in FIG. 7B, it can be shown that an increased number of somatic mutations may have caused the BAF frequencies to be modified from 50%.

FIG. 7C is a heat map, where each row represents a BAF distribution from a chromosome in a pure normal sample. The heat map exhibits a normal distribution, with most observed B allele frequencies falling close to 50%. FIG. 7E is a heat map, where each row represents a BAF distribution from a chromosome in a pure tumor sample. The heat map exhibits an altered distribution, with more observations of B allele frequencies that fall further from 50%. FIG. 7D is a heat map from a sample that is 50% normal and 50% tumor. The heat map exhibits an intermediate distribution that is falls in between the distributions exhibited in FIG. 7C and FIG. 7E.

E. Classification of Pure Tumor and Pure Normal Samples Using BAF

In some instances, BAF features of a biological sample are used to classify the biological sample as being normal or having tumor. For example, normalized BAF distribution can be computed at heterozygous sites across the exome for multiple pure tumor and pure normal samples. The pure tumor and pure normal samples can be classified using logistic regression with the whole exome BAF features.

Figure 8:
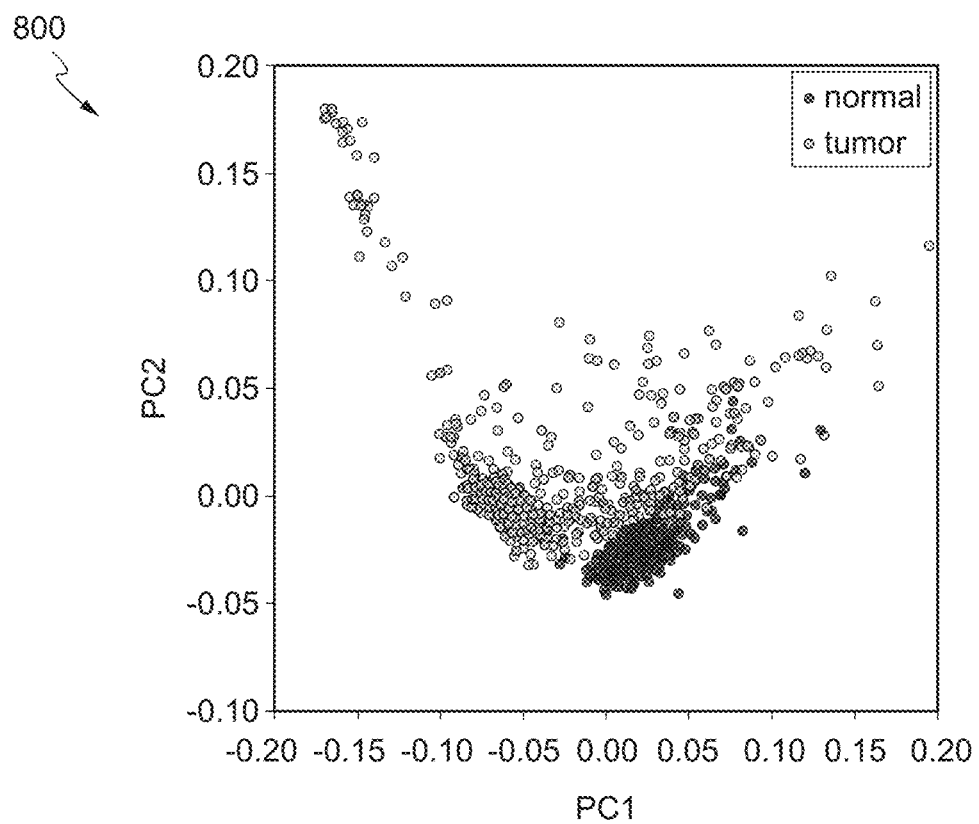
FIG. 8 shows a plot 800 of the first two principal components for classifying a biological sample using B-allele frequency features, in accordance with some embodiments.

FIG. 8 shows a plot 800 of the first two principal components (PC1 and PC2) for classifying a biological sample using B-allele frequency features, in accordance with some embodiments. In FIG. 8, the first two principal components show near linear separability of tumor and normal, indicating that BAF features may be suitable for estimating tumor content of a sample. In addition, it can be demonstrated that pure tumor and pure normal samples can be classified using logistic regression with the whole exome BAF features.

F. Estimation of Tumor Purity Based on BAF Distribution

The BAF distribution of the biological sample can be processed using a trained machine-learning model to estimate a metric identifying tumor purity of the biological sample. In some embodiments, the trained machine-learning model includes a fully connected neural network. The fully connected neural network may include fully connected layers with Rectified Linear Unit (ReLU) activation functions. In some embodiments, output activation function of the fully connected neural network is a sigmoid function. A loss function of the fully connected neural network can be configured to generate a mean squared error (MSE). In some embodiments, the fully connected neural network is tuned via hyperparameter search using random sampling with a linear search over layers, a linear search over size, a logarithmic search over learning rate, or a combination thereof.

In some instances, the trained machine-learning model includes a one-dimensional convolutional neural network. The one-dimensional convolutional neural network can be configured such that the B-allele frequency distribution can be used as input and is encoded into an input size of a height of 25, a width of 1, and a depth of 100. In some embodiments, each layer of the one-dimensional convolutional neural network performs 1×1 convolutions, followed by ReLU activation function.

In some embodiments, the trained machine-learning model includes a two-dimensional convolutional neural network. In some embodiments, the B-allele frequency distribution of the two-dimensional convolutional neural network is used as input and is encoded into an input size defined by a height of 25, a width of 100, and a depth of 1. In some embodiments, each convolutional layer of the two-dimensional convolutional neural network is followed by a ReLU layer. The output of the two-dimensional convolutional neural network can be a densely connected layer with a sigmoid activation function. In addition, hyperparameters of the two-dimensional convolutional neural network can tuned by adjusting a number of layers, a filter size, a number of filters, or a combination thereof.

The estimated metric identifying the tumor purity can be outputted. For example, a report that includes estimated metric can be outputted. In some embodiments, the report includes information identifying the B allele frequency distribution. The report may also include information identifying at least one diagnostic marker and/or at least one prognostic marker. In some embodiments, the report includes information identifying predicted somatic variants. The report may also include a treatment recommendation. In some embodiments, the treatment recommendation includes a recommendation to administer a treatment to the human subject. The treatment recommendation may include a recommendation to not administer a treatment to the human subject.

IV. Example Process for Estimating Tumor Purity from Single Samples

Figure 9:
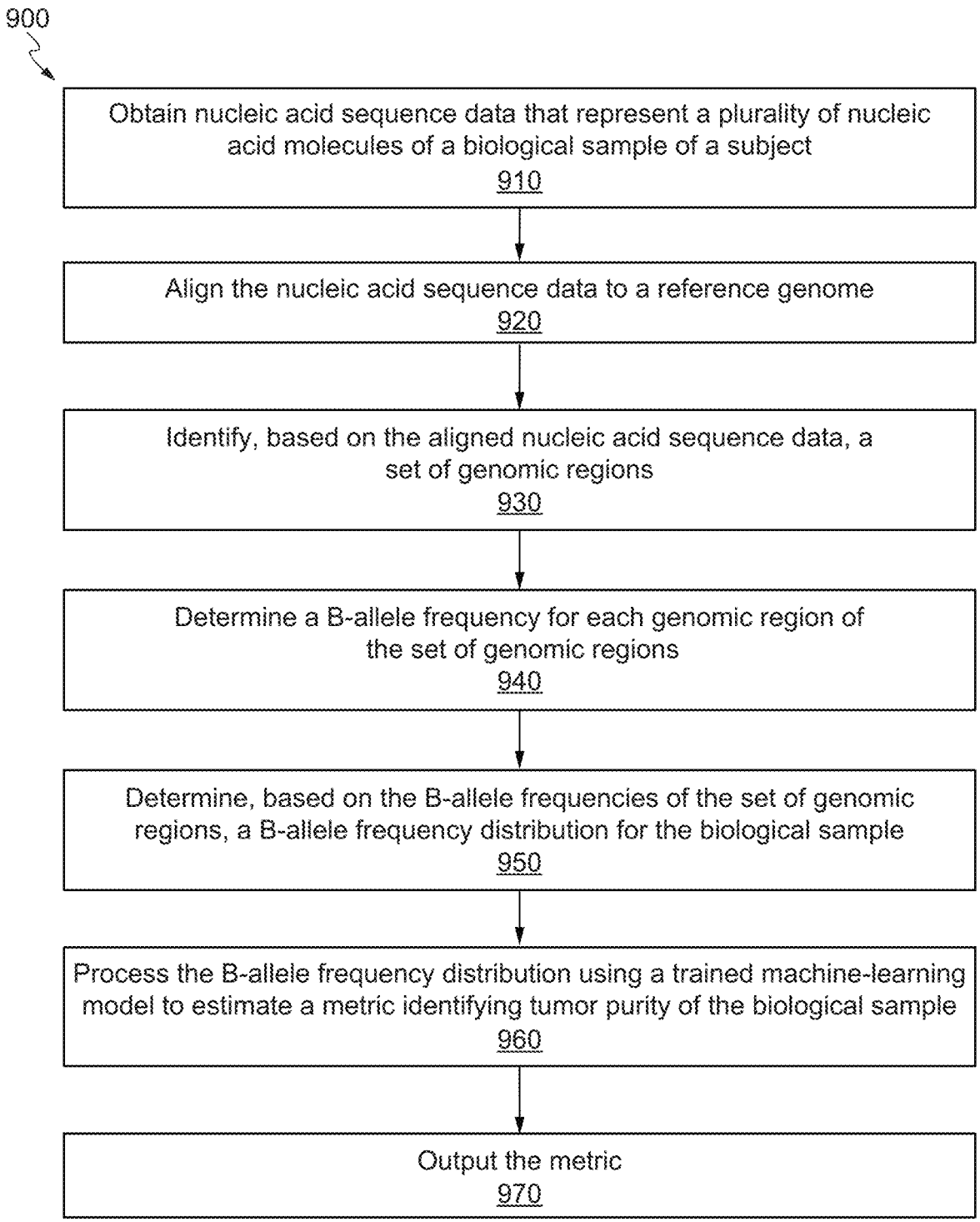
FIG. 9 includes a flowchart illustrating an example of a method of estimating tumor purity of a biological sample according to certain embodiments.

FIG. 9 includes a flowchart 900 illustrating an example of a method of estimating tumor purity of a biological sample according to certain embodiments. Operations described in flowchart 900 may be performed by, for example, a computer system implementing a trained machine-learning model, such as a trained one-dimensional or two-dimensional convolutional neural network. Although flowchart 900 may describe the operations as a sequential process, in various embodiments, many of the operations may be performed in parallel or concurrently. In addition, the order of the operations may be rearranged. An operation may have additional steps not shown in the figure. Furthermore, embodiments of the method may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium.

At operation 910, a computer system obtains nucleic acid sequence data that represent a plurality of nucleic acid molecules of a biological sample of a subject. The nucleic acid sequence data can be generated by sequencing the plurality of nucleic acid molecules of the tumor sample. In some instances, the plurality of nucleic acid molecules are isolated prior to the sequencing. The nucleic acid sequence data may correspond to whole exome sequence data. Alternatively or additionally, the nucleic acid sequence data is whole genome sequencing data.

At operation 920, the computer system aligns the nucleic acid sequence data to a reference genome. For example, the FASTQ files, which correspond to the nucleic acid sequence data, can be aligned to a reference genome to generate one or more BAM files.

At operation 930, the computer system identifies, based on the aligned nucleic acid sequence data, a set of genomic regions. Each genomic region of the set of genomic regions may include one or more nucleotide-sequence variants relative to a corresponding genomic region of the reference genome. In some instances, the computer system identifies one or more candidate nucleotide-sequence variants in the nucleic acid sequence data and calculates reference and alternate read depths for each of the one or more candidate nucleotide-sequence variants.

At operation 940, the computer system determines a BAF for each genomic region of the set of genomic regions. The BAF refers to a normalized measure of the allelic intensity ratio of two alleles (A and B). In some instances, a BAF of 100 or 0 indicates the complete absence of one of the two alleles (e.g. AA or BB), and a BAF of 50 indicates the equal presence of both alleles (e.g. AB). A BAF of 0, 50, or 100 can be expected for normal samples. In tumor samples, however, the mutations can alter the BAF values.

At operation 950, the computer system determines, based on the BAF of the set of genomic regions, a BAF distribution for the biological sample. In some instances, the B-allele frequency is normalized.

At operation 960, the computer system processes the B-allele frequency distribution using a trained machine-learning model to estimate a metric identifying tumor purity of the biological sample. In some instances, the trained machine-learning model is trained on a training dataset generated from nucleic acid sequence data derived from one or more tumor cells diluted into normal cells. The trained machine-learning model may have a mean absolute error of less than about 0.2.

At operation 970, the computer system outputs the metric. In some instances, the computer system outputs a report that includes the estimated metric identifying the tumor purity. In addition to the estimated metric, the report may include the determined B-allele frequency distribution. The report may also include other types of information, including, but not limited to, at least one biomarker, at least one prognostic marker, predicted somatic variants, and treatment recommendation (e.g., a recommendation whether or not a treatment should be administered to the subject).

V. Additional Considerations

A. Probing Techniques

Certain embodiments may include one or more labels. The one or more labels may be attached to one or more capture probes, nucleic acid molecules, beads, primers, or a combination thereof. Examples of labels include, but are not limited to, detectable labels, such as radioisotopes, fluorophores, chemiluminophores, chromophore, lumiphore, enzymes, colloidal particles, and fluorescent microparticles, quantum dots, as well as antigens, antibodies, haptens, avidin/streptavidin, biotin, haptens, enzymes cofactors/substrates, one or more members of a quenching system, a chromogens, haptens, a magnetic particles, materials exhibiting nonlinear optics, semiconductor nanocrystals, metal nanoparticles, enzymes, aptamers, and one or more members of a binding pair.

Certain embodiments may include one or more capture probes, a plurality of capture probes, or one or more capture probe sets. Typically, the capture probe comprises a nucleic acid binding site. The capture probe may further comprise one or more linkers. The capture probes may further comprise one or more labels. The one or more linkers may attach the one or more labels to the nucleic acid binding site.

Capture probes may hybridize to one or more nucleic acid molecules in a sample. Capture probes may hybridize to one or more genomic regions. Capture probes may hybridize to one or more genomic regions within, around, near, or spanning one or more genes, exons, introns, UTRs, or a combination thereof. Capture probes may hybridize to one or more genomic regions spanning one or more genes, exons, introns, UTRs, or a combination thereof. Capture probes may hybridize to one or more known inDels. Capture probes may hybridize to one or more known structural variants.

Certain embodiments may include 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more capture probes or capture probe sets. The one or more capture probes or capture probe sets may be different, similar, identical, or a combination thereof.

The one or more capture probe may comprise a nucleic acid binding site that hybridizes to at least a portion of the one or more nucleic acid molecules or variant or derivative thereof in the sample or subset of nucleic acid molecules. The capture probes may comprise a nucleic acid binding site that hybridizes to one or more genomic regions. The capture probes may hybridize to different, similar, and/or identical genomic regions. The one or more capture probes may be at least about 50%, 55%, 60%, 65%, 70%, 75%, 80%, 85%, 90%, 95%, 97%, 99% or more complementary to the one or more nucleic acid molecules or variant or derivative thereof.

The capture probes may comprise one or more nucleotides. The capture probes may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more nucleotides. The capture probes may comprise about 100 nucleotides. The capture probes may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the capture probes comprise between about 80 nucleotides to about 100 nucleotides.

The plurality of capture probes or the capture probe sets may comprise two or more capture probes with identical, similar, and/or different nucleic acid binding site sequences, linkers, and/or labels. For example, two or more capture probes comprise identical nucleic acid binding sites. In another example, two or more capture probes comprise similar nucleic acid binding sites. In yet another example, two or more capture probes comprise different nucleic acid binding sites. The two or more capture probes may further comprise one or more linkers. The two or more capture probes may further comprise different linkers. The two or more capture probes may further comprise similar linkers. The two or more capture probes may further comprise identical linkers. The two or more capture probes may further comprise one or more labels. The two or more capture probes may further comprise different labels. The two or more capture probes may further comprise similar labels. The two or more capture probes may further comprise identical labels.

B. Assays and Amplification Techniques

Certain embodiments may include conducting one or more assays on a sample comprising one or more nucleic acid molecules. Producing two or more subsets of nucleic acid molecules may comprise conducting one or more assays. The assays may be conducted on a subset of nucleic acid molecules from the sample. The assays maybe conducted on one or more nucleic acids molecules from the sample. The assays may be conducted on at least a portion of a subset of nucleic acid molecules. The assays may comprise one or more techniques, reagents, capture probes, primers, labels, and/or components for the detection, quantification, and/or analysis of one or more nucleic acid molecules.

Assays may include, but are not limited to, sequencing, amplification, hybridization, enrichment, isolation, elution, fragmentation, detection, quantification of one or more nucleic acid molecules. Assays may include methods for preparing one or more nucleic acid molecules.

Certain embodiments may include conducting one or more amplification reactions on one or more nucleic acid molecules in a sample. The term "amplification" refers to any process of producing at least one copy of a nucleic acid molecule. The terms "amplicons" and "amplified nucleic acid molecule" refer to a copy of a nucleic acid molecule and can be used interchangeably. The amplification reactions can comprise PCR-based methods, non-PCR based methods, or a combination thereof. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. PCR-based methods may include, but are not limited to, PCR, HD-PCR, Next Gen PCR, digital RTA, or any combination thereof. Additional PCR methods include, but are not limited to, linear amplification, allele-specific PCR, Alu PCR, assembly PCR, asymmetric PCR, droplet PCR, emulsion PCR, helicase dependent amplification HDA, hot start PCR, inverse PCR, linear-after-the-exponential (LATE)-PCR, long PCR, multiplex PCR, nested PCR, hemi-nested PCR, quantitative PCR, RT-PCR, real time PCR, single cell PCR, and touchdown PCR.

Certain embodiments may include conducting one or more hybridization reactions on one or more nucleic acid molecules in a sample. The hybridization reactions may comprise the hybridization of one or more capture probes to one or more nucleic acid molecules in a sample or subset of nucleic acid molecules. The hybridization reactions may comprise hybridizing one or more capture probe sets to one or more nucleic acid molecules in a sample or subset of nucleic acid molecules. The hybridization reactions may comprise one or more hybridization arrays, multiplex hybridization reactions, hybridization chain reactions, isothermal hybridization reactions, nucleic acid hybridization reactions, or a combination thereof. The one or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof. The hybridization reaction may comprise one or more capture probes, one or more beads, one or more labels, one or more subsets of nucleic acid molecules, one or more nucleic acid samples, one or more reagents, one or more wash buffers, one or more elution buffers, one or more hybridization buffers, one or more hybridization chambers, one or more incubators, one or more separators, or a combination thereof.

Certain embodiments may include conducting one or more enrichment reactions on one or more nucleic acid molecules in a sample. The enrichment reactions may comprise contacting a sample with one or more beads or bead sets. The enrichment reaction may comprise differential amplification of two or more subsets of nucleic acid molecules based on one or more genomic region features. For example, the enrichment reaction comprises differential amplification of two or more subsets of nucleic acid molecules based on GC content. Alternatively, or additionally, the enrichment reaction comprises differential amplification of two or more subsets of nucleic acid molecules based on methylation state. The enrichment reactions may comprise one or more hybridization reactions. The enrichment reactions may further comprise isolation and/or purification of one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. Alternatively, or additionally, the enrichment reaction may comprise enriching for one or more cell types in the sample. The one or more cell types may be enriched by flow cytometry.

The one or more enrichment reactions may produce one or more enriched nucleic acid molecules. The enriched nucleic acid molecules may comprise a nucleic acid molecule or variant or derivative thereof. For example, the enriched nucleic acid molecules comprise one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. The enriched nucleic acid molecules may be differentiated from non-enriched nucleic acid molecules by GC content, molecular size, genomic regions, genomic region features, or a combination thereof. The enriched nucleic acid molecules may be derived from one or more assays, supernatants, eluants, or a combination thereof. The enriched nucleic acid molecules may differ from the non-enriched nucleic acid molecules by mean size, mean GC content, genomic regions, or a combination thereof.

Certain embodiments may include conducting one or more isolation or purification reactions on one or more nucleic acid molecules in a sample. The isolation or purification reactions may comprise contacting a sample with one or more beads or bead sets. The isolation or purification reaction may comprise one or more hybridization reactions, enrichment reactions, amplification reactions, sequencing reactions, or a combination thereof. The isolation or purification reaction may comprise the use of one or more separators. The one or more separators may comprise a magnetic separator. The isolation or purification reaction may comprise separating bead bound nucleic acid molecules from bead free nucleic acid molecules. The isolation or purification reaction may comprise separating capture probe hybridized nucleic acid molecules from capture probe free nucleic acid molecules. The isolation or purification reaction may comprise separating a first subset of nucleic acid molecules from a second subset of nucleic acid molecules, wherein the first subset of nucleic acid molecules differ from the second subset on nucleic acid molecules by mean size, mean GC content, genomic regions, or a combination thereof.

Certain embodiments may include conducting one or more elution reactions on one or more nucleic acid molecules in a sample. The elution reactions may comprise contacting a sample with one or more beads or bead sets. The elution reaction may comprise separating bead bound nucleic acid molecules from bead free nucleic acid molecules. The elution reaction may comprise separating capture probe hybridized nucleic acid molecules from capture probe free nucleic acid molecules. The elution reaction may comprise separating a first subset of nucleic acid molecules from a second subset of nucleic acid molecules, wherein the first subset of nucleic acid molecules differ from the second subset on nucleic acid molecules by mean size, mean GC content, genomic regions, or a combination thereof.

Certain embodiments may include one or more fragmentation reactions. The fragmentation reactions may comprise fragmenting one or more nucleic acid molecules in a sample or subset of nucleic acid molecules to produce one or more fragmented nucleic acid molecules. The one or more nucleic acid molecules may be fragmented by sonication, needle shear, nebulisation, shearing (e.g., acoustic shearing, mechanical shearing, point-sink shearing), passage through a French pressure cell, or enzymatic digestion. Enzymatic digestion may occur by nuclease digestion (e.g., micrococcal nuclease digestion, endonucleases, exonucleases, RNAse H or DNase I). Fragmentation of the one or more nucleic acid molecules may result in fragment sized of about 100 base pairs to about 2000 base pairs, about 200 base pairs to about 1500 base pairs, about 200 base pairs to about 1000 base pairs, about 200 base pairs to about 500 base pairs, about 500 base pairs to about 1500 base pairs, and about 500 base pairs to about 1000 base pairs. The one or more fragmentation reactions may result in fragment sized of about 50 base pairs to about 1000 base pairs. The one or more fragmentation reactions may result in fragment sized of about 100 base pairs, 150 base pairs, 200 base pairs, 250 base pairs, 300 base pairs, 350 base pairs, 400 base pairs, 450 base pairs, 500 base pairs, 550 base pairs, 600 base pairs, 650 base pairs, 700 base pairs, 750 base pairs, 800 base pairs, 850 base pairs, 900 base pairs, 950 base pairs, 1000 base pairs or more.

Fragmenting the one or more nucleic acid molecules may comprise mechanical shearing of the one or more nucleic acid molecules in the sample for a period of time. The fragmentation reaction may occur for at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more seconds.

Fragmenting the one or more nucleic acid molecules may comprise contacting a nucleic acid sample with one or more beads. Fragmenting the one or more nucleic acid molecules may comprise contacting the nucleic acid sample with a plurality of beads, wherein the ratio of the volume of the plurality of beads to the volume of nucleic acid sample is about 0.10, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00 or more. Fragmenting the one or more nucleic acid molecules may comprise contacting the nucleic acid sample with a plurality of beads, wherein the ratio of the volume of the plurality of beads to the volume of nucleic acid is about 2.00, 1.90, 1.80, 1.70, 1.60, 1.50, 1.40, 1.30, 1.20, 1.10, 1.00, 0.90, 0.80, 0.70, 0.60, 0.50, 0.40, 0.30, 0.20, 0.10, 0.05, 0.04, 0.03, 0.02, 0.01 or less.

Certain embodiments may include conducting one or more detection reactions on one or more nucleic acid molecules in a sample. Detection reactions may comprise one or more sequencing reactions. Alternatively, conducting a detection reaction comprises optical sensing, electrical sensing, or a combination thereof. Optical sensing may comprise optical sensing of a photoilluminscence photon emission, fluorescence photon emission, pyrophosphate photon emission, chemiluminescence photon emission, or a combination thereof. Electrical sensing may comprise electrical sensing of an ion concentration, ion current modulation, nucleotide electrical field, nucleotide tunneling current, or a combination thereof.

Certain embodiments may include conducting one or more quantification reactions on one or more nucleic acid molecules in a sample. Quantification reactions may comprise sequencing, PCR, qPCR, digital PCR, or a combination thereof.

Certain embodiments may include one or more samples. Certain embodiments may include 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100 or more samples. The sample may be derived from a subject. The two or more samples may be derived from a single subject. The two or more samples may be derived from 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100 or more different subjects. The subject may be a mammal, reptiles, amphibians, avians, and fish. The mammal may be a human, ape, orangutan, monkey, chimpanzee, cow, pig, horse, rodent, bird, reptile, dog, cat, or other animal. A reptile may be a lizard, snake, alligator, turtle, crocodile, and tortoise. An amphibian may be a toad, frog, newt, and salamander. Examples of avians include, but are not limited to, ducks, geese, penguins, ostriches, and owls. Examples of fish include, but are not limited to, catfish, eels, sharks, and swordfish. Preferably, the subject is a human. The subject may suffer from a disease or condition (e.g., a cancer).

The two or more samples may be collected over 1, 2, 3, 4, 5, 6, 7, 8, 9, 10, 11, 12, 15, 20, 30, 40, 50, 60, 70, 80, 90, 100, 200, 300, 400, 500, 600, 700, 800, 900, 1000 or time points. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more hour period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more day period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more week period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more month period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more year period.

The sample may be from a body fluid, cell, skin, tissue, organ, or combination thereof. The sample may be a blood, plasma, a blood fraction, saliva, sputum, urine, semen, transvaginal fluid, cerebrospinal fluid, stool, a cell or a tissue biopsy. The sample may be from an adrenal gland, appendix, bladder, brain, ear, esophagus, eye, gall bladder, heart, kidney, large intestine, liver, lung, mouth, muscle, nose, pancreas, parathyroid gland, pineal gland, pituitary gland, skin, small intestine, spleen, stomach, thymus, thyroid gland, trachea, uterus, vermiform appendix, cornea, skin, heart valve, artery, or vein.

The samples may comprise one or more nucleic acid molecules. The nucleic acid molecule may be a DNA molecule, RNA molecule (e.g. mRNA, cRNA or miRNA), and DNA/RNA hybrids. Examples of DNA molecules include, but are not limited to, double-stranded DNA, single-stranded DNA, single-stranded DNA hairpins, cDNA, genomic DNA. The nucleic acid may be an RNA molecule, such as a double-stranded RNA, single-stranded RNA, ncRNA, RNA hairpin, and mRNA. Examples of ncRNA include, but are not limited to, siRNA, miRNA, snoRNA, piRNA, tiRNA, PASR, TASR, aTASR, TSSa-RNA, snRNA, RE-RNA, uaRNA, x-ncRNA, hY RNA, usRNA, snaR, and vtRNA.

Certain embodiments may include one or more containers. Certain embodiments may include 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more containers. The one or more containers may be different, similar, identical, or a combination thereof. Examples of containers include, but are not limited to, plates, microplates, PCR plates, wells, microwells, tubes, Eppendorf tubes, vials, arrays, microarrays, and chips.

Certain embodiments may include one or more reagents. Certain embodiments may include 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more reagents. The one or more reagents may be different, similar, identical, or a combination thereof. The reagents may improve the efficiency of the one or more assays. Reagents may improve the stability of the nucleic acid molecule or variant or derivative thereof. Reagents may include, but are not limited to, enzymes, proteases, nucleases, molecules, polymerases, reverse transcriptases, ligases, and chemical compounds. Certain embodiments may include conducting an assay comprising one or more antioxidants. Generally, antioxidants are molecules that inhibit oxidation of another molecule. Examples of antioxidants include, but are not limited to, ascorbic acid (e.g., vitamin C), glutathione, lipoic acid, uric acid, carotenes, a-tocopherol (e.g., vitamin E), ubiquinol (e.g., coenzyme Q), and vitamin A.

Certain embodiments may include one or more buffers or solutions. The one or more buffers or solutions may be different, similar, identical, or a combination thereof. The buffers or solutions may improve the efficiency of the one or more assays. Buffers or solutions may improve the stability of the nucleic acid molecule or variant or derivative thereof. Buffers or solutions may include, but are not limited to, wash buffers, elution buffers, and hybridization buffers.

Certain embodiments may include one or more beads, a plurality of beads, or one or more bead sets. Certain embodiments may include 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more beads or bead sets. The one or more beads or bead sets may be different, similar, identical, or a combination thereof. The beads may be magnetic, antibody coated, protein A crosslinked, protein G crosslinked, streptavidin coated, oligonucleotide conjugated, silica coated, or a combination thereof. Examples of beads include, but are not limited to, Ampure beads, AMPure XP beads, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, anti-fluorochrome microbead, and BcMag™ Carboxy-Terminated Magnetic Beads. In some aspects of the disclosure, the one or more beads comprise one or more Ampure beads. Alternatively, or additionally, the one or more beads comprise AMPure XP beads.

Certain embodiments may include one or more primers, a plurality of primers, or one or more primer sets. The primers may further comprise one or more linkers. The primers may further comprise or more labels. The primers may be used in one or more assays. For example, the primers are used in one or more sequencing reactions, amplification reactions, or a combination thereof. Certain embodiments may include 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more primers or primer sets. The primers may comprise about 100 nucleotides. The primers may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the primers comprise between about 80 nucleotides to about 100 nucleotides. The one or more primers or primer sets may be different, similar, identical, or a combination thereof.

The primers may hybridize to at least a portion of the one or more nucleic acid molecules or variant or derivative thereof in the sample or subset of nucleic acid molecules. The primers may hybridize to one or more genomic regions. The primers may hybridize to different, similar, and/or identical genomic regions. The one or more primers may be at least about 50%, 55%, 60%, 65%, 70%, 75%, 80%, 85%, 90%, 95%, 97%, 99% or more complementary to the one or more nucleic acid molecules or variant or derivative thereof.

The primers may comprise one or more nucleotides. The primers may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more nucleotides. The primers may comprise about 100 nucleotides. The primers may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the primers comprise between about 80 nucleotides to about 100 nucleotides.

The plurality of primers or the primer sets may comprise two or more primers with identical, similar, and/or different sequences, linkers, and/or labels. For example, two or more primers comprise identical sequences. In another example, two or more primers comprise similar sequences. In yet another example, two or more primers comprise different sequences. The two or more primers may further comprise one or more linkers. The two or more primers may further comprise different linkers. The two or more primers may further comprise similar linkers. The two or more primers may further comprise identical linkers. The two or more primers may further comprise one or more labels. The two or more primers may further comprise different labels. The two or more primers may further comprise similar labels. The two or more primers may further comprise identical labels.

The capture probes, primers, labels, and/or beads may comprise one or more nucleotides. The one or more nucleotides may comprise RNA, DNA, a mix of DNA and RNA residues or their modified analogs such as 2'-0Me, or 2'-fluoro (2'-F), locked nucleic acid (LNA), or abasic sites.

Certain embodiments may include one or more labels. Certain embodiments may include 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more labels. The one or more labels may be different, similar, identical, or a combination thereof.

Examples of labels include, but are not limited to, chemical, biochemical, biological, colorimetric, enzymatic, fluorescent, and luminescent labels, which are well known in the art. The label comprise a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

The label may be a chemical label. Examples of chemical labels can include, but are not limited to, biotin and radiosiotypes (e.g., iodine, carbon, phosphate, hydrogen).

The methods, kits, and compositions disclosed herein may comprise a biological label. The biological labels may comprise metabolic labels, including, but not limited to, bioorthogonal azide-modified amino acids, sugars, and other compounds.

The methods, kits, and compositions disclosed herein may comprise an enzymatic label. Enzymatic labels can include, but are not limited to, horseradish peroxidase (HRP), alkaline phosphatase (AP), glucose oxidase, and 0-galactosidase. The enzymatic label may be luciferase.

The methods, kits, and compositions disclosed herein may comprise a fluorescent label. The fluorescent label may be an organic dye (e.g., FITC), biological fluorophore (e.g., green fluorescent protein), or quantum dot. A non-limiting list of fluorescent labels includes fluorescein isothiocyante (FITC), DyLight Fluors, fluorescein, rhodamine (tetramethyl rhodamine isothiocyanate, TRITC), coumarin, Lucifer Yellow, and BODIPY. The label may be a fluorophore. Exemplary fluorophores include, but are not limited to, indocarbocyanine (C3), indodicarbocyanine (C5), Cy3, Cy3.5, Cy5, Cy5.5, Cy7, Texas Red, Pacific Blue, Oregon Green 488, Alexa Fluor®-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX™), LIZ™, VIC™ NED™ PET™, SYBR, PicoGreen, RiboGreen, and the like. The fluorescent label may be a green fluorescent protein (GFP), red fluorescent protein (RFP), yellow fluorescent protein, phycobiliproteins (e.g., allophycocyanin, phycocyanin, phycoerythrin, and phycoerythrocyanin).

Certain embodiments may include one or more linkers. Certain embodiments may include 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more linkers. The one or more linkers may be different, similar, identical, or a combination thereof.

Suitable linkers comprise any chemical or biological compound capable of attaching to a label, primer, and/or capture probe disclosed herein. If the linker attaches to both the label and the primer or capture probe, then a suitable linker would be capable of sufficiently separating the label and the primer or capture probe. Suitable linkers would not significantly interfere with the ability of the primer and/or capture probe to hybridize to a nucleic acid molecule, portion thereof, or variant or derivative thereof. Suitable linkers would not significantly interfere with the ability of the label to be detected. The linker may be rigid. The linker may be flexible. The linker may be semi rigid. The linker may be proteolytically stable (e.g., resistant to proteolytic cleavage). The linker may be proteolytically unstable (e.g., sensitive to proteolytic cleavage). The linker may be helical. The linker may be non-helical. The linker may be coiled. The linker may be (3-stranded. The linker may comprise a turn conformation. The linker may be a single chain. The linker may be a long chain. The linker may be a short chain. The linker may comprise at least about 5 residues, at least about 10 residues, at least about 15 residues, at least about 20 residues, at least about 25 residues, at least about 30 residues, or at least about 40 residues or more.

Examples of linkers include, but are not limited to, hydrazone, disulfide, thioether, and peptide linkers. The linker may be a peptide linker. The peptide linker may comprise a proline residue. The peptide linker may comprise an arginine, phenylalenine, threonine, glutamine, glutamate, or any combination thereof. The linker may be a heterobifunctional crosslinker.

Certain embodiments may include conducting 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, or 50 or more assays on a sample comprising one or more nucleic acid molecules. The two or more assays may be different, similar, identical, or a combination thereof. For example, Certain embodiments comprise conducting two or more sequencing reactions. In another example, Certain embodiments comprise conducting two or more assays, wherein at least one of the two or more assays comprises a sequencing reaction. In yet another example, Certain embodiments comprise conducting two or more assays, wherein at least two of the two or more assays comprises a sequencing reaction and a hybridization reaction. The two or more assays may be performed sequentially, simultaneously, or a combination thereof. For example, the two or more sequencing reactions may be performed simultaneously. In another example, Certain embodiments comprise conducting a hybridization reaction, followed by a sequencing reaction. In yet another example, Certain embodiments comprise conducting two or more hybridization reactions simultaneously, followed by conducting two or more sequencing reactions simultaneously. The two or more assays may be performed by one or more devices. For example, two or more amplification reactions may be performed by a PCR machine. In another example, two or more sequencing reactions may be performed by two or more sequencers.

C. Devices

Certain embodiments may include one or more devices. Certain embodiments may include one or more assays comprising one or more devices. Certain embodiments may include the use of one or more devices to perform one or more steps or assays. Certain embodiments may include the use of one or more devices in one or more steps or assays. For example, conducting a sequencing reaction may comprise one or more sequencers. In another example, producing a subset of nucleic acid molecules may comprise the use of one or more magnetic separators. In yet another example, one or more processors may be used in the analysis of one or more nucleic acid samples. Exemplary devices include, but are not limited to, sequencers, thermocyclers, real-time PCR instruments, magnetic separators, transmission devices, hybridization chambers, electrophoresis apparatus, centrifuges, microscopes, imagers, fluorometers, luminometers, plate readers, computers, processors, and bioanalyzers.

Certain embodiments may include one or more sequencers. The one or more sequencers may comprise one or more HiSeq, MiSeq, HiScan, Genome Analyzer IIx, SOLiD Sequencer, Ion Torrent PGM, 454 GS Junior, Pac Bio RS, or a combination thereof. The one or more sequencers may comprise one or more sequencing platforms. The one or more sequencing platforms may comprise GS FLX by 454 Life Technologies/Roche, Genome Analyzer by Solexa/Illumina, SOLiD by Applied Biosystems, CGA Platform by Complete Genomics, PacBio RS by Pacific Biosciences, or a combination thereof.

Certain embodiments may include one or more thermocyclers. The one or more thermocyclers may be used to amplify one or more nucleic acid molecules. Certain embodiments may include one or more real-time PCR instruments. The one or more real-time PCR instruments may comprise a thermal cycler and a fluorimeter. The one or more thermocyclers may be used to amplify and detect one or more nucleic acid molecules.

Certain embodiments may include one or more magnetic separators. The one or more magnetic separators may be used for separation of paramagnetic and ferromagnetic particles from a suspension. The one or more magnetic separators may comprise one or more LifeStep™ biomagnetic separators, SPHERO™ FlexiMag separator, SPHERO™ MicroMag separator, SPHERO™ HandiMag separator, SPHERO™ MiniTube Mag separator, SPHERO™ UltraMag separator, DynaMag™ magnet, DynaMag™-2 Magnet, or a combination thereof.

Certain embodiments may include one or more bioanalyzers. Generaly, a bioanalyzer is a chip-based capillary electrophoresis machine that can analyse RNA, DNA, and proteins. The one or more bioanalyzers may comprise Agilent's 2100 Bioanalyzer.

Certain embodiments may include one or more processors. The one or more processors may analyze, compile, store, sort, combine, assess or otherwise process one or more data and/or results from one or more assays, one or more data and/or results based on or derived from one or more assays, one or more outputs from one or more assays, one or more outputs based on or derived from one or more assays, one or more outputs from one or data and/or results, one or more outputs based on or derived from one or more data and/or results, or a combination thereof. The one or more processors may transmit the one or more data, results, or outputs from one or more assays, one or more data, results, or outputs based on or derived from one or more assays, one or more outputs from one or more data or results, one or more outputs based on or derived from one or more data or results, or a combination thereof. The one or more processors may receive and/or store requests from a user. The one or more processors may produce or generate one or more data, results, outputs. The one or more processors may produce or generate one or more biomedical reports. The one or more processors may transmit one or more biomedical reports. The one or more processors may analyze, compile, store, sort, combine, assess or otherwise process information from one or more databases, one or more data or results, one or more outputs, or a combination thereof. The one or more processors may analyze, compile, store, sort, combine, assess or otherwise process information from 1, 2, 3, 4, 5, 6, 7, 8, 9, 10, 11, 12, 13, 14, 15, 16, 17, 18, 19, 20, 30 or more databases. The one or more processors may transmit one or more requests, data, results, outputs and/or information to one or more users, processors, computers, computer systems, memory locations, devices, databases, or a combination thereof. The one or more processors may receive one or more requests, data, results, outputs and/or information from one or more users, processors, computers, computer systems, memory locations, devices, databases or a combination thereof. The one or more processors may retrieve one or more requests, data, results, outputs and/or information from one or more users, processors, computers, computer systems, memory locations, devices, databases or a combination thereof.

Certain embodiments may include one or more memory locations. The one or more memory locations may store information, data, results, outputs, requests, or a combination thereof. The one or more memory locations may receive information, data, results, outputs, requests, or a combination thereof from one or more users, processors, computers, computer systems, devices, or a combination thereof.

Methods described herein can be implemented with the aid of one or more computers and/or computer systems. A computer or computer system may comprise electronic storage locations (e.g., databases, memory) with machine-executable code for implementing the methods provided herein, and one or more processors for executing the machine-executable code.

The code can be pre-compiled and configured for use with a machine have a processer adapted to execute the code or can be compiled during runtime. The code can be supplied in a programming language that can be selected to enable the code to execute in a pre-compiled or as-compiled fashion.

The one or more computers and/or computer systems may analyze, compile, store, sort, combine, assess or otherwise process one or more data and/or results from one or more assays, one or more data and/or results based on or derived from one or more assays, one or more outputs from one or more assays, one or more outputs based on or derived from one or more assays, one or more outputs from one or data and/or results, one or more outputs based on or derived from one or more data and/or results, or a combination thereof. The one or more computers and/or computer systems may transmit the one or more data, results, or outputs from one or more assays, one or more data, results, or outputs based on or derived from one or more assays, one or more outputs from one or more data or results, one or more outputs based on or derived from one or more data or results, or a combination thereof. The one or more computers and/or computer systems may receive and/or store requests from a user. The one or more computers and/or computer systems may produce or generate one or more data, results, outputs. The one or more computers and/or computer systems may produce or generate one or more biomedical reports. The one or more computers and/or computer systems may transmit one or more biomedical reports. The one or more computers and/or computer systems may analyze, compile, store, sort, combine, assess or otherwise process information from one or more databases, one or more data or results, one or more outputs, or a combination thereof. The one or more computers and/or computer systems may analyze, compile, store, sort, combine, assess or otherwise process information from 1, 2, 3, 4, 5, 6, 7, 8, 9, 10, 11, 12, 13, 14, 15, 16, 17, 18, 19, 20, 30 or more databases. The one or more computers and/or computer systems may transmit one or more requests, data, results, outputs, and/or information to one or more users, processors, computers, computer systems, memory locations, devices, or a combination thereof. The one or more computers and/or computer systems may receive one or more requests, data, results, outputs, and/or information from one or more users, processors, computers, computer systems, memory locations, devices, or a combination thereof. The one or more computers and/or computer systems may retrieve one or more requests, data, results, outputs and/or information from one or more users, processors, computers, computer systems, memory locations, devices, databases or a combination thereof.

D. Databases

Certain embodiments may include one or more databases. Certain embodiments may include at least about 1, 2, 3, 4, 5, 6, 7, 8, 9, 10, 11, 12, 13, 14, 15, 16, 17, 18, 19, 20, 30 or more databases. The databases may comprise genomic, proteomic, pharmacogenomic, biomedical, and scientific databases. The databases may be publicly available databases. Alternatively, or additionally, the databases may comprise proprietary databases. The databases may be commercially available databases. The databases include, but are not limited to, Cosmic, GnomAD, Dbsnp, Mills Indels, MendelDB, PharmGKB, Varimed, Regulome, curated BreakSeq junctions, Online Mendelian Inheritance in Man (OMIM), Human Genome Mutation Database (HGMD), NCBI db SNP, NCBI RefSeq, GENCODE, GO (gene ontology), and Kyoto Encyclopedia of Genes and Genomes (KEGG).

Certain embodiments may include analyzing one or more databases. Certain embodiments may include analyzing at least about 1, 2, 3, 4, 5, 6, 7, 8, 9, 10, 11, 12, 13, 14, 15, 16, 17, 18, 19, 20, 30 or more databases. Analyzing the one or more databases may comprise one or more algorithms, computers, processors, memory locations, devices, or a combination thereof.

Certain embodiments may include identifying one or more nucleic acid regions based on data and/or information from one or more databases. Certain embodiments may include identifying one or more sets of nucleic acid regions based on data and/or information from one or more databases. Certain embodiments may include identifying one or more nucleic acid regions and/or sets of nucleic acid regions based on data and/or information from at least about 2 or more databases. Certain embodiments may include identifying one or more nucleic acid regions and/or sets of nucleic acid regions based on data and/or information from at least about 3 or more databases. Certain embodiments may include identifying one or more nucleic acid regions and/or sets of nucleic acid regions based on data and/or information from at least about 4, 5, 6, 7, 8, 9, 10, 11, 12, 13, 14, 15, 16, 17, 18, 19, 20, 30 or more databases.

Certain embodiments may include analyzing one or more results based on data and/or information from one or more databases. Certain embodiments may include analyzing one or more sets of results based on data and/or information from one or more databases. Certain embodiments may include analyzing one or more combined results based on data and/or information from one or more databases. Certain embodiments may include analyzing one or more results, sets of results, and/or combined results based on data and/or information from at least about 2 or more databases. Certain embodiments may include analyzing one or more results, sets of results, and/or combined results based on data and/or information from at least about 3 or more databases. Certain embodiments may include analyzing one or more results, sets of results, and/or combined results based on data and/or information from at least about 4, 5, 6, 7, 8, 9, 10, 11, 12, 13, 14, 15, 16, 17, 18, 19, 20, 30 or more databases.

Certain embodiments may include comparing one or more results based on data and/or information from one or more databases. Certain embodiments may include comparing one or more sets of results based on data and/or information from one or more databases. Certain embodiments may include comparing one or more combined results based on data and/or information from one or more databases. Certain embodiments may include comparing one or more results, sets of results, and/or combined results based on data and/or information from at least about 2 or more databases. Certain embodiments may include comparing one or more results, sets of results, and/or combined results based on data and/or information from at least about 3 or more databases. Certain embodiments may include comparing one or more results, sets of results, and/or combined results based on data and/or information from at least about 4, 5, 6, 7, 8, 9, 10, 11, 12, 13, 14, 15, 16, 17, 18, 19, 20, 30 or more databases.

Certain embodiments may include biomedical databases, genomic databases, biomedical reports, disease reports, case-control analysis, and rare variant discovery analysis based on data and/or information from one or more databases, one or more assays, one or more data or results, one or more outputs based on or derived from one or more assays, one or more outputs based on or derived from one or more data or results, or a combination thereof.

E. Datasets and Analysis

Certain embodiments may include one or more data, one or more data sets, one or more combined data, one or more combined data sets, one or more results, one or more sets of results, one or more combined results, or a combination thereof. The data and/or results may be based on or derived from one or more assays, one or more databases, or a combination thereof. Certain embodiments may include analysis of the one or more data, one or more data sets, one or more combined data, one or more combined data sets, one or more results, one or more sets of results, one or more combined results, or a combination thereof. Certain embodiments may include processing of the one or more data, one or more data sets, one or more combined data, one or more combined data sets, one or more results, one or more sets of results, one or more combined results, or a combination thereof.

Certain embodiments may include at least one analysis and at least one processing of the one or more data, one or more data sets, one or more combined data, one or more combined data sets, one or more results, one or more sets of results, one or more combined results, or a combination thereof. Certain embodiments may include one or more analyses and one or more processing of the one or more data, one or more data sets, one or more combined data, one or more combined data sets, one or more results, one or more sets of results, one or more combined results, or a combination thereof. Certain embodiments may include at least 1, 2, 3, 4, 5, 6, 7, 8, 9, 10, 15, 20, 30, 40, 50, 60, 70, 80, 90, 100, 200, 300, 400, 500, 600, 700, 800, 900, 1000 or more distinct analyses of the one or more data, one or more data sets, one or more combined data, one or more combined data sets, one or more results, one or more sets of results, one or more combined results, or a combination thereof. Certain embodiments may include at least 1, 2, 3, 4, 5, 6, 7, 8, 9, 10, 15, 20, 30, 40, 50, 60, 70, 80, 90, 100, 200, 300, 400, 500, 600, 700, 800, 900, 1000 or more distinct processing of the one or more data, one or more data sets, one or more combined data, one or more combined data sets, one or more results, one or more sets of results, one or more combined results, or a combination thereof. The one or more analyses and/or one or more processing may occur simultaneously, sequentially, or a combination thereof.

The one or more analyses and/or one or more processing may occur over 1, 2, 3, 4, 5, 6, 7, 8, 9, 10, 11, 12, 15, 20, 30, 40, 50, 60, 70, 80, 90, 100, 200, 300, 400, 500, 600, 700, 800, 900, 1000 or more time points. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more hour period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more day period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more week period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more month period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more year period.

Certain embodiments may include one or more data. The one or more data may comprise one or more raw data based on or derived from one or more assays. The one or more data may comprise one or more raw data based on or derived from one or more databases. The one or more data may comprise at least partially analyzed data based on or derived from one or more raw data. The one or more data may comprise at least partially processed data based on or derived from one or more raw data. The one or more data may comprise fully analyzed data based on or derived from one or more raw data. The one or more data may comprise fully processed data based on or derived from one or more raw data. The data may comprise sequencing read data or expression data. The data may comprise biomedical, scientific, pharmacological, and/or genetic information.

Certain embodiments may include one or more combined data. The one or more combined data may comprise two or more data. The one or more combined data may comprise two or more data sets. The one or more combined data may comprise one or more raw data based on or derived from one or more assays. The one or more combined data may comprise one or more raw data based on or derived from one or more databases. The one or more combined data may comprise at least partially analyzed data based on or derived from one or more raw data. The one or more combined data may comprise at least partially processed data based on or derived from one or more raw data. The one or more combined data may comprise fully analyzed data based on or derived from one or more raw data. The one or more combined data may comprise fully processed data based on or derived from one or more raw data. One or more combined data may comprise sequencing read data or expression data. One or more combined data may comprise biomedical, scientific, pharmacological, and/or genetic information.

Certain embodiments may include one or more data sets. The one or more data sets may comprise one or more data. The one or more data sets may comprise one or more combined data. The one or more data sets may comprise one or more raw data based on or derived from one or more assays. The one or more data sets may comprise one or more raw data based on or derived from one or more databases. The one or more data sets may comprise at least partially analyzed data based on or derived from one or more raw data. The one or more data sets may comprise at least partially processed data based on or derived from one or more raw data. The one or more data sets may comprise fully analyzed data based on or derived from one or more raw data. The one or more data sets may comprise fully processed data based on or derived from one or more raw data. The data sets may comprise sequencing read data or expression data. The data sets may comprise biomedical, scientific, pharmacological, and/or genetic information.

Certain embodiments may include one or more combined data sets. The one or more combined data sets may comprise two or more data. The one or more combined data sets may comprise two or more combined data. The one or more combined data sets may comprise two or more data sets. The one or more combined data sets may comprise one or more raw data based on or derived from one or more assays. The one or more combined data sets may comprise one or more raw data based on or derived from one or more databases. The one or more combined data sets may comprise at least partially analyzed data based on or derived from one or more raw data. The one or more combined data sets may comprise at least partially processed data based on or derived from one or more raw data. The one or more combined data sets may comprise fully analyzed data based on or derived from one or more raw data. The one or more combined data sets may comprise fully processed data based on or derived from one or more raw data. Certain embodiments may further comprise further processing and/or analysis of the combined data sets. One or more combined data sets may comprise sequencing read data or expression data. One or more combined data sets may comprise biomedical, scientific, pharmacological, and/or genetic information.

Certain embodiments may include one or more results. The one or more results may comprise one or more data, data sets, combined data, and/or combined data sets. The one or more results may be based on or derived from one or more data, data sets, combined data, and/or combined data sets. The one or more results may be produced from one or more assays. The one or more results may be based on or derived from one or more assays. The one or more results may be based on or derived from one or more databases. The one or more results may comprise at least partially analyzed results based on or derived from one or more data, data sets, combined data, and/or combined data sets. The one or more results may comprise at least partially processed results based on or derived from one or more data, data sets, combined data, and/or combined data sets. The one or more results may comprise at fully analyzed results based on or derived from one or more data, data sets, combined data, and/or combined data sets. The one or more results may comprise fully processed results based on or derived from one or more data, data sets, combined data, and/or combined data sets. The results may comprise sequencing read data or expression data. The results may comprise biomedical, scientific, pharmacological, and/or genetic information.

Certain embodiments may include one or more sets of results. The one or more sets of results may comprise one or more data, data sets, combined data, and/or combined data sets. The one or more sets of results may be based on or derived from one or more data, data sets, combined data, and/or combined data sets. The one or more sets of results may be produced from one or more assays. The one or more sets of results may be based on or derived from one or more assays. The one or more sets of results may be based on or derived from one or more databases. The one or more sets of results may comprise at least partially analyzed sets of results based on or derived from one or more data, data sets, combined data, and/or combined data sets. The one or more sets of results may comprise at least partially processed sets of results based on or derived from one or more data, data sets, combined data, and/or combined data sets. The one or more sets of results may comprise at fully analyzed sets of results based on or derived from one or more data, data sets, combined data, and/or combined data sets. The one or more sets of results may comprise fully processed sets of results based on or derived from one or more data, data sets, combined data, and/or combined data sets. The sets of results may comprise sequencing read data or expression data. The sets of results may comprise biomedical, scientific, pharmacological, and/or genetic information.

Certain embodiments may include one or more combined results. The combined results may comprise one or more results, sets of results, and/or combined sets of results. The combined results may be based on or derived from one or more results, sets of results, and/or combined sets of results. The one or more combined results may comprise one or more data, data sets, combined data, and/or combined data sets. The one or more combined results may be based on or derived from one or more data, data sets, combined data, and/or combined data sets. The one or more combined results may be produced from one or more assays. The one or more combined results may be based on or derived from one or more assays. The one or more combined results may be based on or derived from one or more databases. The one or more combined results may comprise at least partially analyzed combined results based on or derived from one or more data, data sets, combined data, and/or combined data sets. The one or more combined results may comprise at least partially processed combined results based on or derived from one or more data, data sets, combined data, and/or combined data sets. The one or more combined results may comprise at fully analyzed combined results based on or derived from one or more data, data sets, combined data, and/or combined data sets. The one or more combined results may comprise fully processed combined results based on or derived from one or more data, data sets, combined data, and/or combined data sets. The combined results may comprise sequencing read data or expression data. The combined results may comprise biomedical, scientific, pharmacological, and/or genetic information.

Certain embodiments may include one or more combined sets of results. The combined sets of results may comprise one or more results, sets of results, and/or combined results. The combined sets of results may be based on or derived from one or more results, sets of results, and/or combined results. The one or more combined sets of results may comprise one or more data, data sets, combined data, and/or combined data sets. The one or more combined sets of results may be based on or derived from one or more data, data sets, combined data, and/or combined data sets. The one or more combined sets of results may be produced from one or more assays. The one or more combined sets of results may be based on or derived from one or more assays. The one or more combined sets of results may be based on or derived from one or more databases. The one or more combined sets of results may comprise at least partially analyzed combined sets of results based on or derived from one or more data, data sets, combined data, and/or combined data sets. The one or more combined sets of results may comprise at least partially processed combined sets of results based on or derived from one or more data, data sets, combined data, and/or combined data sets. The one or more combined sets of results may comprise at fully analyzed combined sets of results based on or derived from one or more data, data sets, combined data, and/or combined data sets. The one or more combined sets of results may comprise fully processed combined sets of results based on or derived from one or more data, data sets, combined data, and/or combined data sets. The combined sets of results may comprise sequencing read data or expression data. The combined sets of results may comprise biomedical, scientific, pharmacological, and/or genetic information.

Certain embodiments may include one or more outputs, sets of outputs, combined outputs, and/or combined sets of outputs. The methods, libraries, kits and systems herein may comprise producing one or more outputs, sets of outputs, combined outputs, and/or combined sets of outputs. The sets of outputs may comprise one or more outputs, one or more combined outputs, or a combination thereof. The combined outputs may comprise one or more outputs, one or more sets of outputs, one or more combined sets of outputs, or a combination thereof. The combined sets of outputs may comprise one or more outputs, one or more sets of outputs, one or more combined outputs, or a combination thereof. The one or more outputs, sets of outputs, combined outputs, and/or combined sets of outputs may be based on or derived from one or more data, one or more data sets, one or more combined data, one or more combined data sets, one or more results, one or more sets of results, one or more combined results, or a combination thereof. The one or more outputs, sets of outputs, combined outputs, and/or combined sets of outputs may be based on or derived from one or more databases. The one or more outputs, sets of outputs, combined outputs, and/or combined sets of outputs may comprise one or more biomedical reports, biomedical outputs, rare variant outputs, pharmacogenetic outputs, population study outputs, case-control outputs, biomedical databases, genomic databases, disease databases, net content.

Certain embodiments may include one or more biomedical outputs, one or more sets of biomedical outputs, one or more combined biomedical outputs, one or more combined sets of biomedical outputs. The methods, libraries, kits and systems herein may comprise producing one or more biomedical outputs, one or more sets of biomedical outputs, one or more combined biomedical outputs, one or more combined sets of biomedical outputs. The sets of biomedical outputs may comprise one or more biomedical outputs, one or more combined biomedical outputs, or a combination thereof. The combined biomedical outputs may comprise one or more biomedical outputs, one or more sets of biomedical outputs, one or more combined sets of biomedical outputs, or a combination thereof. The combined sets of biomedical outputs may comprise one or more biomedical outputs, one or more sets of biomedical outputs, one or more combined biomedical outputs, or a combination thereof. The one or more biomedical outputs, one or more sets of biomedical outputs, one or more combined biomedical outputs, one or more combined sets of biomedical outputs may be based on or derived from one or more data, one or more data sets, one or more combined data, one or more combined data sets, one or more results, one or more sets of results, one or more combined results, one or more outputs, one or more sets of outputs, one or more combined outputs, one or more sets of combined outputs, or a combination thereof. The one or more biomedical outputs may comprise biomedical information of a subject. The biomedical information of the subject may predict, diagnose, and/or prognose one or more biomedical features. The one or more biomedical features may comprise the status of a disease or condition, genetic risk of a disease or condition, reproductive risk, genetic risk to a fetus, risk of an adverse drug reaction, efficacy of a drug therapy, prediction of optimal drug dosage, transplant tolerance, or a combination thereof.

Certain embodiments may include one or more biomedical reports. The methods, libraries, kits and systems herein may comprise producing one or more biomedical reports. The one or more biomedical reports may be based on or derived from one or more data, one or more data sets, one or more combined data, one or more combined data sets, one or more results, one or more sets of results, one or more combined results, one or more outputs, one or more sets of outputs, one or more combined outputs, one or more sets of combined outputs, one or more biomedical outputs, one or more sets of biomedical outputs, combined biomedical outputs, one or more sets of biomedical outputs, or a combination thereof. The biomedical report may predict, diagnose, and/or prognose one or more biomedical features. The one or more biomedical features may comprise the status of a disease or condition, genetic risk of a disease or condition, reproductive risk, genetic risk to a fetus, risk of an adverse drug reaction, efficacy of a drug therapy, prediction of optimal drug dosage, transplant tolerance, or a combination thereof.

Certain embodiments may also comprise the transmission of one or more data, information, results, outputs, reports or a combination thereof. For example, data/information based on or derived from the one or more assays are transmitted to another device and/or instrument. In another example, the data, results, outputs, biomedical outputs, biomedical reports, or a combination thereof are transmitted to another device and/or instrument. The information obtained from an algorithm may also be transmitted to another device and/or instrument. Information based on the analysis of one or more databases may be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc.). The data, results, outputs, biomedical outputs, biomedical reports can be transmitted to a patient and/or a healthcare provider.

Transmission may be based on the analysis of one or more data, results, information, databases, outputs, reports, or a combination thereof. For example, transmission of a second report is based on the analysis of a first report. Alternatively, transmission of a report is based on the analysis of one or more data or results. Transmission may be based on receiving one or more requests. For example, transmission of a report may be based on receiving a request from a user (e.g., patient, healthcare provider, individual).

Transmission of the data/information may comprise digital transmission or analog transmission. Digital transmission may comprise the physical transfer of data (a digital bit stream) over a point-to-point or point-to-multipoint communication channel. Examples of such channels are copper wires, optical fibres, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

Certain embodiments may include one or more sample identifiers. The sample identifiers may comprise labels, barcodes, and other indicators which can be linked to one or more samples and/or subsets of nucleic acid molecules. Certain embodiments may include one or more processors, one or more memory locations, one or more computers, one or more monitors, one or more computer software, one or more algorithms for linking data, results, outputs, biomedical outputs, and/or biomedical reports to a sample.

Certain embodiments may include a processor for correlating the expression levels of one or more nucleic acid molecules with a prognosis of disease outcome. Certain embodiments may include one or more of a variety of correlative techniques, including lookup tables, algorithms, multivariate models, and linear or nonlinear combinations of expression models or algorithms. The expression levels may be converted to one or more likelihood scores, reflecting a likelihood that the patient providing the sample may exhibit a particular disease outcome. The models and/or algorithms can be provided in machine readable format and can optionally further designate a treatment modality for a patient or class of patients.

In some instances, the methods and systems as described herein are used to generate an output comprising detection and/or quantitation of genomic DNA regions such as a region containing a DNA polymorphism (e.g., a germline variant or a somatic variant). In some instances, the detection of the one or more genomic regions is based on one or more algorithms, depending on the source of data inputs or databases that are described elsewhere in the instant specification. Each of the one or more algorithms can be used to receive, combine and generate data comprising detection of genomic regions (i.e., polymorphisms). In some embodiments, the instant method and system can comprise detection of the genomic regions that is based on one or more, two or more, three or more, four or more, five or more, six or more, seven or more, eight or more, nine or more or ten or more algorithms. The algorithms can be machine-learning algorithms, computer-implemented algorithms, machine-executed algorithms, automatic algorithms and the like.

The resulting data for each nucleic acid sample can be analyzed using feature selection techniques including filter techniques which assess the relevance of features by examining the intrinsic properties of the data, wrapper methods which embed the model hypothesis within a feature subset search, and embedded techniques in which the search for an optimal set of features is built into an algorithm or model.

In some instances, the detection of the one or more genomic regions is based on one or more statistical models. Statistical models or filtering techniques useful in the methods of the present invention include (1) parametric methods such as the use of two sample t-tests, ANOVA analyses, Bayesian frameworks, and Gamma distribution models, (2) model free methods such as the use of Wilcoxon rank sum tests, between-within class sum of squares tests, rank products methods, random permutation methods, or TNoM which involves setting a threshold point for fold-change differences in expression between two datasets and then detecting the threshold point in each gene that minimizes the number of missclassifications, and (3) multivariate methods such as bivariate methods, correlation based feature selection methods (CFS), minimum redundancy maximum relevance methods (MRMR), Markov blanket filter methods, Markov models, Hidden Markov Model (HMM), and uncorrelated shrunken centroid methods. In some instances, the Hidden Markov Model (HMM) is given an internal state, wherein the internal state is set according to an overall copy number of a chromosome in the first or second nucleic acid sample. In an instance, for a diploid chromosome, the HMI's internal states can be homozygous deletion (locally zero copies), heterozygous deletion (locally one copy), normal (locally two copies), duplication (more than two copies), and reference Gap (present as a state to distinguish gaps from Homozygous deletions). In another instance, for a Haploid chromosome (e.g., X or Y in a male), the HMIM's internal states can be homozygous deletion (locally zero copies), normal (locally two copies), duplication (more than two copies), and reference Gap (present as a state to distinguish gaps from Homozygous deletions). For example, for a Haploid chromosome, there may be no heterozygous deletion state available. In another instance, for trisomic and/or tetrasomic, additional intermediate the HMM states may have an additional intermediate state, wherein the intermediate state can account for the various CNV possibilities. In another embodiment, the Hidden Markov Model is used to filter the output by examination of measured insert-sizes of reads near a detected feature's breakpoint(s).

Other models or algorithms useful in the methods of the present invention include sequential search methods, genetic algorithms, estimation of distribution algorithms, random forest algorithms, weight vector of support vector machine algorithms, weights of logistic regression algorithms, and the like. Bioinformatics. 2007 Oct. 1; 23(19):2507-17 provides an overview of the relative merits of the algorithms or models provided above for the analysis of data. Illustrative algorithms include but are not limited to methods that reduce the number of variables such as principal component analysis algorithms, partial least squares methods, independent component analysis algorithms, methods that handle large numbers of variables directly such as statistical methods, and methods based on machine learning techniques. Statistical methods include penalized logistic regression, prediction analysis of microarrays (PAM), methods based on shrunken centroids, support vector machine analysis, and regularized linear discriminant analysis.

In some embodiments, an HMM-based detection algorithm can "segmentally" detect a large or substantially large CNV. In some instances, due to fluctuations in the coverage signal, there may be small detection gaps along the length of the true CNV. In an example, a 1 megabasepairs (Mbp) deletion may be detected as a small number of separate nominal detections, with small gaps between them. To mitigate this, a merge operation can be employed that identifies pairs of adjacent detections which are separated by a gap that is smaller than either of the two bracketing detections. The merge operation then measures the median coverage level in the gap. If the median coverage passes a predefined threshold, then the two detections are merged into a single large detection that spans the two original detections (including the enclosed detection gap). In an example, the true feature spans both detections, and the gap is a statistical artifact. Using real sequencing data of samples that are known to have large CNVs, this merge operation can permit a substantially better fidelity with respect to the true properties of the CNVs.

Methods and systems provided herein may further include the use of a feature selection algorithm as provided herein. In some embodiments of the present invention, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420).

In some embodiments of the present invention, a diagonal linear discriminant analysis, k-nearest neighbor algorithm, support vector machine (SVM) algorithm, linear support vector machine, random forest algorithm, or a probabilistic model-based method or a combination thereof is provided for the detection of one or more genomic regions. In some embodiments, identified markers that distinguish samples (e.g., diseased versus normal) or distinguish genomic regions (e.g., copy number variation versus. normal) are selected based on statistical significance of the difference in expression levels between classes of interest. In some instances, the statistical significance is adjusted by applying a Benjamini Hochberg or another correction for false discovery rate (FDR).

In some instances, the algorithm may be supplemented with a meta-analysis approach such as that described by Fishel and Kaufman et al. 2007 Bioinformatics 23(13): 1599-606. In some instances, the algorithm may be supplemented with a meta-analysis approach such as a repeatability analysis. In some instances, the repeatability analysis selects markers that appear in at least one predictive expression product marker set.

A statistical evaluation of the detection of the genomic regions may provide a quantitative value or values indicative of one or more of the following: the likelihood of diagnostic accuracy; the likelihood of disorder, disease, condition and the like; the likelihood of a particular disorder, disease or condition; and the likelihood of the success of a particular therapeutic intervention. Thus, a physician, who is not likely to be trained in genetics or molecular biology, need not understand the raw data. Rather, the data is presented directly to the physician in the form of the quantitative values to guide patient care. The results can be statistically evaluated using a number of methods known to the art including, but not limited to: the student's T test, the two-sided T test, Pearson rank sum analysis, Hidden Markov Model Analysis, analysis of q-q plots, principal component analysis, one way ANOVA, two way ANOVA, LIMMA, and the like.

F. Diseases or Conditions

Certain embodiments may include predicting, diagnosing, and/or prognosing a status or outcome of a disease or condition in a subject based on one or more biomedical outputs. Predicting, diagnosing, and/or prognosing a status or outcome of a disease in a subject may comprise diagnosing a disease or condition, identifying a disease or condition, determining the stage of a disease or condition, assessing the risk of a disease or condition, assessing the risk of disease recurrence, assessing the efficacy of a drug, assessing risk of an adverse drug reaction, predicting optimal drug dosage, predicting drug resistance, or a combination thereof.

The samples disclosed herein may be from a subject suffering from a cancer. The sample may comprise malignant tissue, benign tissue, or a mixture thereof. The cancer may be a recurrent and/or refractory cancer. Examples of cancers include, but are not limited to, sarcomas, carcinomas, lymphomas or leukemias. In some instances, a sample comprising cancer tissue is obtained, but no matched normal sample is obtained. In some instances, no matched normal sample is available. In some instances, a matched normal sample is obtained (e.g., for training and testing of a model disclosed herein).

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. The cancer may be a skin cancer, such as a basal cell carcinoma, squamous, melanoma, nonmelanoma, or actinic (solar) keratosis.

The cancer may be a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

The cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. The cancer may be a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenstrom macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Certain embodiments may include treating and/or preventing a disease or condition in a subject based on one or more biomedical outputs. The one or more biomedical outputs may recommend one or more therapies. The one or more biomedical outputs may suggest, select, designate, recommend or otherwise determine a course of treatment and/or prevention of a disease or condition. The one or more biomedical outputs may recommend modifying or continuing one or more therapies. Modifying one or more therapies may comprise administering, initiating, reducing, increasing, and/or terminating one or more therapies. The one or more therapies comprise an anti-cancer, antiviral, antibacterial, antifungal, immunosuppressive therapy, or a combination thereof. The one or more therapies may treat, alleviate, or prevent one or more diseases or indications.

Examples of anti-cancer therapies include, but are not limited to, surgery, chemotherapy, radiation therapy, immunotherapy/biological therapy, photodynamic therapy. Anti-cancer therapies may comprise chemotherapeutics, monoclonal antibodies (e.g., rituximab, trastuzumab), cancer vaccines (e.g., therapeutic vaccines, prophylactic vaccines), gene therapy, or combination thereof.

G. Systems, Kits, and Libraries

Methods of the disclosure can be implemented by way of systems, kits, libraries, or a combination thereof. The methods of the invention may comprise one or more systems. Systems of the disclosure can be implemented by way of kits, libraries, or both. A system may comprise one or more components to perform any of the methods or any of the steps of Certain embodiments. For example, a system may comprise one or more kits, devices, libraries, or a combination thereof. A system may comprise one or more sequencers, processors, memory locations, computers, computer systems, or a combination thereof. A system may comprise a transmission device.

A kit may comprise various reagents for implementing various operations disclosed herein, including sample processing and/or analysis operations. A kit may comprise instructions for implementing at least some of the operations disclosed herein. A kit may comprise one or more capture probes, one or more beads, one or more labels, one or more linkers, one or more devices, one or more reagents, one or more buffers, one or more samples, one or more databases, or a combination thereof.

A library may comprise one or more capture probes. A library may comprise one or more subsets of nucleic acid molecules. A library may comprise one or more databases. A library may be produced or generated from any of the methods, kits, or systems disclosed herein. A database library may be produced from one or more databases. A method for producing one or more libraries may comprise (a) aggregating information from one or more databases to produce an aggregated data set; (b) analyzing the aggregated data set; and (c) producing one or more database libraries from the aggregated data set.

VI. Computing Environment

Figure 10:
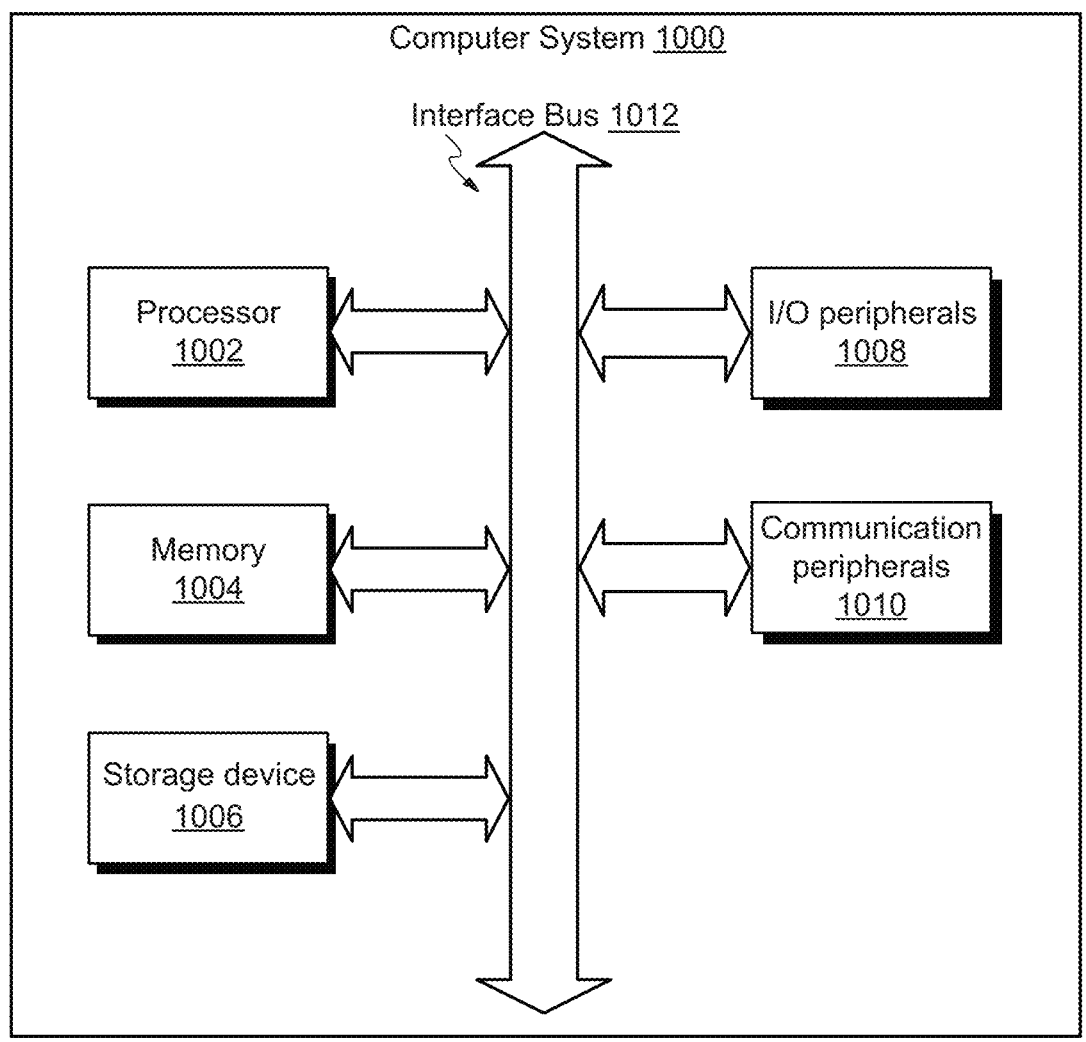
FIG. 10 illustrates an example of a computer system for implementing some of the embodiments disclosed herein.

FIG. 10 illustrates an example of a computer system 1000 for implementing some of the embodiments disclosed herein. Computer system 1000 may have a distributed architecture, where some of the components (e.g., memory and processor) are part of an end user device and some other similar components (e.g., memory and processor) are part of a computer server. Computer system 1000 includes at least a processor 1002, a memory 1004, a storage device 1006, input/output (I/O) peripherals 1008, communication peripherals 1010, and an interface bus 1012. Interface bus 1012 is configured to communicate, transmit, and transfer data, controls, and commands among the various components of computer system 1000. Processor 1002 may include one or more processing units, such as CPUs, GPUs, TPUs, systolic arrays, or SIMD processors. Memory 1004 and storage device 1006 include computer-readable storage media, such as RAM, ROM, electrically erasable programmable read-only memory (EEPROM), hard drives, CD-ROMs, optical storage devices, magnetic storage devices, electronic non-volatile computer storage, for example, Flash® memory, and other tangible storage media. Any of such computer-readable storage media can be configured to store instructions or program codes embodying aspects of the disclosure. Memory 1004 and storage device 1006 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with computer system 1000.

Further, memory 1004 includes an operating system, programs, and applications. Processor 1002 is configured to execute the stored instructions and includes, for example, a logical processing unit, a microprocessor, a digital signal processor, and other processors. Memory 1004 and/or processor 1002 can be virtualized and can be hosted within another computing system of, for example, a cloud network or a data center. I/O peripherals 1008 include user interfaces, such as a keyboard, screen (e.g., a touch screen), microphone, speaker, other input/output devices, and computing components, such as graphical processing units, serial ports, parallel ports, universal serial buses, and other input/output peripherals. I/O peripherals 1008 are connected to processor 1002 through any of the ports coupled to interface bus 1012. Communication peripherals 1010 are configured to facilitate communication between computer system 1000 and other computing devices over a communications network and include, for example, a network interface controller, modem, wireless and wired interface cards, antenna, and other communication peripherals.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A method of determining tumor purity of a biological sample of a subject for informing a cancer feature and evaluating a treatment efficacy for the subject, the method comprising:
    obtaining nucleic acid sequence data from one or more sequencers that represent a plurality of nucleic acid molecules of the biological sample of the subject;
    aligning the nucleic acid sequence data to a reference genome;
    identifying, based on the aligned nucleic acid sequence data, a set of genomic regions, wherein each genomic region of the set of genomic regions includes one or more nucleotide-sequence variants relative to a corresponding genomic region of the reference genome;
    determining a B-allele frequency for each genomic region of the set of genomic regions;
    determining, based on the B-allele frequencies of the set of genomic regions, a B-allele frequency distribution for the biological sample;
    processing the B-allele frequency distribution using a trained machine-learning model to estimate a probability of a true tumor purity as a function of a predicted tumor purity in the biological sample, wherein the trained machine-learning model is trained on a training dataset generated from nucleic acid sequence data derived from one or more tumor cells diluted into normal cells; and
    generating a report to inform the cancer feature and evaluate the treatment efficacy for the subject based on the estimated probability of a true tumor purity as a function of a predicted tumor purity in the biological sample.

2. The method of claim 1, wherein the obtained nucleic acid sequence data of the biological sample of the subject is whole exome sequencing data.

3. The method of claim 1, wherein the obtained nucleic acid sequence data of the biological sample of the subject is whole genome sequencing data.

4. The method of claim 1, further comprising:
    obtaining the biological sample from the subject; and
    sequencing the plurality of nucleic acid molecules of the obtained biological sample to generate the nucleic acid sequence data.

5. The method of claim 4, further comprising isolating the plurality of nucleic acid molecules prior to sequencing.

6. The method of claim 1, wherein the B-allele frequency distribution is normalized.

7. The method of claim 1, further comprising outputting a report comprising information identifying the B-allele frequency distribution.

8. The method of claim 1, further comprising outputting a report comprising estimated metric identifying the tumor purity.

9. The method of claim 8, wherein the report further comprises information identifying at least one biomarker.

10. The method of claim 1, wherein said generating the report to inform the cancer feature and evaluate the treatment efficacy for the subject comprises informing at least one of: (i) a cancer stage, or (ii) responsiveness to a cancer treatment.

11. A system comprising:
one or more data processors; and
a non-transitory computer readable storage medium containing instructions which, when executed on the one or more data processors, cause the one or more data processors to perform one or more operations comprising:
obtaining nucleic acid sequence data from one or more sequencers that represent a plurality of nucleic acid molecules of a biological sample of a subject;
aligning the nucleic acid sequence data to a reference genome;
identifying, based on the aligned nucleic acid sequence data, a set of genomic regions, wherein each genomic region of the set of genomic regions includes one or more nucleotide-sequence variants relative to a corresponding genomic region of the reference genome;
determining a B-allele frequency for each genomic region of the set of genomic regions;
determining, based on the B-allele frequencies of the set of genomic regions, a B-allele frequency distribution for the biological sample;
processing the B-allele frequency distribution using a trained machine learning model to estimate a probability of a true tumor purity as a function of a predicted tumor purity in the biological sample, wherein the trained machine-learning model is trained on a training dataset generated from nucleic acid sequence data derived from one or more tumor cells diluted into normal cells; and
generating a report to inform a cancer feature and evaluate the treatment efficacy for the subject based on the estimated probability of a true tumor purity as a function of a predicted tumor purity in the biological sample.

12. The system of claim 11, wherein the obtained nucleic acid sequence data of the biological sample of the subject is whole exome sequencing data.

13. The system of claim 11, wherein identifying the set of genomic regions further comprises:
identifying one or more candidate nucleotide-sequence variants in the nucleic acid sequence data; and
calculating reference and alternate read depths for each of the one or more candidate nucleotide-sequence variants.

14. The system of claim 11, wherein said instructions for generating the report to inform the cancer feature and evaluate the treatment efficacy for the subject comprises instructions for generating the report to inform at least one of: (i) a cancer stage, or (ii) responsiveness to a cancer treatment.

* * * * *

UNITED STATES PATENT AND TRADEMARK OFFICE
CERTIFICATE OF CORRECTION

| | | |
|---|---|---|
| PATENT NO. | : 12,217,830 B2 | Page 1 of 1 |
| APPLICATION NO. | : 17/735904 | |
| DATED | : February 4, 2025 | |
| INVENTOR(S) | : Phillips et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 325 days.

Signed and Sealed this
Twenty-ninth Day of July, 2025

Coke Morgan Stewart
*Acting Director of the United States Patent and Trademark Office*